(12) United States Patent
Keely et al.

(10) Patent No.: US 7,805,183 B2
(45) Date of Patent: Sep. 28, 2010

(54) STROMAL COLLAGEN IN THE DIAGNOSIS AND CHARACTERIZATION OF BREAST CANCER

(75) Inventors: Patricia Jo Keely, Madison, WI (US); Paolo P. Provenzano, Madison, WI (US); John Graham White, Madison, WI (US); Kevin William Eliceiri, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 474 days.

(21) Appl. No.: 11/766,321

(22) Filed: Jun. 21, 2007

(65) Prior Publication Data

US 2008/0015448 A1    Jan. 17, 2008

Related U.S. Application Data

(60) Provisional application No. 60/805,566, filed on Jun. 22, 2006, provisional application No. 60/892,687, filed on Mar. 2, 2007.

(51) Int. Cl.
*A61B 6/00* (2006.01)
*G01J 3/00* (2006.01)

(52) U.S. Cl. .................................. 600/476; 356/300
(58) Field of Classification Search ................ 600/476; 356/301, 318, 417
See application file for complete search history.

(56) References Cited

U.S. PATENT DOCUMENTS

| | | | |
|---|---|---|---|
| 5,769,081 A | 6/1998 | Alfano et al. | |
| 6,580,941 B2 | 6/2003 | Webb | |
| 6,615,063 B1 | 9/2003 | Ntziachristos et al. | |
| 6,687,000 B1 | 2/2004 | White | |
| 6,720,547 B1 | 4/2004 | Rajadhyaksha et al. | |
| 6,839,586 B2 | 1/2005 | Webb | |
| 6,879,394 B2 | 4/2005 | Amblard et al. | |
| 6,889,075 B2 | 5/2005 | Marchitto et al. | |
| 2003/0017111 A1 | 1/2003 | Rabito | |
| 2004/0206882 A1 | 10/2004 | Banks et al. | |
| 2005/0259249 A1 | 11/2005 | Dombeck et al. | |

OTHER PUBLICATIONS

International Search Report, Corresponding to International Application No. PCT/US07/71754, Mailed Jul. 11, 2008.
Written Opinion, Corresponding to International Application No. PCT/US07/71754, Mailed Jul. 11, 2008.

(Continued)

*Primary Examiner*—Eric F Winakur
*Assistant Examiner*—Michael T Rozanski
(74) *Attorney, Agent, or Firm*—Greenlee Sullivan P.C.

(57) ABSTRACT

The present invention provides methods and systems for evaluating biological materials for the diagnosis of disease, such as gland abnormalities, and the cancerous and precancerous conditions. Nonlinear optical microscopy techniques, such as MP microscopy and harmonic generation microscopy, are used to generate high resolution, three dimensional images of a test tissue, such as a biopsy tissue sample and tissue in whole organisms, that are analyzed, optionally in combination, to detect, identify and characterize tumor-associated collagen signatures. The presence, abundance and extent of histological features and structural motifs comprising tumor-associated collagen signatures may be directly and accurately correlated with the onset and progression of cancer, such as breast cancer. The present methods are capable of providing an accurate and selective diagnosis of cancer, and provide diagnostic information complementary to conventional diagnostic methods.

30 Claims, 33 Drawing Sheets

OTHER PUBLICATIONS

International Search Report, Corresponding to International Application No. PCT/US08/55453, Mailed Aug. 15, 2008.
Written Opinion, Corresponding to International Application No. PCT/US/08/55453, Mailed Aug. 15, 2008.
Abramoff et al. (2004) "Image Processing With ImageJ," *Biophotonics Int.* 11:36-42.
Ada-Nguema et al. (2006) "The Small GTPase R-Ras Regulates Organization of Actin and Drives Membrane Protrusions Through the Activity of PLC{epsilon}," *J. Cell Sci.* 119(7):1307-1319.
Aiello et al. (2005) "Association Between Mammographic Breast Density and Breast Cancer Tumor Characteristics," *Cancer Emidemiol. Biomarkers Prev.* 14:662-668.
Allinen et al. (2004) "Molecular Characterization of the Tumor Microenvironment in Breast Cancer," *Cancer Cell* 6:17-32.
Alowami et al. (2003) "Mammographic Density is Related to Stroma and Stromal Protteoglycan Expression," *Breast Cancer Res.* 5:R129-R135.
Aplin et al. (1999)"Integrin and Cytoskeletal Regulation of Growth Factor Signaling to the MAP Kinase Pathway," *J. Cell. Sci.* 112(5):695-706.
Baba et al. (2006) "Syndecan-1 and Syndecan-4 are Overexpressed in an Estrogen Receptor-Negative, Highly Proliferative Breast Carcinoma Subtype," *Breast Cancer. Res. Treat.* 98:91-98.
Baron et al. (1998) "p125Fak Focal Adhesion Kinase is a Substrate for the Insulin and Insulin-Like Growth Factor-I Tyrosine Kinase Receptors," *J. Biol. Chem.* 273:7162-7168.
Barcellos-Hoff et al. (1989) "Functional Differentiation and Alveolar Morphogenesis of Primary Mammary Cultures on Reconstituted Basement Membrane," *Development* 105:223-235.
Barsky et al. (1982) "Increased Content of Type V Collagen in Desmoplasia of Human Breast Carcinoma," *Am. J. Pathol.* 108:276-283.
Bavik et al. (2006) "The Gene Expression Program of Prostate Fibroblast Senescnece Modulates Neoplastic Epithelial Cell Proliferation Through Paracrine Mechanisms," *Cancer Res.* 66:794-802.
Becker et al. (2004) "Fluorescence Lifetime Imaging by Time-Correlated Single-Photon Counting," *Microsc. Res. Tech.* 63(1):58-66.
Benlimame et al. (2005) "FAK Signaling is Critical for ErbB-2/ErbB-3 Receptor Cooperation for Oncogenic Transformation and Invasion," *J. Cell. Biol./* 171:505-516.
Bird et al. (2004) "Simultaneous Two-Photon Spectral and Lifetime Fluorescence Microscopy," *Appl. Opt.* 43:5173-5182.
Bird et al. (2002) "Fiber-Optic Two-Photon Scanning Fluorescence Microscopy," *J. Microsc.* 208:35-48.
Bird et al. (2002) "Resolution Improvement in Two-Photon Fluorescence Microscopy with a Single-Mode Fiber," *Appl. Opt.* 41:1852-1857.
Bird et al. (2003) "Two-Photon Fluorescence Endoscopy with a Micro-Optic Scanning Head," *Opt. Lett.* 28:1552-1554.
Bird et al. (2005) "Metabolic Mapping of MCF10A Human Breast Cells via Multiphoton Fluorescence Lifetime Imaging of the Coenzyme NADH," *Cancer Res.* 65(19):8766-8773.
Boyd et al. (2005) "Mammographic Breast Density as an Intermediate Phenotype for Breast Cancer," *Lancet Oncol.* 6:798-808.
Boyd et al. (2002) "The Association of Breast Mitogens with Mammographic Densities," *Br. J. Cancer* 87:876-882.
Boyd et al. (2002) "Heritability of Mammographic Density, A risk Factor for Breast Cancer," *N. Eng. J. Med.* 347:886-894.
Boyd et al. (2001) "Mammographic Densities as a Marker of Human Breast Cancer Risk and Their Use in Chemoprevention," *Curr. Oncol. Rep.* 3:314-321.
Boyd et al. (1998) "Mammographic Densities and Breast Cancer Risk," *Cancer. Epidemiol. Biomarkers Prev.* 7:1133-1144.
Brakenhoff et al. (1985) "Three-Dimensional Chromatin Distribution in Neuroblastoma Nuclei Shown by Confocal Scanning Laser Microscopy," *Nature* 317(6039):748-749.
Brown et al. (2003) "Dynamic Imaging of Collagen and Its Modulation in Tumors in Vivo Using Second-Harmonic Generation," *Nat. Med.* 9:796-800.

Brown et al. (2001) "In Vivo Measurement of Gene Expression, Angiogenesis and Physiological Function in Tumors Using Multiphoton Laser Scanning Microscopy," *Nat. Med.* 7:864-868.
Byrne et al. (2000) "Plasma Insulin-Like Growth Factor (IGF) I, IGF-Binding Protein 3, and Mammographic Density," *Cancer Res.* 60:3744-3748.
Campagnola et al. (2002) "Three-Dimensional High-Resolution Second-Harmonic Generation Imaging of Endogenous Structural Proteins in Biological Tissues," *Biophys. J.* 81:493-508.
Campagnola et al. (2001) "Second-Harmonic Imaging Microscopy of Living Cells," *J. Biomed. Opt.* 6:277-286.
Candes et al. (1999) "Curvelets—A Surprisingly Effective Non-Adaptive Representation for Objects with Edges," In; *Curve and Surface Fitting*, Vanderbilt University Press.
Candes et al. (2002) "New Tight Frames of Curvelets and Optimal Representations for Objects with Smooth Singularities," Technical Report, Stanford University.
Centronze et al. (1998) "Multiphoton Excitation Provides Optical Sections from Deeper within Scattering Specimens than Confocal Imaging," *Biophys. J.* 75:2015-2024.
Chen et al. (Jul. 2002) "The $\beta_2$ Integrin Subunit-Deficient Mouse," *Am. J. Pathol.* 161(1):337-344.
Chu et al. (Apr. 2003) "Real-Time Second-Harmonic-Generation Microscopy Based on a 2-GHz Repetition rate Ti:Sapphire Laser," *Optics Express* 11(8):933-938.
Chung et al. (2005) "Molecular Insights into Prostate Cancer Progression: The Missing Link of Tumor Microenvironment," *J. Urol.* 173:10-20.
Condeelis et al. (2005) "The Great Escape: When Cancer Cells Hijack the Genes for Chemotaxis and Motility," *Ann. Rev. Cell Dev. Biol.* 21:695-718.
Cornell News (Feb. 2004) "New Optical Technique Can See MilliSecond Nerve Impulses in Healthy and Diseased Brains, Cornell Biophysicists Report," http://www.news.cornell.edu/release/Feb04/Optical_recordings.hrs.html.
Cox et al. (2003) "3-dimensional Imaging of Collagen Using Second Harmonic Generation," *J. Struct. Biol.* 141:53-62.
Cremazy et al. (2005) "Imaging in situ Protein-DNA Interactions in the Cell Nucleus Using FRET-FLIM," *Exp. Cell Res.* 309(2):390-396.
Croft et al. (2004) "Conditionsl ROCK Activation In vivo Induces Tumor Cell Dissemination and Angiogenesis," *Cancer Res.* 64:8994-9001.
DeMali et al. (2003) "Coupling Membrane Protrusion and Cell Adhesion," *J. Cell. Sci.* 116(12):2389-2397.
De Wever et al. (2003) "Role of Tissue Stroma in Cancer Cell Invasion," *J. Pathol.* 200:429-447.
Denk et al. (1990) "Two-Photon Laser Scanning Fluorescence Microscopy," *Science* 248:73-76.
Diamant et al. (1972) "Collagen; Ultrastructure and its Relation to Mechanical Properties as a Function of Ageing," *Proc. Royal. Soc. Lond.* 180B:293-315.
Diaspro et al. (2002) "Two-Photon Excitation Fluorescence Microscopy," In; *Confocal and Two-Photon Microscopy: Foundations, Applications, and Advances*, Diaspro, A. ed., Wiley-Liss, Inc., New York, pp. 39-73.
Donoho et al. (1995) "De-Noising by Soft-Thresholding," *IEEE Trans. Info. Theory*.
Elenbaas et al. (2001) "Human Breast Cancer Cells Generated by Oncogenic Transformation of Primary Mammary Epithelial Cells," *Genes Dev.* 15:50-65.
Eliceiri et al. (2005) "Tools for Zisualizing Multidimensional Images from Living Specimens," *Photochem. Photobiol.* 81:1116-1122.
Eliceiri et al. (2003) "Analysis of Histology Specimens Using a Lifetime Multiphoton Microscopy," *J. Biomed Opt.* 8:376-380.
Fata et al. (Aug. 2003) "Regulation of Mammary Gland Branching Morphogenesis by the Extracellular Matrix and Its Remodeling Enzymes," *Breast Cancer Res.* 6:1-11.
Flusberg et al. (2005) "Fiber-Optic Fluorescence Imaging," *Nat. Methods.* 2:941-950.
French et al. (1997) "Two-Photon Fluorescence Lifetime Imaging Microscopy of Macrophage-Mediated Antigen Processing," *J. Microsc.* 185(3):339-353.

Freund et al. (1986) "Second-Harmonic Microscopy of Biological Tissues," *Optics Lett.* 11:94-96.

Friedl et al. (2003) "Tumour-Cell Invasion and Migration: Diversity and Escape Mechanisms," *Nat. Rev. Cancer* 3(5):362-374 *Nat. Rev. Cancer* 3:362-374.

Friedl et al. (2004) "Collective Cell Migration in Morphogenesis and Cancer," *Int. J. Dev. Biol.* 48:441-449.

Galeotti et al. (1970) "On the Fluorescence of NAD(P)H in Whole-Cell Preparations of Tumours and Normal Tissues," *Eur. J. Biochem.* 17(3):485-496.

Gill et al. (2006) "The Association of Mammographic Density with Ductal Carcinoma in Situ of the Breast: The Multiethnic Cohort," *Breast Cancer Res.* 8:R30-.

Goldberg et al. (2005) "The Open Microscopy Environment (OME) Data Model and XML File: Open Tools for Informatics and Quantitative Analysis in Biological Imaging," *Genome Biol.* 6(5):R47-.

Guo et al. (2001) "Growth Factors and Stromal Matrix Proteins Associated with Mammographic Densities," *Cancer Epidemiol. Biomarkers Prev.* 10:243-248.

Guo et al. (Sep. 1999) "Subsurface Tumor Progression Investigated by Noninvasive Optical Second Harmonic Tomography," *Proc. Nat. Acad. Sci. USA* 96(19):10854-10856.

Habel et al. (2004) "Mammographic Density and Breast Cancer After Ductal Carcinoma In Situ," *J. Nat. Cancer. Inst.* 96:1467-1472.

Hagios et al. (1998) "Tissue Architecture: The Ultimate Regulator of Epithelial Function," *Philos Trans. R. Soc. Lond. B. Biol. Sci.* 353:857-870.

Hanahan et al. (2000) "The Hallmarks of Cancer," *Cell.* 100(1):57-70.

Harpur et al. (2001) "Imaging FRET Between Spectrally Similar GFP Molecules in Single Cells," *Nat. Biotechnol.* 19(2):167-169.

Hauck et al. (2001) "Inhibition of Focal Adhesion Kinase Expression or Activity Disrupts Epidermal Growth Factor-Stimulated Signaling Promoting the Migration of Invasive Human Carcinoma Cells," *Cancer Res.* 61:7079-7090.

Hawes et al. (2006) "Dense Breast Stromal Tissue Shows Greatly Increased Concentration of Breast Epithelium but No Increase in its Proliferative Activity," *Breast Cancer Res.* 8:R24-.

Hegerfeldt et al. (2002) "Collective Cell Movement in Primary Melanoma Explants: Plasticity of Cell-Cell Interaction, [beta]1-Integrin Function, and Migration Strategies," *Cancer Res.* 62(7):2125-2130.

Helmchen et al. (2002) "New Developments in Multiphotonic Microscopy," *Curr. Opin. Neurobiol.* 12:593-601.

Huang et al. (2002) "Two-Photon Fluorescence Spectroscopy and Microscopy of NAD(P)H and Flavoprotein," *Biophys. J.* 82:2811-2825.

Hurschler et al. (2003) "Application of a Probabilistic Microstructural Model to Determine Reference Length and Toe-to-Linear Region Transition in Bibrous Connective Tissue," *ASME J. Biomech. Eng.* 125:415-422.

Ishizawar et al. (2004) "c-Src and Cooperating Partners in Human Cancer," *Cancer Cell.* 6:209-214.

Iyengar et al. (2005) "Adipocyte-Derived Collagen VI Affects Early Mammary Tumor Progression in Vivo, Demonstrating a Critical Interaction in the Tumor/Stroma Microenvironment," *J. Clin. Invest.* 115:1163-1176.

Jacks et al. (2002) "Taking the Study of Cancer Cell Survival to a New Dimension," *Cell* 111(7):923-925.

Jaffe et al. (2005) "RHO GTPases: Biochemistry and Biology," *Ann. Rev. Cell Dev. Biol.* 21(1):247-269.

Jain et al. (2002) "Dissecting Tumour Pathophysiology Using Intravital Microscopy," *Nat. Rev. Cancer* 2(4):266-276.

Jiang et al. (May 2004) "Second-Harmonic Optical Coherence Tomography," *Optics Lett.* 29(10):1090-1092.

Jung et al. (2003) "Multiphoton Endoscopy," *Opt. Lett.* 28:902-904.

Katz et al. (2002) "Noninvasive Native Fluorescence Imaging of Head and Neck Tumors," *Technol. Cancer Res. Treat.* 1(1):9-15.

Keely et al. (Jul. 1995) "The Spatial and Temporal Expression of the $\alpha 2\beta 1$ Integrin and its Ligands, Suggest Important Roles in Mouse Mammary Morphogenesis," *Differentiation* 59(1):1-13.

Keely et al. (1995) "Alteration of Collagen-Dependent Adhesion, Motiliy, and Morphogenesis by the Expression of Antisense $\alpha 2$ Integrin mRNA in Mammary Cells," *J. Cell. Sci.* 108:595-607.

Keely et al. (1999) "R-Ras Signals Through Specific Integrin Alpha Cytoplasmic Domains to Promote Migration and Invasion of Breast Epithelial Cells," *J. Cell Biol.* 145(5):1077-1088.

Kirkptrick et al. (2005) "Endogenous Fluorescence Spectroscopy of Cell Suspensions for Chemopreventive Drug Monitoring," *Photchem. Photobiol.* 81(1):125-134.

Lakowicz et al. (1992) "Fluorescence Lifetime Imaging," *Anal. Biochem.* 202(2):316-330.

Lee et al. (2001) "Application of the Stretched Exponential Function to Fluorescence Lifetime Imaging," *Biophys. J.* 81(3):1265-1274.

Li et al.(2005) "The Association of Measured Breast Tissue Characteristics with Mammographic Density and Other Risk Factors for Breast Cancer," *Cancer Epidemiol Biomarkers Prev.* 14:343-349.

Li et al. (2000) "Use of MMTV-*Wnt*-1 Transgenic Mice for Studying the Genetic Basis of Breast Cancer," *Oncogene* 19:1002-1009.

Lin et al. (2003) "Progression to Malignancy in the Polyoma Middle T Oncoprotein Mouse Breast Cancer Model Provides a Reliable Model for Human Diseases," *Am. J. Pathol.* 163:2113-2126.

Liotta et al. (Jan. 2003) "Cancer's Deadly Signature," *Nat. Genet.* 33:10-11.

Lippincott-Schwartz et al. (2001) "Studying Protein Dynamics in Living Cells," *Nat. Rev. Mol. Cell Biol.* 2(6):444-456.

Lippincott-Schwartz et al. (2003) "Development and Use of Fluorescent Protein Makers in Living Cells," *Science* 300(5616):87-91.

Liu et al. (1995) "A Targeted Mutation at the Known Collagenase Cleavage Site in Mouse Type I Collagen Impairs Tissue Remodeling," *J. Cell. Biol.* 130:227-237.

Marsh et al. (2003) "Practical Implementation of Adaptive Optics in Multiphoton Microscopy," *Opt. Express* 11:1123-1130.

McCormack et al. (2006) "Breast Density and Patenchymal Patterns as Markers of Breast Cancer Risk: A Meta-Analysis," *Cancer Epidemiol. Biomarkers Prev.* 15:1159-1169.

McNeel et al. (2005) "Phase I Trial of a Monoclonal Antibody Specific for Alphavbeta3 Integrin (Medi-522) in Patients with Advanced Malignancies, Including as Assessment of Effect on Tumor Perfusion," *Clin. Cancer Res.* 11:7851-7860.

Mohler et al. (2003) "Second Harmonic Generation Imaging of Endogenous Structural Proteins," *Methods* 29:97-109.

Monaghan et al. (Jun. 1983) "Topographical Arrangement of Basement Membrane Proteins in Lactating Rat Mammary Gland: Comparison of the Distribution of Type IV Collagen, Laminin, Fibronectin, and Thy-1 at the Ultrastructural Level," *Proc. Nat. Acad. Sci. USA* 80:3344-3348.

Muti, P. (2004) "The Role of Endogenous Hormones in the Etiology and Prevention of Breast Cancer: The Epidemiological Evidence," *Ann. N.Y. Acad. Sci.* 1028-273-282.

Noel et al. (1998) "The Role of Stroma in Breast Carcinoma Growth in Vivo," *J. Mam. Gland Biol. Neoplasia* 3:215-225.

Orima et al. (2005) "Stromal Fibroblasts Present in Invasive Human Breast Carcinomas Promote Tumor Growth and Angiogenesis Through Elevated SDF-1/CXCL12 Secretion," *Cell* 121:335-348.

Oron et al. (Jul. 2004) "Depth-Resolved Structural Imaging by Third-Harmonic Generation Microscopy," *J. Struct. Biol.* 147(1):3-11.

Palmer et al. (2003) "Autofluorescence Spectroscopy of Normal and Malignant Human Breast Cell Lines," *Photochem. Photobiol.* 78(5):462-469.

Parr et al. (2004) "The Haptocyte Growth Factor Regulatory Factors in Human Breast Cancer," *Clin Cancer Res.* 10:202-211.

Parry et al. (1984) "Growth and Development of Collagen Fibrils in Connective Tissue," In; *Ultrastructure of the Connective Tissue Matrix*, Ruggeri et al. eds., The Hauge, Martinus Nijhoff, pp. 34-62.

Parsons et al. (2005) "Spatially Distinct Binding of Cdc42 to PAK1 and N-WASP in Breast Carcinoma Cells," *Mol. Cell Biol.* 25(5):1680-1695.

Paszek et al. (2005) "Tensional Homeostasis and the Malignant Phenotype," *Cancer Cell* 8:241-254.

Patterson et al. (2000) "Separation of the Glucose-Stimulated Cytoplasmic and Mitochondrial NAD(P)H Responses in Pancreatic Islet Beta Cells," *Proc. Nat. Acad. Sci. USA* 97(10):5203-5207.

Peter et al. (2004) "Imaging Molecular Interactions by Multiphoton FLIM," *Biol. Cell* 96(3):231-236.

Peter et al. (2005) "Multiphoton-FLIM Quantification of the EFP-mRFP1 FRET Pair for Localization of Membrane Receptor-Kinase Interactions," *Biophys. J.* 88(2):1224-1237.

Pitts et al. (2001) "Autofluorescence Characteristics of Immortalized and Carcinogen-Transformed Human Bronchial Epithelial Cells," *J. Biomed Opt.* 6(1):31-40.

Plotnikov et al. (2006) "Characterization of the Myosin-Based Source for Second-Harmonic Generation from Muschle Sarcomeres," *Biophys. J.* 90:693-703.

Poteryaev et al. (2005) "Involvement of the Actin Cytoskeleton and Homotypic Membrane Fusion in ER Dynamics in Caenorhabditis elegans," *Mol. Biol. Cell* 16(5):2139-2153.

Pradhan et al. (1995) "Steady State and Time-Resolved Fluorescence Properties of Metastic and Non-Metastic Malignant Cells from Different Species," *J. Photochem. Photobiol. B* 31:101-112.

Provenzano et al. (2006) "Collagen Reorganization at the Tumor-Stromal Interface Facilitates Local Invasion," *BMC Med.* 4:38-.

Ramanujam, N. (2000) "Fluorescence Spectroscopy of Neoplastic and Non-Neoplastic Tissues," *Neoplasia* 2(1-2):89-117.

Rangarajan et al. (2004) "Species- and Cell Type-Specific Requirements for Cellular Transformation," *Cancer Cell* 6(2):171-183.

Robu et al. (2003) "Localization of Functional Endothelin Receptor Signaling Complexes in Cardiac Transverse Tubules ," *J. Biol. Chem.* 278(48):48154-48161.

Ronnov-Jessen et al. (1995) "The Origin of the Myofibroblasts in Breast Cancer. Recapitulation of Tumor Environment in Culture Unravels Diversity an Implicates Converted Fibroblasts and Recruited Smooth Muscle Cells," *J. Clin. Invest.* 95(2):859-873.

Rueden et al. (2004) "VisBio: A Computational Tool for Visualization of Multidimensional Biological Image Data," *Traffic* 5:411-417.

Rutter et al. (2001) "Changes in Breast Density Associated with Initiation, Discontinuation, and Continuing Use of Hormone Replacement Therapy," *JAMA* 285:171-176.

Sachdev et al. (2001) "The IGF System and Breast Cancer," *Endocr. Relat. Cancer* 8:197-209.

Sahai et al. (2005) "Simultaneous Imaging of GFP, CFP and Collagen in Tumors in Vivo Using Multiphoton Microscopy," *BMC Biotechnol.* 5:14-.

Sato et al. (2004) "Gene Expression Profilinf of Tumor-Stromal Interactions Between Pancreatic Cancer Cells and Stromal Fibroblasts," *Cancer Res.* 64(19):6950-6956.

Shekhar et al. (Feb. 2003) "Extracellular Matrix-Stromal Cell Contribution to Neoplastic Phenotype of Epithelial Cells in the Breast," *Breast Cancer Res.* 5(3):130-135.

Shen et al. (1989) "Surface Properties Probed by Second-Harmonic and Sum-Frequency Generation," *Nature* 337:519-525.

Sieg et al. (2000) FAK Integrates Growth-Factor and Integrin Signals to Promote Cell Migration, *Nat. Cell. Biol.* 2:249-256.

Skala et al. (2005) "Multiphoton Microscopy of Endogenous Fluorescence Differentiates Normal, Precancerous, and Cancerous Squamous Epithelial Tissues," *Cancer Res.* 65(4):1180-1186.

Squirrell et al. (1999) "Long-Term Two-Photon Fluorescence Imaging of Mammalian Embryos Without Compromising Viability," *Nat. Biotechnol.* 17:763-767.

Squirrell et al. (2006) "CAR-1, a Protein that Localizes with the mRNA Decapping Component DCAP-1, Is Required for Cytokinesis and ER Organization in Caenorhabditis elegans Embryos," *Mol. Biol. Cell.* 17(1):336-344.

Stoller et al. (2002) "Polarization Dependent Optical Second-Harmonic Imaging of a Rat-Tail Tendon," *J. Biomed. Opt.* 7:205-214.

Strome et al. (2001) "Spindle Dynamics and Role of {Gamma}-Tubulin in Early Caenorhabditis elegans Embryos," *Mol. Biol. Cell* 12(6):1751-1764.

Sullivan et al. (2002) "Major Accomplishments for the Cancer Imaging Program," http://www.cancer.gov/dctd/cip_accomplishments.

Surmacz, E. (2000) "Function of the IGF_I Receptor in Breast Cancer," *J. Mammary Gland Biol. Neoplasia* 5:95-105.

Tadrous et al. (2003) "Fluorescence Lifetime Imaging of Unstained Tissues: Early Results in Human Breast Cancer," *J. Pathol.* 199(3):309-317.

Tlsty et al. (2001) "Know thy Neighbor: Stromal Cells can Contribute Oncogenic Signals," *Curr. Opin. Genet. Dev.* 11:54-59.

Ursin et al. (2005) "Greatly Increased Occurrence of Breast Cancers in Areas of Mammographically Dense Tissue," *Breast Cancer Res.* 7:R605-R608.

van Munster et al. (2005) "Fluorescence Lifetime Imaging Microscopy (FLIM)," *Curr. Opin. Genet. Dev.* 11(1):54-59.

Verveer et al. (2000) "Quantitative Imaging of Lateral ErbB1 Receptor Signal Propagation in the Plasma Membrane," *Science* 290(5496):1567-1570.

Wang et al. (2004) "Identification and Testing of a Gene Expression Signature of Invasive Carcinoma Cells within Primary Mammary Tumors," *Cancer Res.* 64(23):8585-8594.

Wang et al. (2002) "Single Cell Behavior in Metastic Primary Mammary Tumors Correlated With Gene Expression Patterns Revealed by Molecular Profiling," *Cancer Res.* 62:6278-6288.

Wang et al. (2005) "Tumor Cells Caught in the Act of Invading: Their Strategy for Enhanced Cell Motility," *Trends Cell. Biol.* 15:138-145.

West et al. (2005) "Determination of Stromal Signatures in Breast Carcinmoa," *PLpS Biol.* 3(6):e187-.

White et al. (1987) "An Evaluation of Confocal Versus Conventional Imaging of Biological Structures by Fluorescence Light Microscopy," *J. Cell Biol.* 105(1):41-48.

White et al. (2004) "Targeted Disruption of Beta1-Integrin in a Transgenic Mouse Model of Hu man Breast Cancer Reveals an Essential Role in Mammary Tumor Induction," *Cancer Cell.* 6:159-170.

Williams et al. (2005) "Interpreting Second-Harmonic Generation Images of Collagen I Fibrils," *Biophys. J.* 88:1377-1386.

Wokosin et al. (2003) "Optical Workstation with Concurrent, Independent Multiphoton Imaging and Experimental Laser Microbeam Capabilities," *Rev. Sci. Instrum.* 74(1).

Wolbarst et al. (Jan. 2006) "Evolving and Experimental Technologies in Medical Imaging," *Radiology* 238(1):16-39.

Wolf et al. (2003) "Compensation Mechanism in Tumor Cell Migration: Mesenchymal-Amoeboid Transition after Blocking of Pericellular Proteolysis," *J. Cell Biol.* 160:267-277.

Wolf et al. (2005) "Functional Imaging of Pericellular Proteolysis in Cancer Cell Invasion," *Biochimie.* 87(3-4):315-320.

Wozniak et al. (2005) "R-Ras Controls Membrane Protrusion and Cell Migration Through the Spatial Regulation of Rac and Rho," *Mol. Biol. Cell* 16(1):84-96.

Wozniak et al. (2003) "ROCK-Generated Contractility Regulates Breast Epithelial Cell Differentiation in response to the Physical Properties of a Three-Dimensional Collagen Matrix," *J. Cell. Biol.* 163:583-595.

Yazdanfar et al. (Jun. 2004) "Interferometric Second Harmonic Generation Microscopy," *Optic. Exp.* 12(12):2739-2745.

Zhang et al. (2002) "Creating New Fluorescent Probes for Cell Biology," *Nat. Rev. Mol. Cell Biol.* 3(12):906-918.

Zipfel et al. (2003) "Nonlinear Magic: Multiphoton Microscopy in the Biosciences," *Nat. Biotechnol.* 21:1369-1377.

Zipfel et al. (2003) "Live Tissue Intrinsic Emission Microscopy Using Multiphoton-Excited Native Fluorescence and Second Harmonic Generation," *Proc. Nat. Acad. Sci. USA* 100:7075-7080.

Zoumi et al. (2002) "Imaging Cells and Extracellular Matrix in Vivo by Using Second-Harmonic Generation and Two-Photon Excited Fluorescence," *Proc. Nat. Acad. Sci. USA* 99:11014-11019.

Plotnikoz, Sergey et al. (2006), "Optical clearing for improve contrast in second harmonic generation imaging of skeletal muscle," Biophysical Journal, 90:1: 328-339.

Takeshi, Yasui et al. (2005), "Tomographic Imaging of Collagen Fiber Orientation in Human Second-Harmonic-Generation Light," Optical and Quantum Electronics, 37:13-15: 1397-1408.

Supplementary European Search Report, corresponding to European Application No. 07798870.7, dated Mar. 24, 2010.

G

STROMAL COLLAGEN IN THE DIAGNOSIS AND CHARACTERIZATION OF BREAST CANCER

CROSS-REFERENCES TO RELATED APPLICATIONS

This application claims priority under 35 U.S.C. 119(e) to U.S. provisional Patent Application 60/805,566, filed Jun. 22, 2006, and U.S. Provisional Patent Application 60/892,687, filed Mar. 2, 2007, which are both hereby incorporated by reference in their entireties.

STATEMENT ON FEDERALLY SPONSORED RESEARCH OR DEVELOPMENT

This invention was made with government support awarded by the following agencies: NIH grants CA076537 and EB000184 and Department of Defense Breast Cancer Research Program Grant Number BC031277. The United States government has certain rights in the invention.

REFERENCE TO SEQUENCE LISTING, A TABLE, OR A COMPUTER PROGRAM LISTING COMPACT DISK APPENDIX

Not Applicable

BACKGROUND OF THE INVENTION

Biomedical imaging plays a central role in a large number of diagnostic and therapeutic procedures including visualizing external and internal anatomical and physiological structures, features, and systems; evaluating complex events in the body at the organ, tissue, cellular, and molecular levels, and facilitating image guided surgery techniques. Imaging allows physicians and other health care professionals to detect and diagnose the onset of disease, injury, and other disorders at an early stage and to accurately monitor progression or remission of a condition. Biomedical imaging also enables delivery of targeted and minimally invasive therapies for treating and managing a range of conditions. A large number of applications of biomedical imaging have matured into robust, widely used clinical techniques including planar projection and tomographic x-ray imaging, magnetic resonance imaging, ultrasound imaging, and gamma ray imaging.

Biomedical images are generated by detecting electromagnetic radiation, nuclear radiation, acoustic waves, electrical fields, and/or magnetic fields transmitted, emitted and/or scattered by materials, where the materials can be biological materials and/or materials introduced in the body such as implants, contrast agents, infusions, tracers, etc. Modulation of energy (e.g., radiative, acoustic, etc.) and/or particles provided to a sample via interaction with materials such as biological molecules and tissue structures yields patterns of transmitted, scattered or emitted radiation acoustic waves, electrical fields or magnetic fields that contain useful anatomical, physiological, and/or biochemical information. Modulation may occur via mechanisms involving interactions of endogenous materials in the sample and/or mechanisms involving interactions of exogenous imaging agents introduced to a sample to enhance the usefulness of the acquired image, such as contrast agents, dyes, optically or radiolabel materials, biomarkers, and other agents. Biomedical imaging has been demonstrated as generally useful for providing images of surface and subsurface components of tissue samples and also provides a means of real time monitoring of components of biological samples, in vivo and in vitro.

Advanced optical imaging methods, such as confocal scanning laser tomography and optical coherence tomography, have emerged as valuable molecular imaging techniques for visualizing biological processes at a cellular and subcellular (e.g., molecular) levels. Established optical molecular imaging techniques are based on monitoring spatial variations in a variety of optical parameters including the intensities, polarization states, and frequencies of transmitted, reflected, and emitted electromagnetic radiation. Given that many biological materials of interest are highly turbid with respect to most frequencies in the ultraviolet and visible regions of the electromagnetic spectrum, research is currently directed to developing and enhancing imaging techniques using near infrared excitation radiation from about 700 nanometers to about 1200 nanometers corresponding to an "optical window" present in many of these materials. Electromagnetic radiation of this wavelength range is capable of substantial penetration (e.g., up to a millimeter) in many biological materials and is considerably less phototoxic than visible and ultraviolet electromagnetic radiation. Infrared optical molecular imaging techniques, therefore, offer the promise of providing nondestructive and noninvasive imaging of subsurface biological structures in biological samples.

Recent advances in high intensity, mode locked near infrared laser optical sources make nonlinear optical imaging methods, such as multiphoton (MP) microscopy and second harmonic generation (SHG), an important class of infrared molecular imaging methods for visualizing cellular and subcellular structures in biological samples. Nonlinear imaging techniques are particularly useful for providing high resolution images for probing physiology, morphology, cellular microenvironments, and cell-extracellular matrix and cell— cell interactions in intact tissues and living organisms. MP microscopy uses a high intensity, temporally short laser pulse to provide highly localized nonlinear excitation of fluorescence. In two photon fluorescence excitation techniques, for example, absorption of two lower energy photons simultaneously excites an electronic transition in a fluorophor, thereby causing radiative decay resulting in fluorescence emission of a single higher energy photon. As the probability of two photon absorption is relatively low (for example, as compared to single photon absorption), excitation in this technique is limited to a spatially confined focused region of the excitation beam having a sufficiently high intensity of photons. Second harmonic generation, in contrast, does not arise from an absorptive process. Rather, the second harmonic phenomenon results from a nonlinear scattering interaction of radiation with a non-centrosymmetric environment of a sample. In this techniques, an intense laser field is provided to the sample that induces a nonlinear, second order, polarization in the spatial orientation of molecules exposed to the excitation radiation. The induced polarization results in generation of a coherent wave having a frequency that is exactly two times that of the incident excitation radiation. In both MP microscopy and SHG, a two dimensional image is typically generated by detecting fluorescence or polarized light, respectively, while the excitation beam is systematically scanned across a given layer of the sample. Three dimensional images are formed by scanning a plurality of layers at different depths.

A number of advantages are provided by nonlinear techniques relative to conventional linear optical imaging techniques. First, these techniques are ideally suited for use of infrared excitation radiation, particularly having wavelength in the optical window region from about 700 nanometers to about 1200 nanometers of many biological samples. Thus, nonlinear optical techniques are capable of penetrating and imaging many types of tissues and typically do not lead to significant photoinduced sample degradation during analysis. Second, nonlinear optical imaging methods are capable of providing images with enhanced axial resolution relative to conventional optical imaging techniques due to the highly localized excitation arising from the nonlinear dependence of excitation rate on illumination intensity. Third, some applications of nonlinear advanced optical techniques to biomedical imaging, such as second harmonic generation methods, do not require exogenous labeling/staining. These techniques, therefore, can eliminate the need for complex and invasive labeling procedures common to conventional optical molecular imaging methods. Finally, different nonlinear techniques may be combined and used in tandem to provide complementary information relating to tissue structure and composition. For example, the combination of MP and SHG images provides enhanced cellular and subcellular information, as each technique employs fundamentally different excitation processes and, thus, provides substantially different contrast mechanisms.

Given the demonstrated capabilities of nonlinear optical imaging techniques for probing cellular and subcellular morphology and composition, researchers are currently pursuing applications of these techniques for detecting, diagnosing, and monitoring the onset and progression of disease. Proposed applications of nonlinear optical imaging include diagnosis of cancer and in situ evaluation of angiogenesis and metastasis processes, and monitoring the progression of neurodegenerative diseases such as Alzheimer's disease. Although the potential for such applications, including endoscopy and optical biopsy applications, is clear, these techniques have not yet matured to the point so as to provide a robust clinical tool. To develop this, and other important applications of nonlinear optical imaging, histopathological features and structural motifs in biomedical images that correlate with specific disease conditions in human and animal patients must be identified and characterized, particularly as a function of the progression or remission of a disease. Further, enhancements are also need to transform the instrumentation used in nonlinear imaging techniques into a reliable instrument capable of implementation in range of clinical applications.

It will be understood from the following and foregoing that a clear need exists in the art for biomedical imaging techniques for the in vivo or in vitro (including ex vivo) analysis of biological samples. Noninvasive and nondestructive nonlinear optical imaging and analysis methods are needed that are capable of providing useful information relating to anatomical morphology and composition, including at the tissue, cellular, and subcellular levels, for detecting the onset and monitoring the progression of conditions including diseases such as cancer. Nonlinear optical biopsy and endoscopy methods are needed to improve accuracy and precision in diagnostic efforts and to enable diagnosis at a desirable stage of timing, e.g., to facilitate earlier therapy, preventive care and the proper treatment regime for a particular tumor classification following detection to achieve better health.

SUMMARY OF THE INVENTION

The present invention broadly provides methods and systems for detecting, identifying, and characterizing conditions, including diseases and other disorders, in biological materials. In particular embodiments, the invention relates to conditions of the human breast including cancers such as carcinoma. Methods and systems are provided for detecting, locating, and characterizing tumors and precancerous tissue via high resolution multi dimensional imaging (including two-dimensional and three-dimensional) of tissue using MP microscopy and/or SHG nonlinear optical imaging techniques. The methods and systems can be employed and in vivo (including application to a patient sample in situ over real time) in vitro (including ex vivo as analogous to classical histopathology).

The present invention further and preferably provides non-invasive and nondestructive methods and systems that are capable of identifying and characterizing cancer in non-fixed, non-sectioned, and/or non-stained tissue, including excised tissue samples and tissues in whole organisms. The present invention provides highly sensitive, selective and specific methods and systems that are capable of directly evaluating subsurface tumor development and progression over the spectrum from a normal state to advanced cancer states. The present methods and systems are capable of detecting and characterizing cancer in a range of tissue types, including breast tissue and epithelial tissue. Systems and methods of the present invention provide diagnostic information that is different from, and can be complementary to, information provided by other detection methods, such as mammography, ultrasound and conventional histological staining techniques.

In one aspect, the present invention provides a method of evaluating a test tissue sample for the diagnosis of cancer using nonlinear optical imaging. Methods of this aspect of the present invention are useful for identifying the presence, absence or invasiveness of cancer and/or for assessing the composition, state, physical dimensions, or progression of tumors and/or precancerous tissue in a sample. In one embodiment of this aspect of the present invention, a test tissue sample from a test subject is provided that comprises a stromal collagen component. Some examples of particularly useful tissues for evaluation by the present methods include breast, cervix, lung, prostate, esophagus, colon, skin, eye, and other tissues. In embodiments, tissue/cell components of epithelial, stromal, mesenchymal, neuronal, immune, vascular origin and certain extracellular matrix components are apt for examination.

The invention provides methods and output in connection with a test image, such as a two or three dimensional image, or test imaging data generated from the test tissue sample using a nonlinear optical imaging technique. In an embodiment, MP microscopy, harmonic generation microscopy (e.g., second harmonic generation, third harmonic generation, fourth harmonic generation etc.) or any combination of these techniques is used to generate a three-dimensional test image of at least a portion of the test tissue sample, for example, generating an image of a selected layer or region of the test tissue sample. The test image or test imaging data is analyzed by observing stromal collagen and the associated cell morphology and fluorescence at the tumor-stromal interface in the test sample for detection of one or more tumor-associated collagen signatures (TACS), thereby evaluating the sample for the diagnosis of cancer.

In an embodiment, the test image or test imaging data is analyzed by observing stromal collagen and the cell morphology, phenotype, and stromal interaction in the test sample for detection of a tumor-associated collagen signature profile comprising one or more tumor-associated collagen signatures.

Optionally, methods of this diagnostic aspect of the present invention may further comprise the step of analyzing the test image or test imaging data of the test tissue sample by comparison with one or more reference images or reference imaging data corresponding to a reference tissue sample, such as a sample corresponding to normal (i.e., noncancerous) tissue, for detection and/or characterization of one or more tumor-associated collagen signatures. Methods of this aspect of the present invention may further comprise the step of generating additional images of the test tissue, including images corresponding to different layers or regions of the test tissue and images generated by different linear and/or nonlinear optical imaging techniques. Optionally, methods of this embodiment include the step of comparing and/or combining different images of the test tissue for the detection and/or characterization of tumor-associated collagen signatures and/or profiles.

As used in this description, the term "tumor-associated collagen signature" and "signature" are used interchangeably in the present description and refer to one or more proteinaceous structures that can be found in tissue of an organism, where the relative or absolute presence, prevalence, amount, or density of the one or more structures, in addition to physical features thereof, can be correlated with a cancerous (as defined herein) condition. In a useful embodiment, the tumor-associated collagen signature(s) is found in the extracellular matrix component of a tissue. In a particular embodiment, the tumor-associated collagen signature(s) is found in a stromal region of breast tissue. In a preferred example, the proteinaceous structures are collagenous, wherein at least a portion of the structure includes collagen, including in particular fibrillar collagen.

Tumor-associated collagen signatures useful for methods of identifying and characterizing cancer in the present invention include: (i) an enhanced collagen density, (ii) collagen localization or deposition level in the test tissue sample, (iii) an enhanced level of taut collagen fibers in the test tissue sample and (iv) an enhanced radial alignment pattern of collagen fibers. In the context of this discussion, an enhanced feature(s) or characteristic(s), e.g. density, organization, or levels of collagen, taut configuration and radial alignment, refers to an absolute or relative increase in a selected property relative to normal condition tissue (i.e. noncancerous and/or non-precancerous tissue). In the present invention, features or characteristics corresponding to a tumor-associated collagen signature may be quantitatively defined as an enhancement relative to a reference level, such as reference tissue having a normal or cancerous condition, for example, a non-cancerous condition or a different tumor region, or a tumor to tumor comparison, and, optionally, refers to normal condition tissue of the test subject. Tumor-associated collagen signatures in test images may be identified, qualitatively evaluated, and/or quantitatively assessed by a doctor or other healthcare professional, a computer processor, or a computer assisted image processing system.

In one embodiment of the present invention, the tumor-associated collagen signature is an enhanced collagen density, organization, and/or deposition level in the test tissue sample relative to a first reference level. In this description, the expression "first reference level" refers to reference tissue having a normal condition, for example, a non-cancerous condition, and, optionally, refers to normal condition tissue of the test subject. In one embodiment useful for identifying the presence, absence or invasiveness of cancer in a test sample and/or characterizing the state of cancer in a sample, enhanced collagen density of the tumor-associated collagen signature is at least a factor of two times greater than that of the first reference level. In some embodiments enhanced collagen density of the tumor-associated collagen signature is between 2 to 10 times greater than that of the first reference level, more preferably for some applications between 2 to 3 times greater than that of the first reference level.

Enhanced collagen density in tumor-associated collagen signatures of this aspect of the present invention are typically spatially localized in a tissue sample. Enhanced collagen density may be present in a tissue sample, for example, in clusters, aggregates or other microstructures. In an embodiment, a tumor-associated collagen signature is characterized by one or more spatially localized regions of enhanced collagen density having physical dimensions (e.g., length, width, diameter etc.) ranging from 30 microns to 100 microns in a tissue sample.

Identifying, characterizing and quantifying enhanced collagen density of tumor-associated collagen signatures in this aspect of the present invention is commonly achieved via observation of increased signal intensities using one or more nonlinear spectroscopic imaging techniques, including second harmonic generation, a combination of second harmonic generation and multiphoton fluorescence spectroscopy, multiphoton intensity and fluorescence lifetime imaging microscopy and Multiphoton spectral lifetime imaging microscopy. In some methods, enhanced collagen density in a tumor-associated collagen signatures is identified and characterized by observing high signal intensities localized to one or more regions of a tissue sample having physical dimensions (e.g., length, width, diameter etc.) ranging from 30 microns to 100 microns In some embodiments, the enhanced collagen density or deposition level of the tumor-associated collagen signature observable in the image or imaging data is located proximal to a tumor or is located proximal to precancerous tissue evolving into a cancerous state.

In an embodiment, the enhanced collagen density signature is employed in detection or diagnosis of cancer including breast cancer. In an embodiment, a further classification of the signature is carried out via identification of sub-signatures associated with an observed tumor-associated collagen signature. In an embodiment, the sub-signature identified is correlated with a clinical diagnosis. For example, the presence of a single area field and/or threshold volume of enhanced density is correlated using the present invention with the presence of cancer or assessment of cancer at a qualitatively and/or quantitatively lower grade clinical rating. Alternatively, the presence of multiple area fields and/or greater single or aggregate threshold volumes of enhanced density can correlate with a clinically advanced stage of cancer. In embodiments, further correlations are developed for association of a sub-signature with clinical terminology including "benign" and "malignant." In embodiments, sub-signatures observed over a period of time are further used in the context of informing a diagnostic assessment such as by noting the qualitative and/or quantitative changes and/or rates of change in onset, progression or remission of disease. Therefore, the signature and/or sub-signatures associated with a signature are used in certain diagnostic applications of the present invention for assessing presence or absence of invasion, metastasis and/or metastatic potential.

In another embodiment of the present invention, the tumor-associated collagen signature is an enhanced level of taut collagen fibers in the test tissue sample relative to a second reference level. In this description, the expression "second reference level" refers to reference tissue having a normal condition, for example, a non-cancerous condition, and, optionally, refers to normal condition tissue or a small tumor of the test subject. The terms "taut fiber" or "taut collagen fiber" are used interchangeably in the present description and refer to a fibrillar physical structure of a proteinaceous material wherein a single fibrillar unit or a plurality of fibrillar units have a configuration that can qualitatively be described with the term taut as ordinarily understood. Taut collagen fibers may arise from stretching of the stroma due to tumor formation and growth or other mechanisms arising from physical rearrangement or stress of collagen fibers due to the presence and/or growth of a tumor. To further understand this term, the structure may have a generally straightened, rod-like, and/or erect configuration, but need not be absolutely so. As applied to a collection of fibers, the term similarly relates to the appearance of at least some, but not necessarily all, of the fibers being straightened, etc. as for a single fiber. As an illustration, a taut fiber may be compared to an elastomeric material to which at least some tension has been applied, thereby at least partially straightening, elongating and/or unraveling the elastomeric material, fully straightening the material, and possibly even stretching the material, as opposed to being completely limp. For further illustration, a taut fiber can have a bowed, slightly arched, rod-like, straight, erect, and even possibly stretched appearance. In an embodiment, the proteinaceous material of the taut fiber is collagen, and more preferably for some applications stromal collagen. In some embodiments, the proteinaceous material is present within breast tissue or epithelial tissue.

In an embodiment, the term "taut fiber" refers to the general alignment or realignment of a plurality of collagen fibers in a breast tissue having a cancerous or precancerous condition relative to the alignment of a second plurality of collagen fibers in normal breast tissue (including a normal portion of breast tissue). In an embodiment, the term can be understood as being relative to the non-taut or less taut structure of stromal collagen of normal breast tissue.

In one embodiment, the tumor-associated collagen signature corresponds to an observation of at least one taut collagen fiber or preferably for some applications a network of taut collagen fibers in the image or image data of the test tissue. In one embodiment useful for identifying the presence or absence of cancer in a test sample and/or characterizing the state of cancer in a sample, the tumor-associated collagen signature corresponds to a concentration of taut fibers in the image that is greater than that of the second reference level, for example an order of magnitude greater than that of the second reference level. In another embodiment, the tumor-associated collagen signature is quantitatively evaluated by assessing the degree of tautness of one or more collagen fibers or networks of taut collagen fibers in the image or image data of the test tissue. In another embodiment, the tumor-associated collagen signature is quantitatively evaluated by assessing the proximity of taut collagen fibers and fiber networks to a growing tumor or precancerous tissue. Identification and characterization of taut fibers in image and image data may optionally be achieved via wavelet and curvelet analysis methods including, wavelet and curvelet transformations.

In an embodiment, the enhanced taut fiber signature is employed in detection or diagnosis of cancer including breast cancer. In an embodiment, a relative scale is developed for rating a degree of the signature. In an embodiment, the scale is correlated with a clinical diagnosis. For example, the presence of a single area field and/or threshold volume of enhanced taut fiber or plurality of taut fibers can be correlated with the presence of cancer or assessment of cancer at a qualitatively lower grade clinical rating. Alternatively, the presence of multiple area fields and/or increased single or aggregate occurrences of enhanced taut fibers can correlate with a clinically advanced stage of cancer. In embodiments, further correlations are developed for association of the degree of the signature with clinical terminology including "benign" and "malignant." In embodiments, the degrees/levels observed over a period of time are further used in the context of informing a diagnostic assessment such as by noting the qualitative and/or quantitative changes and/or rates of change. Therefore the signature is used in diagnostic applications in assessing the presence or absence invasiveness of metastasis and/or metastatic potential.

In another embodiment of the present invention, the tumor-associated collagen signature is an enhanced radial alignment pattern of collagen fibers in the test tissue sample relative to a third reference level. In this description, the expression "third reference level" refers to reference tissue having a normal or cancerous condition, for example, a non-cancerous condition or more confined (less invasive) tumor region, and, optionally, refers to normal condition tissue or different tumor or tumor region from the test subject. The term "radial alignment pattern" in this context refers to a structural description of a spatial orientation of one or more collagen fibers relative to a suspected tumor cell structure, tumor mass structure or precancerous tissue. The term can be further understood in the context of a breast tissue model of disease where there is an invasive tumor that develops in the tissue. The tumor can be described as having an outer margin or boundary that demarcates the tumor periphery. Outside the tumor periphery, or in the absence of a tumor, there can be a normal stromal region of the tissue. In such a normal stromal region, the collagen fibers can exhibit a normal alignment pattern wherein the fibers do not have any particular orientation; thus the normal pattern can be described as random relative to any particular spatial region in the tissue. In contrast, stromal collagen can appear to be reoriented relative to a tumor margin, where collagen fibers can adopt a radial alignment pattern such as being substantially normal (i.e. with in 10% of a perpendicular angular orientation) with respect to an imaginary border drawn to approximate the tumor margin. There can be substantial variation in the orientation angle(s) in reoriented stromal collagen exhibiting a radial alignment pattern, especially when one considers that the viewing angle can influence a perceived angle in an image from a three-dimensional specimen. In an embodiment, the term is based on a relative standard in comparison to normal stromal collagen. Quantification and characterization of the angular orientation of collagen fibers in image and image data may optionally be achieved via wavelet and curvelet analysis methods including, wavelet and curvelet transformations.

Enhanced radial alignment of a tumor-associated collagen signature may be identified, characterized and/or quantified by observation of the spatial orientations of collagen fibers, for example the spatial orientation of collagen fibers relative to a tumor boundary. In an embodiment, for example, the present methods include the step of measuring a distribution of angles of a plurality of collagen fibers relative to a tumor boundary surface. A measured angular distribution in this aspect may be characterized by one or more maxima. Enhanced radial alignment is identified in some methods by a transition from a distribution of angles of a plurality of collagen fibers relative to a tumor boundary surface characterized by a maximum near zero degrees to a distribution having one or more maxima shift to higher angles. In some embodiments, for example, observation of collagen fibers oriented at angles larger than 30 degree relative to the tumor surface boundary is indicative of a tumor-associated collagen signature. In some embodiments, for example, observation of a distribution of angular orientations of collagen relative to a tumor boundary having a maximum equal to or greater than 30 degrees, preferably in some embodiments equal to or greater than 50 degrees, is indicative of a tumor-associated collagen signature of the present invention. Measurement of angular orientations of collagen fibers relative to a tumor boundary, and distributions thereof, is particularly useful in the present invention for characterizing the staging and prognosis of disease, and for developing effective treatment strategies.

In an embodiment, the enhanced radial alignment signature is employed in detection or diagnosis of cancer including breast cancer. In an embodiment, one or more enhanced radial alignment signatures are evaluated for identification of sub-signatures that correlate with a specific type of cancerous and/or precancerous tissue. In another embodiment, one or more enhanced radial alignment signatures are evaluated for identification of sub-signatures that correlated with precancerous, onset or advanced stages of cancer useful for clinical diagnosis. For example, the presence of a single area field and/or threshold level of enhanced radial alignment patterning can be correlated with a sub-signature associated with the presence of cancer or assessment of cancer at a qualitatively lower grade clinical rating. Alternatively, the presence of multiple area fields and/or increased single or aggregate occurrences of enhanced radial alignment patterns can correlate with a sub-signature associated with a clinically advanced stage of cancer. In embodiments, further correlations are developed for association of observed sub-signatures with clinical terminology including "benign" and "malignant." In embodiments, enhanced radial alignment signatures and/or sub-signatures are observed over a period of time and are further used in the context of informing a diagnostic assessment such as by noting the qualitative and/or quantitative changes and/or rates of change. Therefore the signature and/or sub-signature are used in diagnostic applications in assessing presence, absence or likelihood of metastasis and/or metastatic potential.

In an embodiment, a first, second, or third reference level can each independently relate to a reference tissue having a normal condition or a disease condition at a particular disease stage or historical time point. For example, a first, second, or third reference level can be a previously assessed level from the same or different test sample from the same patient or a different patient. When the reference level is derived from the same patient, there can be a particular diagnostic advantage in such level serving as an internal control, whether or not temporally synchronized with the test sample. In the specific example where a historical reference level itself reflects a disease state, the reference level can serve to evaluate the present test sample while also providing other information, e.g., regarding the level or rate of change. When the reference level reflects a disease state, there can be a diagnostic advantage in facilitating a comparison of the reference image with the test image to accurately assess the test sample. In a preferred embodiment, greater diagnostic information is achieved by accruing and evaluating multiple reference levels.

In some embodiments, tumor-associated collagen signatures are identified and/or characterized using statistical and or advanced signal processing techniques. Images and/or image date is analyzed in some methods using statistical and or advanced signal processing techniques capable of generated quantitative parameters that can be correlated to the presence or absence of disease, and/or the stage or identity of a disease, and/or potential clinical outcomes. In an embodiment, for example, images and/or image data is analyzed via statistical methods that provide a collagen intensity value that may be compared to a threshold intensity value for the identification, characterization and use of tumor-associate collagen signatures characterized by an increase in signal intensities due to increased collagen concentrations (i.e., TACS1).

In another embodiment, for example, images and/or image data is analyzed via statistical and signal processing methods that provide values of the angles of collagen fibers relative to a tumor boundary for the identification, characterization and use of for the identification, characterization and use of tumor-associate collagen signatures characterized by the presence of radially aligned collagen fibers (TACS3). Analysis methods of this aspect of the present invention may optionally generate a distribution of angles of a plurality of collagen fibers relative to a tumor boundary and/or an average value of the angles of collagen fibers relative to a tumor boundary.

The present invention includes use of curvelet and/or wavelet analysis methods, including curvelet transforms and wavelet transforms, for determining the angular orientations of collagen fibers relative to a tumor boundary. Use of curvelet or wavelet analysis is useful generally for determining the morphology, organization and spatially orientation of collagen fibers in a tissue sample. Specifically, curvelet or wavelet analysis provides a means for detecting the presence of taut collagen fibers for the identification, characterization and use of tumor-associate collagen signatures characterized by the occurrence of taut collagen fibers (TACS2). Specifically, curvelet or wavelet analysis provides a means for determining the angles of collagen fibers relative to a tumor boundary for the identification, characterization and use of tumor-associate collagen signatures characterized by the presence of radially aligned collagen fibers (TACS3).

Tumor-associated collagen signatures identified in test images and test data generated by nonlinear optical imaging techniques provide reliable indicators for detecting and characterizing the composition, physical state, progression and invasiveness of cancer or precancerous tissue. In one embodiment, for example, identification of enhanced collagen density or deposition level in the test tissue is used to detect the onset of cancer and tumor formation at a very early stage. Identification of enhanced taut fibers and enhanced radial alignment patterns is useful in the present methods for identifying and characterizing the stage of development (e.g., tumor grade, tumor progression or remission) of cancer in a subject, for example, by determining the growth rate and/or stage or grade of a tumor or precancerous tissue, evaluating malignancy and assessing the occurrence of or potential for metastasis. In another embodiment, a combination of two or more signatures (e.g., density and taut fibers, density and radial alignment patterns, and/or taut fibers and radial alignment patterns) is employed in diagnostic applications. In yet another embodiment, a combination of the three tumor-associated collagen signatures is employed in diagnostic applications. Any number of reference tissue samples and/or reference levels or extent of reference level data can be used in the present methods.

The methods of the present invention optionally include the step of quantitatively evaluating one or more tumor-associated collagen signatures identified in test images and test data to provide information relevant to the diagnosis of cancer. For example, some embodiments further comprise the step(s) of measuring the density, concentration, deposition, organization, and/or localization of collagen in a region having enhanced collagen signal, the concentration of collagen fibers having a taut configuration, the extent of tautness of collagen fibers, the degree of enhanced radial alignment, the proximity of taut and/or radially aligned collagen fibers to a tumor or precancerous tissue or any combination of these parameters so as to assess the state, composition, physical properties and invasiveness of cancerous or precancerous tissues in the test sample. Methods of the present invention optionally include the step of correlating the presence and extent of two or more tumor-associated collagen signatures identified in a test image or test data to provide enhanced diagnostic information.

In an embodiment, several distinct signatures are described wherein a given tumor-associated collagen signature is characterized by an individual attribute, e.g., the presence, prevalence, amount, rate of change or physical feature of a structure, other attribute, or by a combination of attributes. In an embodiment, tumor-associated signatures are derived from images and/or image data of animal tissue, such as human tissue. In an embodiment, tumor-associated collagen signatures are derived from images and/or image data of breast tissue or epithelial tissue. In a particular embodiment, several tumor associated signatures are derived from a mouse mammary tumor model of disease but can serve as a tool in human or other mammalian clinical diagnosis or other predictive correlation of a health or disease state in the clinical or research context. In a particular example, a tumor associated signature is identified and/or assessed from a nonlinear microscopic imaging technique or combination of nonlinear microscopic imaging techniques, such as mulitphoton microscopy and harmonic generation microscopy (e.g., second, third, fourth etc.).

In another aspect, the invention provides a method of diagnosing breast cancer with an improved accuracy, precision, and/or timing relative to a conventional breast cancer screening and/or diagnostic techniques. In an embodiment, the improved timing relates to an ability to detect cancer or a suspected cancer condition at an early stage of development.

Methods of the present invention may be used to evaluate the presence, qualitative stage and/or quantitative measurement of cancer and conditions of a wide range of biological materials, such as tissue, tissue samples, or tissue extractions. The present methods and systems are useful for evaluating tissue for the diagnosis of cancer, including excised tissue, such as tissue generated via surgical biopsy, and tissue in whole organisms, for example using endoscopic microscopy techniques. The present methods and systems are applicable in the context of veterinary and medical research applications in evaluating animal cancers and animal models of cancer. In an embodiment, methods and systems of the invention are used in the context of assessing a tissue sample in situ; depending on the assessment, a decision to further analyze by obtaining a biopsy sample can allow further opportunity to employ methods and systems of the invention in connection with the biopsy sample, optionally in conjunction with conventional tissue analysis techniques. In a preferred embodiment, methods and systems of the invention are used to support strategic surgical decisions in real time, whether based on in situ tissue or biopsy tissue samples.

In embodiments of the present invention, analysis of images to identify and characterize tumor-associated signatures may be carried out by a doctor, other healthcare professional, researcher, a computer or computer processor, or any combination of these. In one embodiment providing a partially or fully automated method, identification of tumor-associated collagen signatures is carried out via a computer-based technique employing pattern recognition analysis of one or more images of the test tissue, for example by using a wavelet analysis, a curvelet analysis, segmentation algorithm, machine learning algorithm, artificial neural network, geometric modeling, fuzzy clustering, spatial filtering, gray level thresholding, surface mapping, 3D rendering, and/or statistical tools. For example, a pattern of imaging data may be used to correlate one or more tumor-associated collagen signatures, or pattern thereof, with a particular structure, wherein such pattern or correlation can employ computer-based techniques to determine whether the particular structure is present in the tissue or to quantify the degree or extent of one or more tumor-associated collagen signatures in the image or image data. While it is preferred for some applications of the present invention that a computer be used to accomplish all the steps of the present methods with final clinical staff oversight, it is contemplated that a computer may be used to perform only a certain step or selected series of steps in the present methods. The present invention includes partial and fully automated methods for diagnosing cancer in tissues.

In another aspect, the present invention provides a method of diagnosing a cancerous condition, comprising the steps of: (i) detecting a substantial reorganization of mammary stroma; and (ii) associating the substantial reorganization of mammary stroma with a cancerous condition, thereby diagnosing breast cancer.

In another aspect, the present invention provides a method of assessing a breast cancer risk potential, comprising providing a breast tissue sample, evaluating one or more stromal collagen parameters, and correlating the one or more stromal collagen parameters with a probability of breast cancer; thereby assessing said breast cancer risk potential.

In another aspect, the present invention provides a method of locating a tissue region associated with a cancer risk. In one embodiment, a method of the present invention comprises the steps of providing a tissue sample, examining the tissue sample by employing a nonlinear microscopy technique, identifying a tumor-associated collagen signature profile in the tissue sample from an output of the nonlinear microscopy technique, and spatially resolving the tumor-associated collagen signature profile with respect to the corresponding tissue sample or a three-dimensional representation of the tissue sample; thereby locating said tissue region associated with said cancer risk. Methods of this aspect of the present invention are useful for analyzing tissue generated by surgical biopsy or analyzing tissue in a whole organism, for example using endoscopic microscopy methods. Optionally, methods of this aspect of the present invention further comprise the step of defining a tissue region margin, wherein the margin is proximal to a first region of suspect tissue and a second region of normal tissue. Optionally, methods of this aspect of the present invention further comprise the step of identifying a candidate tissue removal region.

In another aspect, the present invention provides a method for diagnosing a cancerous condition, comprising the steps of: (i) detecting a substantial reorganization of mammary stroma; and (ii) associating the substantial reorganization of mammary stroma with a cancerous condition, thereby diagnosing the cancerous condition.

In another aspect, the present invention provides a method for assessing a breast cancer risk potential, comprising the steps of: (i) providing a breast tissue sample, (ii) generating am image of the sample, (iii) evaluating the image by identifying a tumor-associated collagen signature profile for the image, and (iv) correlating the tumor-associated collagen signature profile with a probability of breast cancer; thereby assessing the breast cancer risk potential.

In another aspect, the present invention provides tumor-associated collagen signatures observable in images generated by nonlinear optical microscopy techniques such as MP microscopy and harmonic generation (second, third etc.) microscopy. Tumor-associated collagen signatures in images of test tissue, such as breast tissue, provide information relevant to the diagnosis and treatment of cancer, such as the presence and/or abundance of tumors or precancerous tissue, the rate of progression of cancer, the composition of tumors or precancerous tissue, the type and virulence of cancer in test tissue, and the effect of a therapy on treating cancer in a subject.

In another aspect, the present invention provides a system for evaluating a test tissue sample for the diagnosis of cancer, comprising: (i) a nonlinear optical imaging device for generating a test image or test imaging data from the test tissue sample using a nonlinear optical imaging technique; and (ii) a processor for analyzing the test image or test imaging data of the test tissue sample, the processor using a pattern recognition algorithm for analyzing the test image or test imaging data for detection of at least one tumor-associated collagen signature, thereby evaluating the test tissue sample for the diagnosis of cancer. In an embodiment, the nonlinear microscopy technique of this system is multiphoton laser-scanning microscopy, second harmonic generation, third harmonic generation or any combination of these, for example, a combination of multiphoton laser-scanning microscopy and second harmonic generation.

The system of this aspect of the present invention may be partially automated system or a fully automated system. Processors of some embodiments utilize a pattern recognition algorithm that analyzes the test image or test imaging data using a curvelet or wavelet analysis. Processors of this aspect of the present invention may optionally, (i) store or archive output data comprising tumor-associated collagen signature data (e.g., characterization of one or more tumor-associated collagen signatures identified in the image or image data); (ii) display (e.g., to a screen) output data comprising tumor-associated collagen signature data; (iii) provide output data comprising tumor-associated collagen signature data to a user; or any combination of these. In an embodiment, the pattern recognition algorithm of the processor compares the test image or test imaging data with a reference image or reference imaging data.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
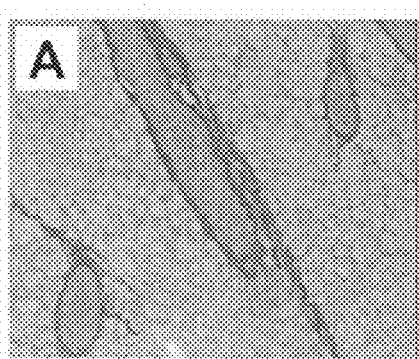
FIG. 1 provides images illustrating Collagen morphology and the epithelial-stromal interaction in the mammary gland. (A) Picrosirius red staining (red), a selective collagen stain, indicating the primary stromal component is collagen. (B) TEM image of a mouse mammary duct (transverse section) showing the organization of epithelial (e) and myoepithelial (me) cells outside the lumen (L) in close association with the collagenous stroma (s). (C) SEM image of the ductal end. (D) SEM image of collagen fibers interacting with ductal epithelial cells. (E) SEM image of collagen bundles wrapping around the cell in multiple directions. (F) Validation of fibrillar collagen composing epithelial interacting collagen fibers. (G) SEM image of collagen fibrils immediately adjacent to the cell surface. (H) TEM image of collagen fibrils (col) directly next to the epithelial cell (e).
Figure 1:
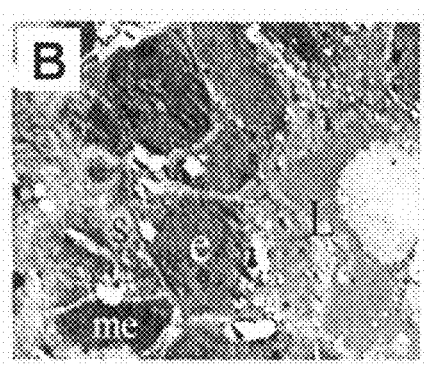
Figure 1:
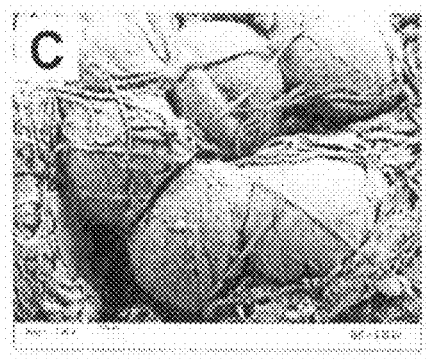
Figure 1:
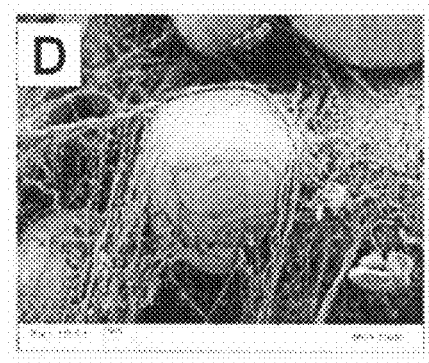
Figure 1:
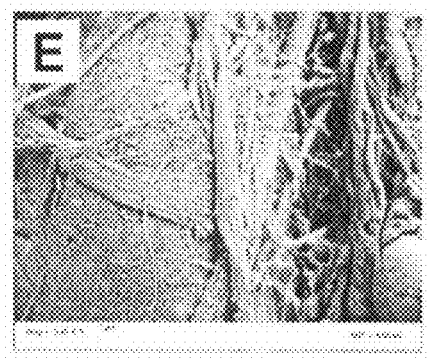
Figure 1:
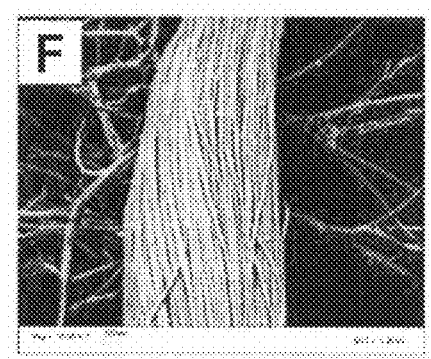
Figure 1:
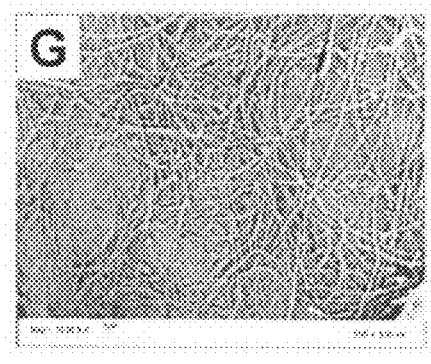
Figure 1:
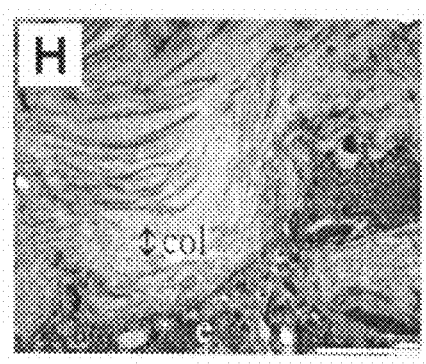

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

In the context of this description, the term "nonlinear" refers to photonic processes, such as fluorescence excitation or SHG scattering, that exhibit a rate that depends nonlinearly on the intensity of incident electromagnetic radiation. Nonlinear optical imaging methods useful in the present invention include, but are not limited to, MP microscopy (two photon excitation, three photon excitation, etc.) and harmonic generation microscopy (second harmonic generation, third harmonic generation, fourth harmonic generation, etc.).

When used herein, the term "tissue sample" can refer to a portion of tissue from an animal subject. The sample can be intact and in situ, for example as part of a tissue or organ while remaining attached to the living animal. Alternatively, the sample can be an excised tissue portion which can optionally be further processed. In an embodiment, the excised sample is fixed. In an embodiment, the excised sample is stained, e.g., using conventional histopathology techniques. In an embodiment, the excised sample is frozen. In a particular embodiment, the sample is a mammalian breast tissue sample or epithelial tissue sample. In a preferred embodiment, the sample is a live or excised breast tissue portion which is structurally intact (e.g., unsectioned), unfixed, and unstained.

When used herein, the term "test tissue sample" generally refers to a tissue sample from a subject where a condition of the sample or the subject is unknown or suspected and it is desired to ascertain such condition. For example, a test tissue sample can be a breast sample from which a breast cancer diagnosis is to be determined.

When used herein, the term "reference tissue sample" generally refers to a tissue sample for which a condition has been ascertained. For example, the reference could correspond to a sample having a known positive condition or a known negative condition, or a stage of a disease or normal physiological process, thus serving as a control or point of comparison in the evaluation of a different sample.

When used herein, the term "reference level" indicates a level that has been assessed and serves as a point of comparison relative to a test level. For example, a reference level can be an amount or qualitative state as seen in a normal condition, a diseased condition, or as seen in a point along a continuum of conditions.

When used herein, the term "diagnosis" and other root word derivatives are as understood in the art and are further intended to include a general monitoring, characterizing and/or identifying a state of health or disease. The term is meant to encompass the concept of prognosis. For example, the diagnosis of breast cancer can include an initial determination and/or one or more subsequent assessments regardless of the outcome of a previous finding. The term does not necessarily imply a defined level of certainty regarding the prediction of a particular status or outcome.

When used herein, the term "cancerous" is as generally understood in the art. For example, the term can refer to a clinical condition of an unregulated or misregulated cell or tumor wherein there is an abnormal ability to proliferate, differentiate, and or migrate. The term is intended to address a variety of stages of disease progression. Thus the term precancerous is envisioned as encompassed within the conceptual scope whether viewed as a distinct earlier stage with a different potential and/or different level of disease significance relative to cancerous or viewed as part of a connected pathway or continuum. In a particular example, a cancerous condition can include having a prepalpable breast mass, wherein the mass is a tumor or suspected tumor.

When used herein, the term "intact" refers to material that has generally not been substantially disrupted. For example, the term can indicate a tissue sample that has not been sectioned.

When used herein, the term "in situ" refers to material that is in the natural or original position or place. For example, a breast tissue sample can be examined, relatively non-invasively, by imaging the sample while it remains in the breast.

When used herein, the term "excised" refers to material that has been removed from its natural location. For example, a breast tissue biopsy specimen is excised to facilitate its examination.

The present invention provides methods and systems for evaluating biological materials for the diagnosis of disease, such as gland abnormalities, and the cancerous and precancerous conditions. Nonlinear optical microscopy techniques, such as MP microscopy and harmonic generation microscopy, are used to generate high resolution, three dimensional images of a test tissue, such as a biopsy tissue sample and tissue in whole organisms, that are analyzed, optionally in combination, to detect, identify and characterize tumor-associated collagen signatures. The presence, abundance and extent of histological features and structural motifs comprising tumor-associated collagen signatures may be directly and accurately correlated with the onset and progression of cancer, such as breast cancer. The present methods are capable of providing an accurate and selective diagnosis of cancer, and provide diagnostic information complementary to conventional diagnostic methods.

Human breast carcinoma is frequently associated with increased deposition of proteins found in the extracellular matrix, especially collagen. However, the identification of specific collagenous structures is not currently exploited to help detect human breast carcinoma.

The present methods and systems use a combination of multiphoton microscopy (MPM) and second harmonic generation (SHG) imaging to evaluate collagen structures in unfixed, unstained tissue. Three-dimensional in situ imaging of tumors in tissue samples reveals a plurality of tumor-associated collagen signatures that provide novel hallmarks for locating and characterizing tumors. In particular, three tumor-associated collagen signatures are particularly useful for the diagnosis and treatment of breast cancer: (i) increased collagen deposition, concentration, density and localization before tumors are palpable, (ii) realignment of collagen fibers with increased taut fibers, and (iii) local cell invasion along aligned fibers. These three tumor-associated collagen signatures provide reliable indicators for identifying and characterizing breast tumors in animal models and human tissues.

In the present invention, advanced nonlinear imaging techniques are used to characterize selected surface and subsurface regions or layers of a test tissue so as to identify and characterize tumor-associated collagen signatures useful as diagnostic tools. Advanced multiphoton imaging techniques, such as MP microscopy, SHG and combined spectral/lifetime signal detection, provide a sensitive and selective means of identifying tumor-associated collagen signatures having diagnostic value, and correlating tumor-associated collagen signatures with specific types and stages of cancerous and precancerous conditions. The present noninvasive and non-destructive imaging methods and systems are also capable of rapidly characterizing a test tissue, thus providing an optical imaging tool that generates real time information useful for therapeutic applications, including surgical therapies. Nonlinear optical imaging in the present invention may be carried out for the in situ and in vivo evaluation of excised tissue and tissue in whole organisms.

The invention is further described by the following non-limiting Examples.

EXAMPLE 1

Collagen Reorganization at the Tumor-Stromal Interface Facilitates Local Invasion I. Abstract Stromal-epithelial interactions are of particular significance in breast tissue since misregulation of these interactions can promote tumorigenesis and invasion. Moreover, collagen-dense breast tissue increases the risk of breast carcinoma, although the relationship between collagen density and tumorigenesis is not well understood. As little is known about epithelial-stromal interactions in vivo, it is necessary to visualize the stroma surrounding normal epithelium and mammary tumors in intact tissues to better understand how matrix organization, density, and composition affect tumor formation and progression. In this example, we use both laser-scanning multiphoton and second harmonic microscopy to determine the organization of specific collagen structures around ducts and tumors in intact, unfixed and unsectioned mammary glands. Local alterations in collagen density are clearly seen, allowing us to obtain three-dimensional information regarding the organization of the mammary stroma, such as radiating collagen fibers that cannot be obtained using classical histological techniques. Moreover, we observed and defined three "Tumor-Associated Collagen Signatures" (TACS) that provide novel hallmarks to locate and characterize tumors. In particular, local cell invasion is found predominantly oriented along certain aligned collagen fibers, suggesting that radial alignment of collagen fibers relative to tumors facilitates invasion. Moreover, the presentation of these collagen signatures provide indications that a tumor could become invasive, and may serve therefore as a strategy to help identify and characterize breast tumors in animal and human tissues.

II. Introduction

Tissue microenvironments play an important role in maintaining normal cell behavior. Moreover, type I collagen is an important regulator of mammary ductal formation during development. Decreasing the levels of $\alpha_2\beta_1$ integrin, a primary type I collagen receptor, disrupts mammary epithelial tubulogenesis in vitro and alters branching morphogenesis in vivo, respectively. Furthermore, inappropriate stromal-epithelial interactions can promote tumorigenesis, and in breast cancer, metastatic epithelial cells migrate in direct contact along stromal collagen fibers. The importance of studying stromal interactions in breast tissue is further reinforced by the fact that patients with collagen-dense breast tissue possess a greater than four-fold increased risk of breast carcinoma. Although the mechanisms mediating the effects of the extracellular matrix (ECM) on breast carcinoma development in vivo are largely unknown, contributing factors may be adhesion mediated signaling and mechanical signals imparted on mammary epithelial cells from surrounding type-I collagen-rich stroma, either directly or across basement membrane proteins. One important step to elucidating these signaling interactions is to determine the organization of the stroma surrounding both normal mammary glands and tumors within intact tissue so as to better understand the cell-matrix interaction and how matrix organization, density, and composition affect tumor formation and progression.

Nonlinear microscopy techniques such as multiphoton laser-scanning microscopy (MPLSM) and second harmonic generation (SHG) provide powerful tools to image extracellular matrix structure in intact tissues. Both techniques are well suited for high-resolution in vivo imaging. Specifically, multiphoton microscopy results from the nonlinear excitation of molecular fluorescence and can produce images deep into thick tissues while SHG signals depends on non-linear interactions of illumination with a non-centrosymmetric environment (e.g. fibrillar collagen) that can provide submicron resolution. The most commonly utilized multiphoton process is two-photon fluorescence excitation (2 PFE) of fluorescence, in which two low-energy (usually near-infrared) photons simultaneously excite a fluorophore, which later decays to produce a single fluorescent photon of higher energy; fluorescence is dependent upon the square of the intensity. SHG imaging, on the other hand, does not arise from an absorptive process, but instead the laser field suffers a nonlinear, second-order, polarization when passing through certain ordered structures resulting in a coherent signal at exactly half the wavelength of the excitation. Great utility arises from the fact that MPLSM and SHG can be implemented simultaneously to provide complementary information and a powerful experimental and diagnostic tool.

The purpose of the present example is to characterize collagen morphology in intact tissues so as to understand the structure-function relationship of normal and tumor stromal interactions in the mammary gland. We used both MPLSM and SHG imaging, in conjunction with additional correlative microscopy techniques, and detected differences in local collagen density that possessed distinct collagen fiber organization around normal glands and tumors, with characteristic collagen structures associated with tumor-cell invasion.

III. Materials and Methods

Mouse Mammary Tissues and Tumors: To study non-tumor bearing mammary glands, tissue was obtained from B6129SF2/J mice or Col1a1tmJae mice (The Jackson Laboratory). To study tumor-stromal interactions in intact tissue two mouse breast tumor models were utilized: Wnt-1 and polyoma middle T (PyVT).

Tumor Explants and Collagen Gel Culture: To study tumor-mediated collagen reorganization and tumor cell invasion in vitro, small tumors or small pieces of tumor from PyVT mice were cultured in type I collagen gels. Tumors were harvested and surrounding connective tissue removed. Following removal of surrounding mammary tissue and stroma, tumors were rinsed in DMEM containing penicillin/streptomycin/fungizone solution (Cellgro). A single tumor explant was then cultured within a 2.0 mg/mL collagen gel (8.0 mg/mL rat-tail collagen solution (BD Biosciences) neutralized with 100 mM HEPES in 2×PBS). Following Gel polymerization for 1 hour, the tumor explant containing collagen gels were released from the culture dish and floated in DMEM containing penicillin/streptomycin solution supplemented with 10% heat inactivated FBS.

Multiphoton Microscopy and Second Harmonic Generation: For MPLSM and SHG imaging of live unfixed, intact (not sectioned), non-stained glands, tumor explants within collagen gels, or hematoxylin and eosin stained slides we used an optical workstation. Second harmonic generation was detected from the back-scattered SHG signal. The excitation source was a Ti:sapphire laser (Spectra-Physics-Millennium/Tsunami) producing around 100 fs pulse widths and tuned to 890 nm. The beam was focused onto the sample with either a Nikon 40× Plan Fluor oil-immersion lens (N.A.=1.4) or a Nikon 60× Plan Apo water-immersion lens (N.A.=1.2). For 3D imaging in intact tissues, 2D (x-y) images were acquired at various serial depths (z) into the samples. Image analysis was performed with Imagej and VisBio software.

Histology and Electron Microscopy: For histology, formalin fixed paraffin embedded samples were sectioned and stained for hematoxylin and eosin, Trichrome, and picrosirius red using standard techniques. Sample preparation for scanning electron microscopy (SEM) was performed by fixing whole mammary glands in 2.5% formaldehyde/2.5% glutaraldehyde in 0.1M sodium cacodylate buffer for 1 hr at room temperature (RT), after which sample were placed in fresh fixative overnight at 4° C. Samples were then washed in cacodylate buffer and postfixed in 1.5% osmium tetroxide at RT for 1.5 hrs. Samples were again washed in buffered solution and dehydrated, critical point dried, sputter coated, and imaged with SEM, or stained, dehydrated and cleared, embedded, and then sectioned for imaging with TEM.

IV. Results

The Normal Mammary Gland

Figure 2:
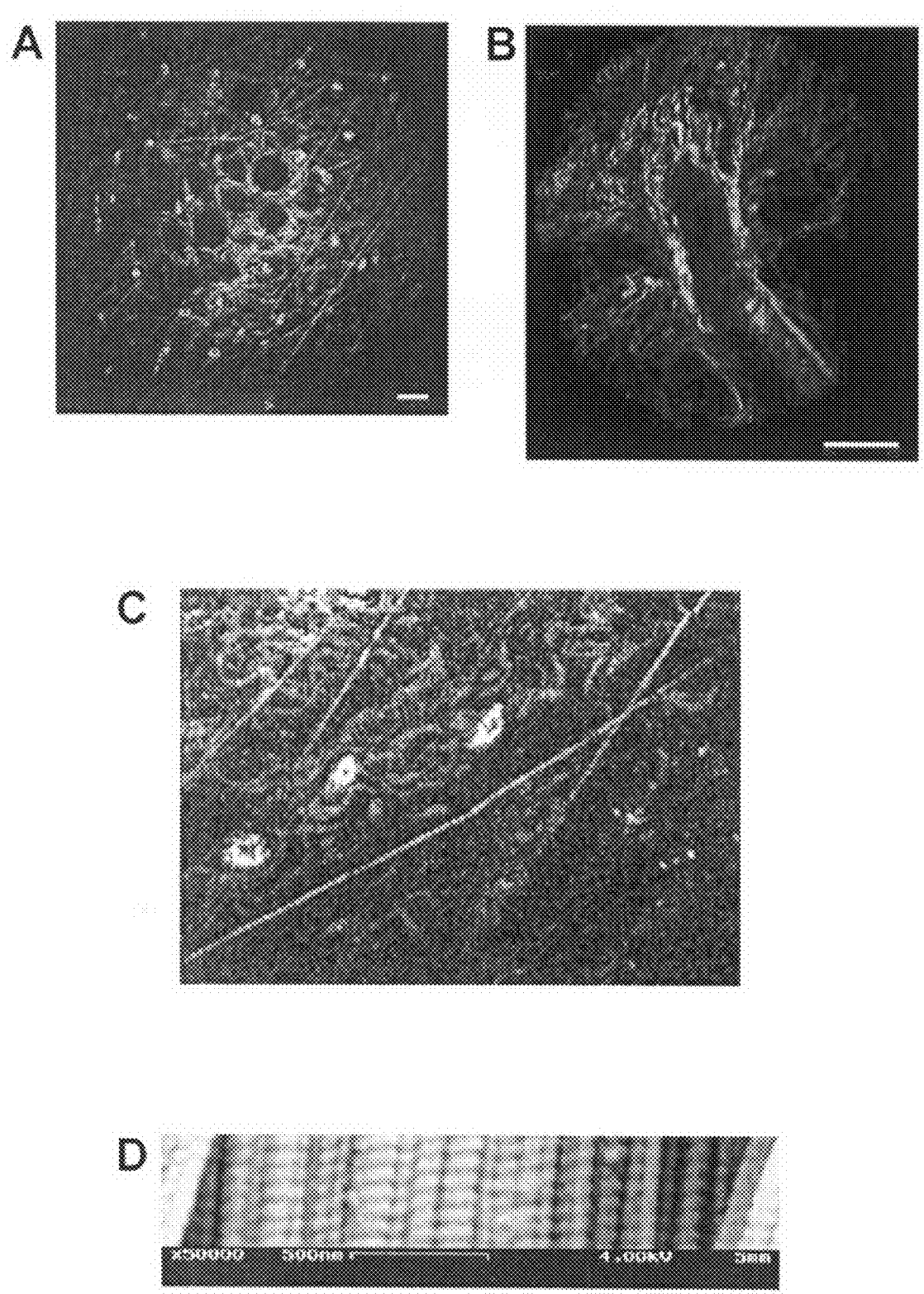
FIG. 2 provides MP laser scanning micrography (MPLSM) and SHG images of living mammary gland. (A) MP/SHG image at the "top" of the, mammary duct showing both wavy and taut collagen structures as well as endogenous fluorescence from stromal cells (most likely fibroblasts and immune cells). (B) MP/SHG image of a mammary duct demonstrating collagen wrapped around the duct as well as radiating out from the duct. (C) Enlarged section from (A) showing some aspects of collagen fibril structure that resemble the standard banding pattern seen in collagen fibrils from connective tissue (D: mouse tendon). (E) Correlative SEM image of collagen surrounding ductal epithelial cells showing both wavy and taut fibers as obtained with MP/SHG imaging. (F) MP/SHG image of the region near the nipple in tissue demonstrating straightened collagen radiating from the acinus-like structure. (G) MP/SHG image "above" the mammary duct showing both wavy and taut fiber structures. Note: All MP/SHG images are from live intact tissues that are not fixed, sectioned, or stained; scale bar for MP/SHG images equals 25 µm.
Figure 2:
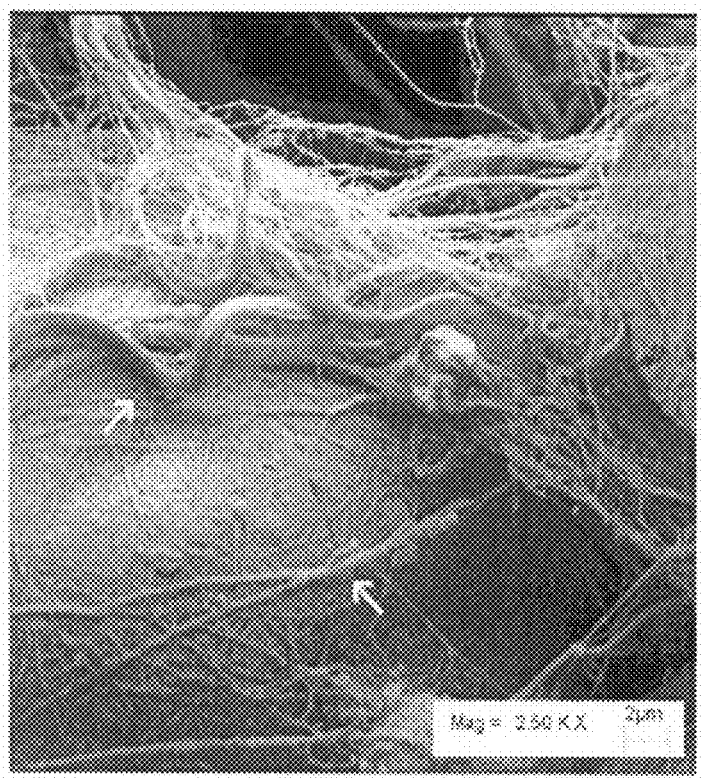
Figure 2:
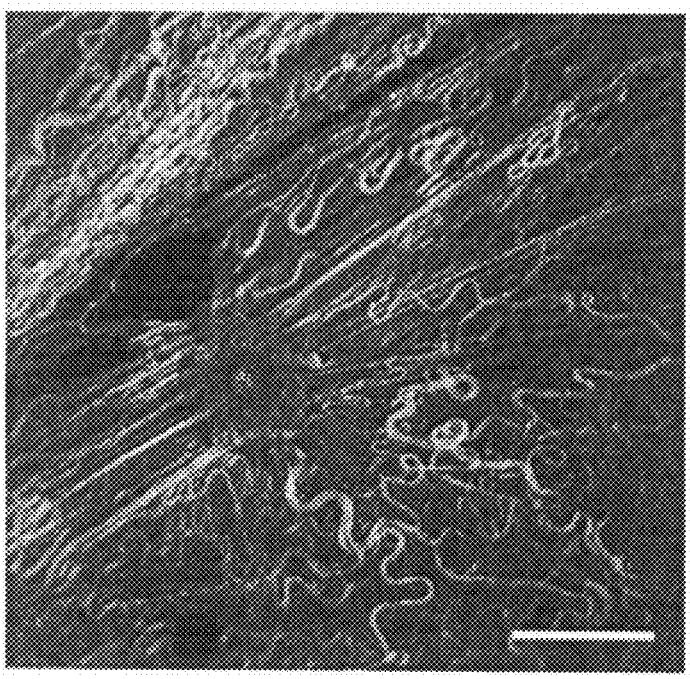
Figure 2:
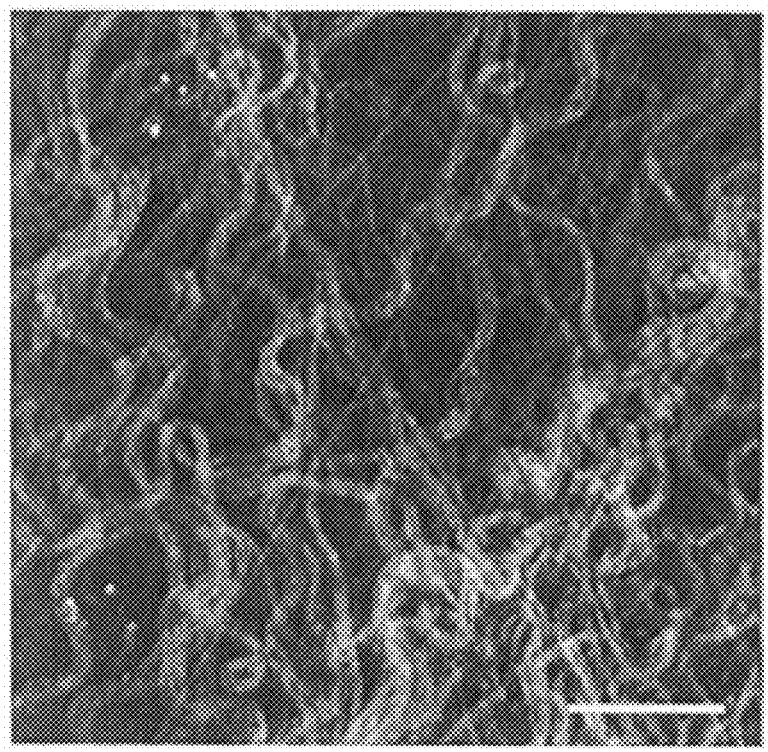

Examination of the ECM surrounding mammary epithelial cells revealed that the majority of the stroma is fibrillar collagen, which was seen in close association with the epithelial cell (See, FIG. 1). Although it has been assumed that epithelial cells do not contact collagen due to the basement membrane and myoepithelial cells, we found fibrillar collagen in close association with some epithelial cells (See, FIG. 1B). Observations at high magnification with SEM showed collagen fibers wrapping around the ductal structure in an organized manner surrounding the epithelial cells (See, FIG. 1C), in a fashion similar to that seen in FIG. 1A. Additionally, collagen can be seen wrapping individual cells in multiple directions (See, FIGS. 1C, D, E), suggesting a role for collagen as a containing and anchoring structure. Of further importance, higher magnification images with both SEM (See, FIGS. 1F and G) and TEM (See, FIG. 1H) confirmed that the collagen fibers are composed of fibrillar collagen (See, FIG. 1F; as indicated by their rod-like structure and presence of the ~67 nm banding pattern FIG. 2D (24)) that are immediately adjacent to the epithelial cells (See, FIGS. 1G and H). These data, in combination with published works indicating an important interaction between collagen and the epithelial cell, imply that collagen fibrils are likely to be either bound directly to the epithelial cell or that these fibers apply physical restraint and mechanical signals across a thin basement membrane (<200 nm) that may not completely cover the epithelial cell; or most likely a combination of both scenarios.

Figure 5:
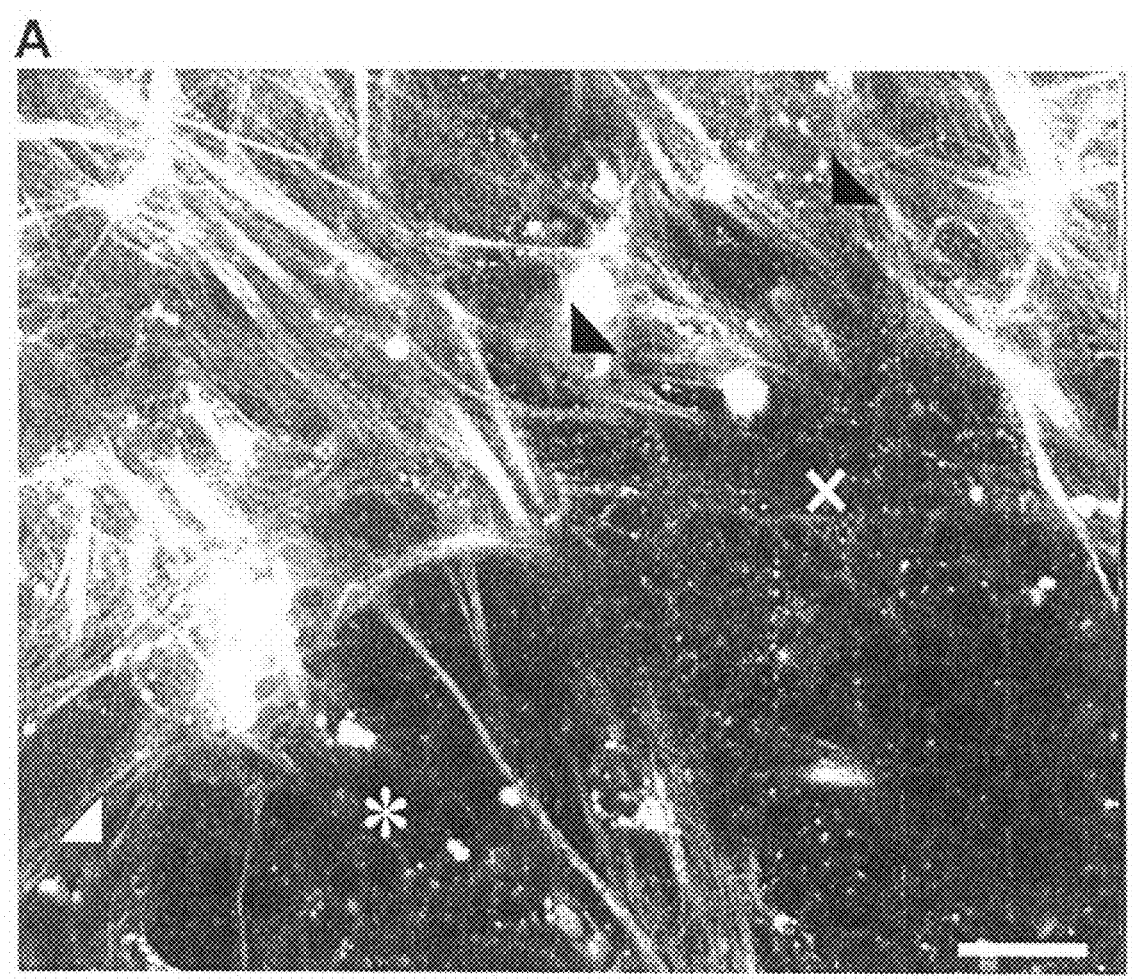
FIG. 5 provides images illustrating radially aligned collagen fibers associated with invasion. Combined MP/SHG imaging of live intact mammary tumors indicates that (A) noninvading regions (*) possess taut collagen (TACS-2; white arrowhead) wrapped around the tumor, while regions of invasion (x) are linked to aligned collagen, with cells invading along radially aligned collagen fibers (TACS-3; black arrowheads). Examination of invasion at the tumor-stromal interface at higher magnification (B and C) clearly reveals the collagen alignment at specific regions of invasion (B) with tumor cells (*) in between, and in association with, aligned collagen fibers (C). Scale bar equals 25 µm.
Figure 5:
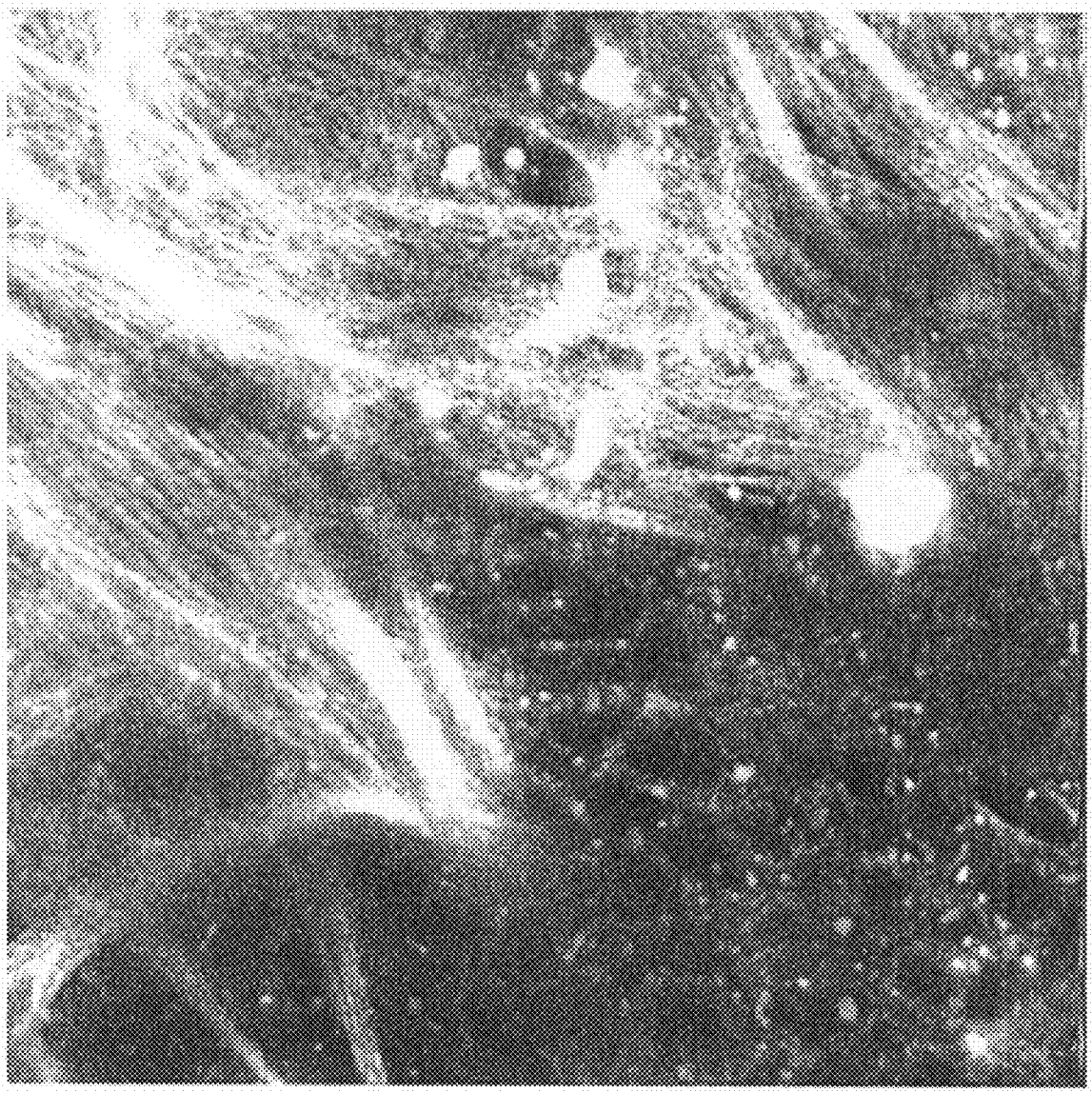
Figure 5:
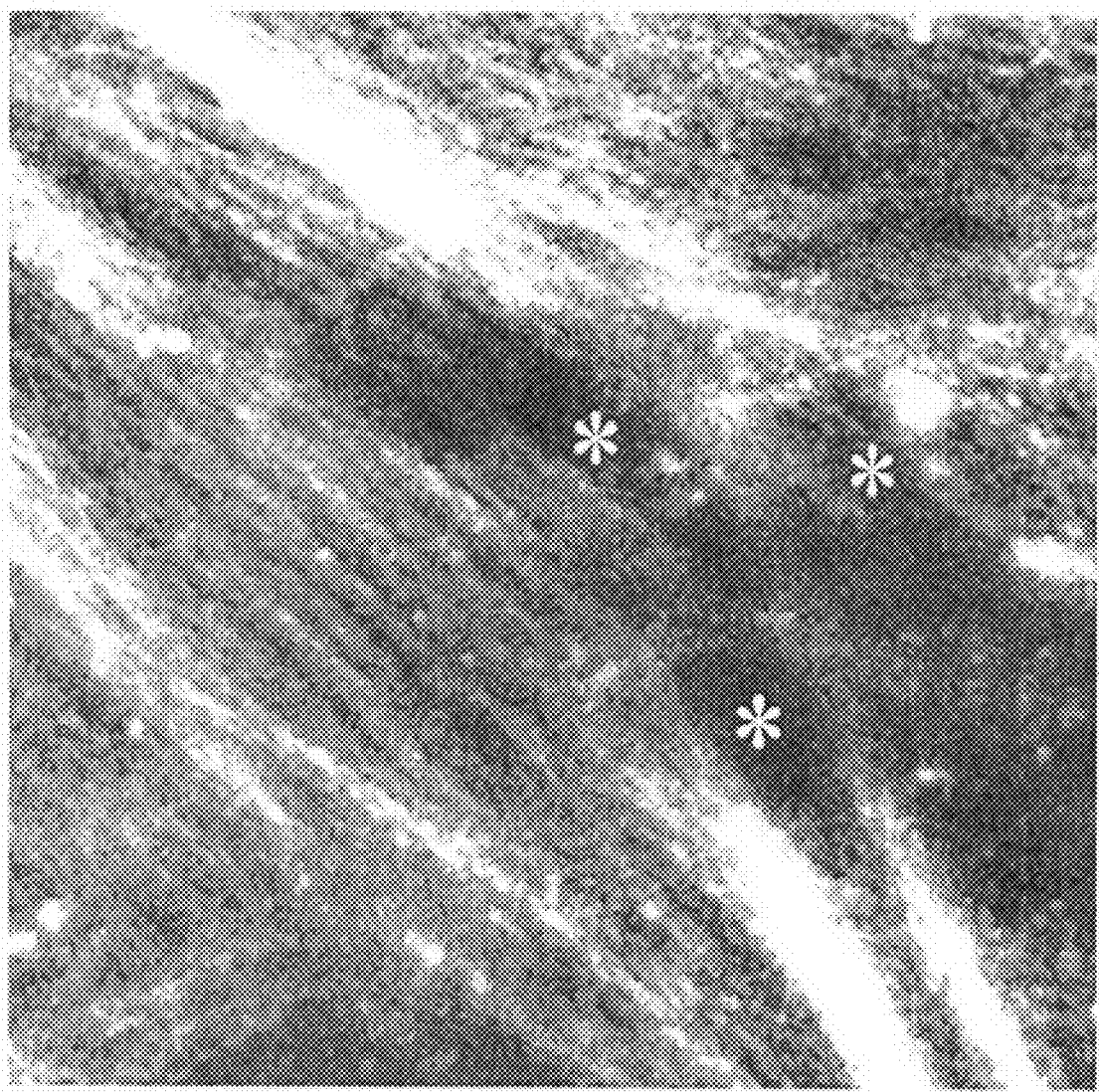

Although histology and electron microscopy provide valuable and detailed information regarding the composition and morphology of the epithelial-stromal interaction, these techniques are destructive to the sample and the capability for three-dimensional imaging is limited. Therefore, we have developed nondestructive imaging techniques (e.g. MPLSM/SHG) that allow imaging in four-dimensions (x, y, z, and time. Combined MPLSM-SHG produced clear images of collagen (See, FIG. 5) as well as endogenous fluorophores such as NAD(H) (See, FIG. 5C) in intact non-treated tissues. Application of MPLSM/SHG to intact, non-fixed, non-stained mammary gland captured the morphology of the fibrous stroma seen in FIG. 1. For instance, images captured "above" the gland (See, FIG. 2A, G) clearly showed the presence of wavy (crimped) collagen as well as the presence of taut fibril bundles (See, FIG. 2A, E, F, G) showing a periodicity of ~250 nm (See, FIG. 2C), consistent with previous reports for SHG resolution, which may indicate a four-fold super-periodicity of the basic ~67 nm banding pattern of collagen fibrils (See, FIG. 2D). Additionally, collagen was noted wrapping around the epithelial duct (consistent with FIGS. 1A and C), as well as radiating away from the duct (See, FIG. 2B).

Detecting Dense Mammary Tissue

Figure 3:
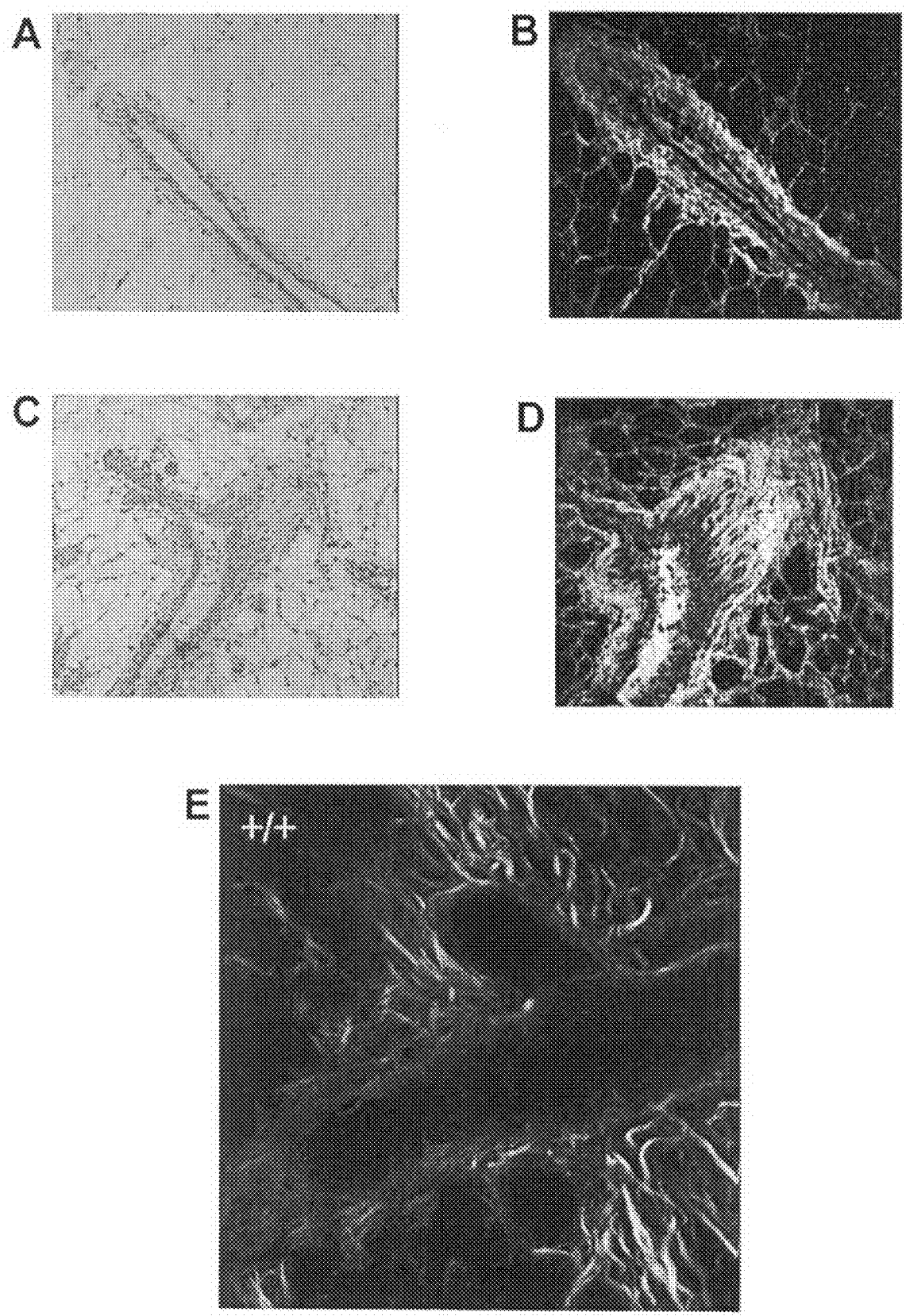
FIG. 3 provides MPLSM/SHG images for detection of increased collagen density in the mammary gland. (A) H&E stain of wild-type control mammary gland. (B) MP image of (A) showing increased visualization of collagen structure. (C) H&E stain of mammary gland from a col/col homozygote mice. (D) MP image of (C) showing increased visualization of collagen density and structure and the epithelial-stromal interaction, particularly the invasive morphology associated with increased collagen. (E-G) MPLSM/SHG image mammary ducts that are not fixed, sectioned, or stained from wild-type (E), heterozygous (E), and homozygous col1a1 mice, showing increased collagen density in transgenic animals. (H) 340 µm (typical depth capability 350-440 µm) z-stack of (F) illustrating the structure of the glands and their relative location in the gland. Note: scale bar for MP/SHG images equals 25 µm.
Figure 3:
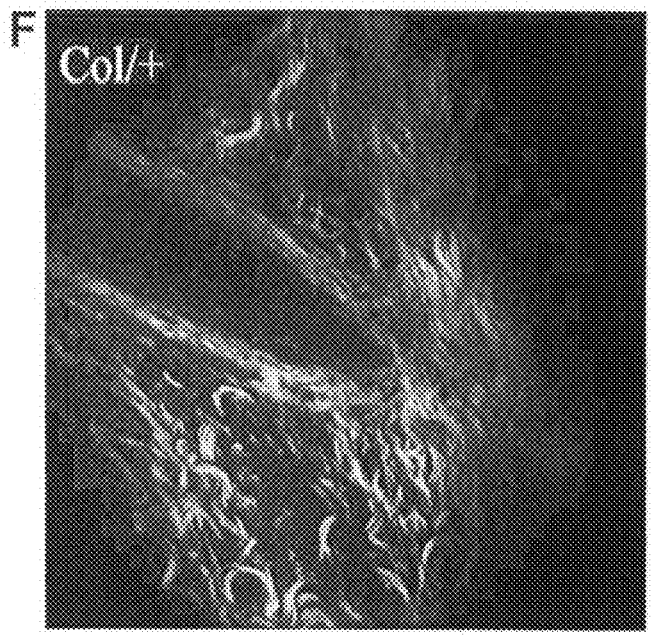
Figure 3:
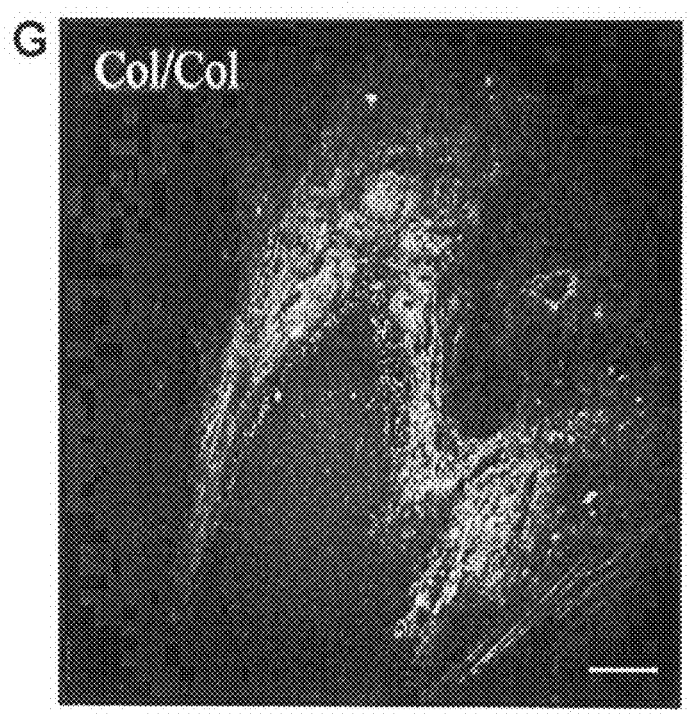
Figure 3:
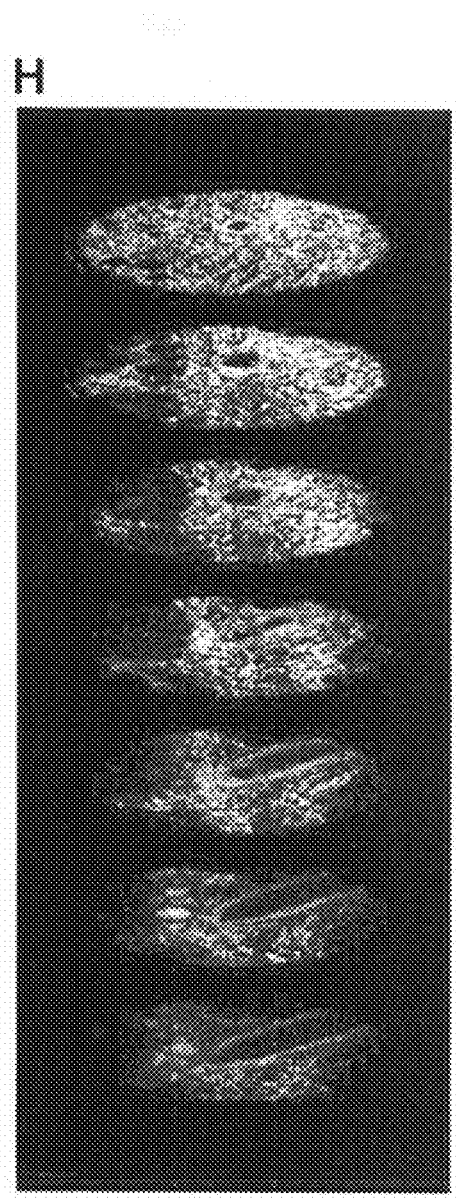
Figure 6:
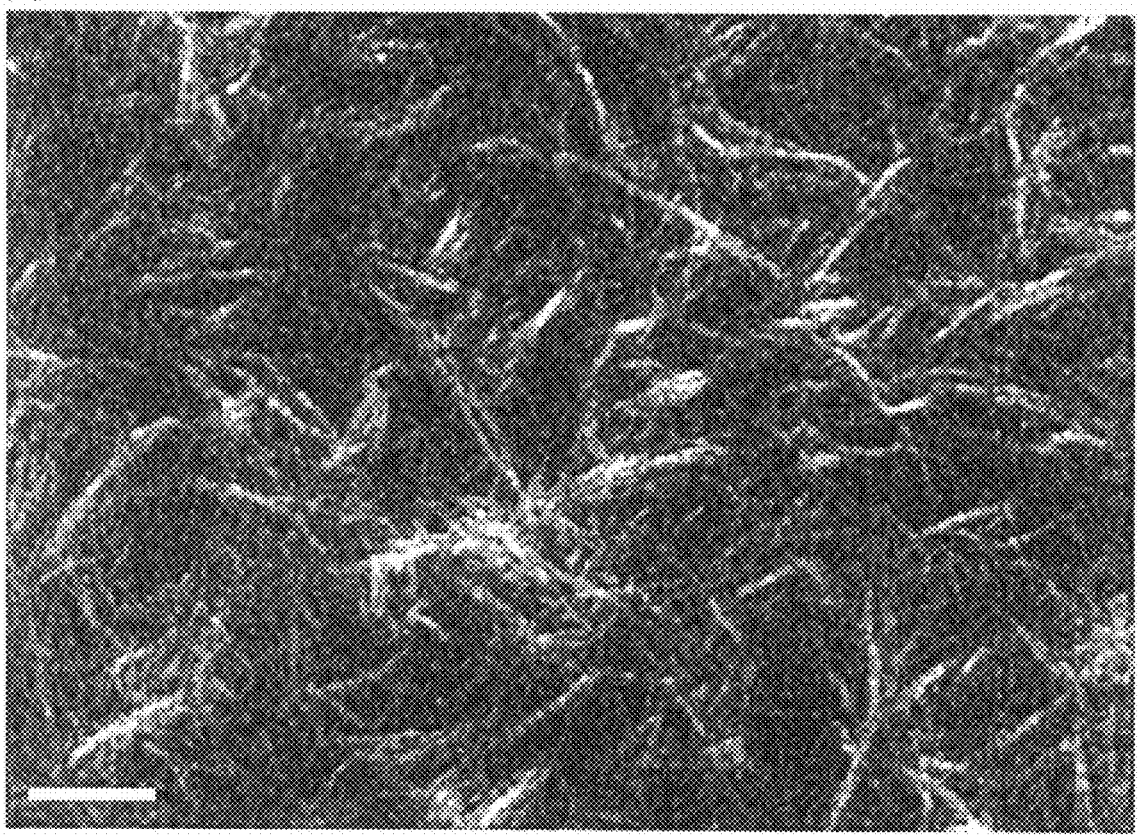
FIG. 6 provides images showing Collagen matrix reorganization by tumor cells facilitates local invasion of tumor cells. Combined MP/SHG imaging of tumor explants cultured within 3D collagen gels for eight hours demonstrates that tumor cells reorganize a previously random matrix to facilitate invasion. (A) Region of 3D collagen gel remote from the tumor demonstrating the random orientation of collagen present within 3D collagen gels unless organized or reorganized by a specific outside force. This random organization is specifically altered by cells from tumor explants as the cells contract and reorganize the collagen matrix. Similar to in vivo data in live intact tissues, non-invading regions show collagen pulled in near the explant but wrapped around the tumor boundary (B), while at regions of tumor cell invasion into the collagen gel, collagen has been radially aligned by the tumor cells (C) with cells (*) in direct contact with the collagen matrix (white arrowheads; D). Therefore, at regions of tumor cell invasion, collagen has been reorganized to a radial alignment from a random orientation, indicating a structural realignment of collagen fibers facilitates local invasion. Scale bar equals 25 µm.
Figure 6:
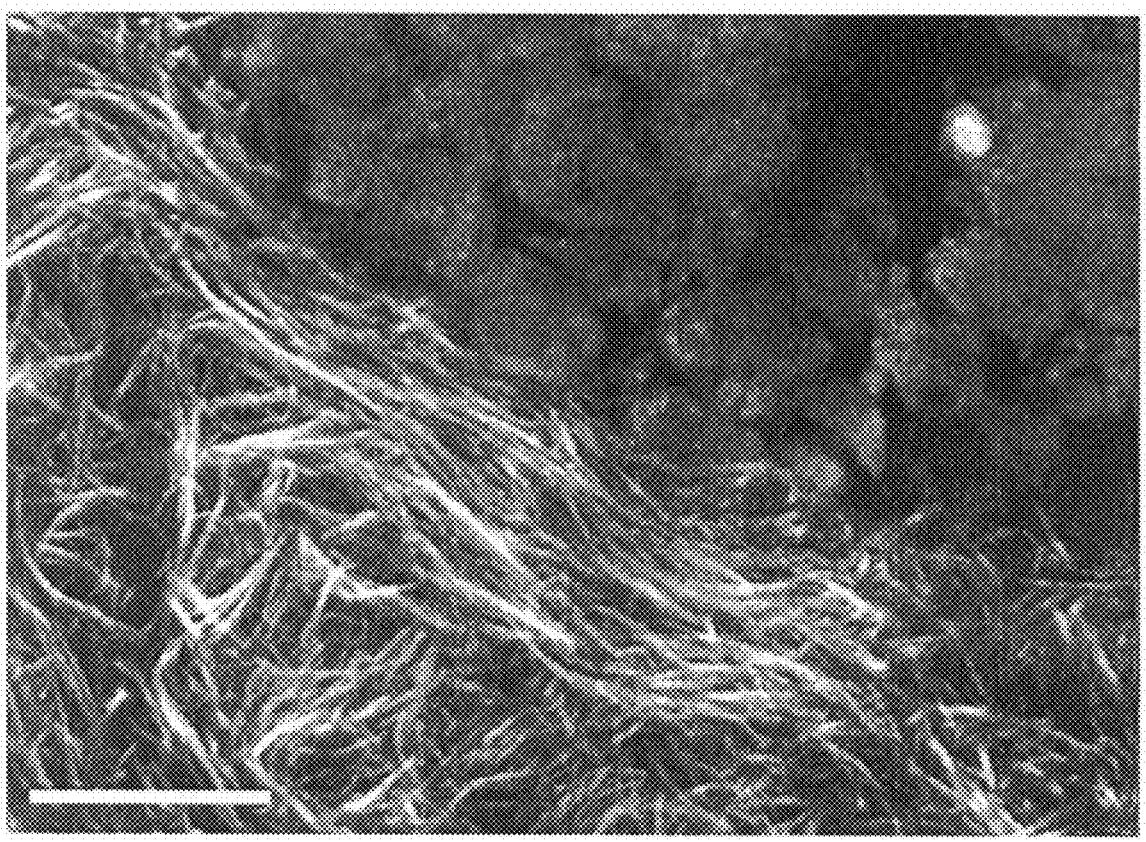
Figure 6:
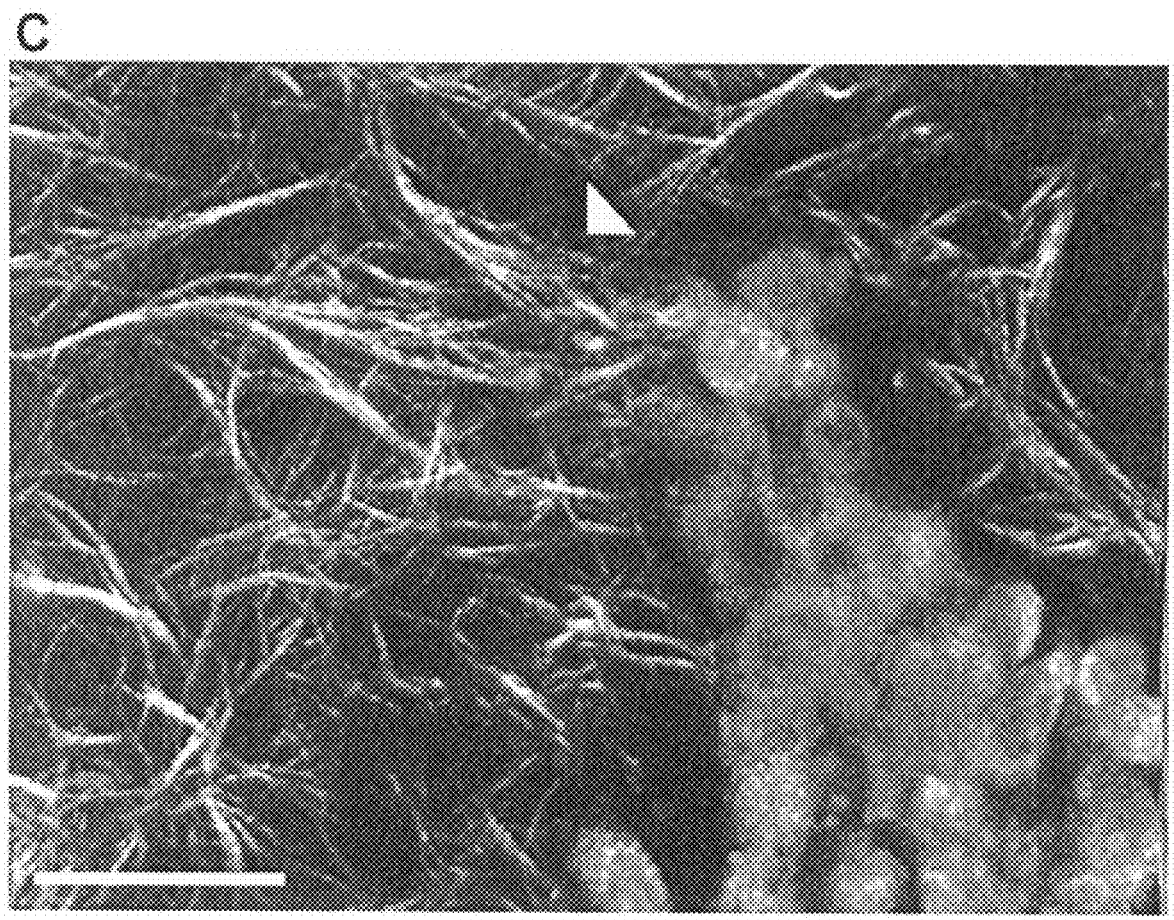
Figure 6:
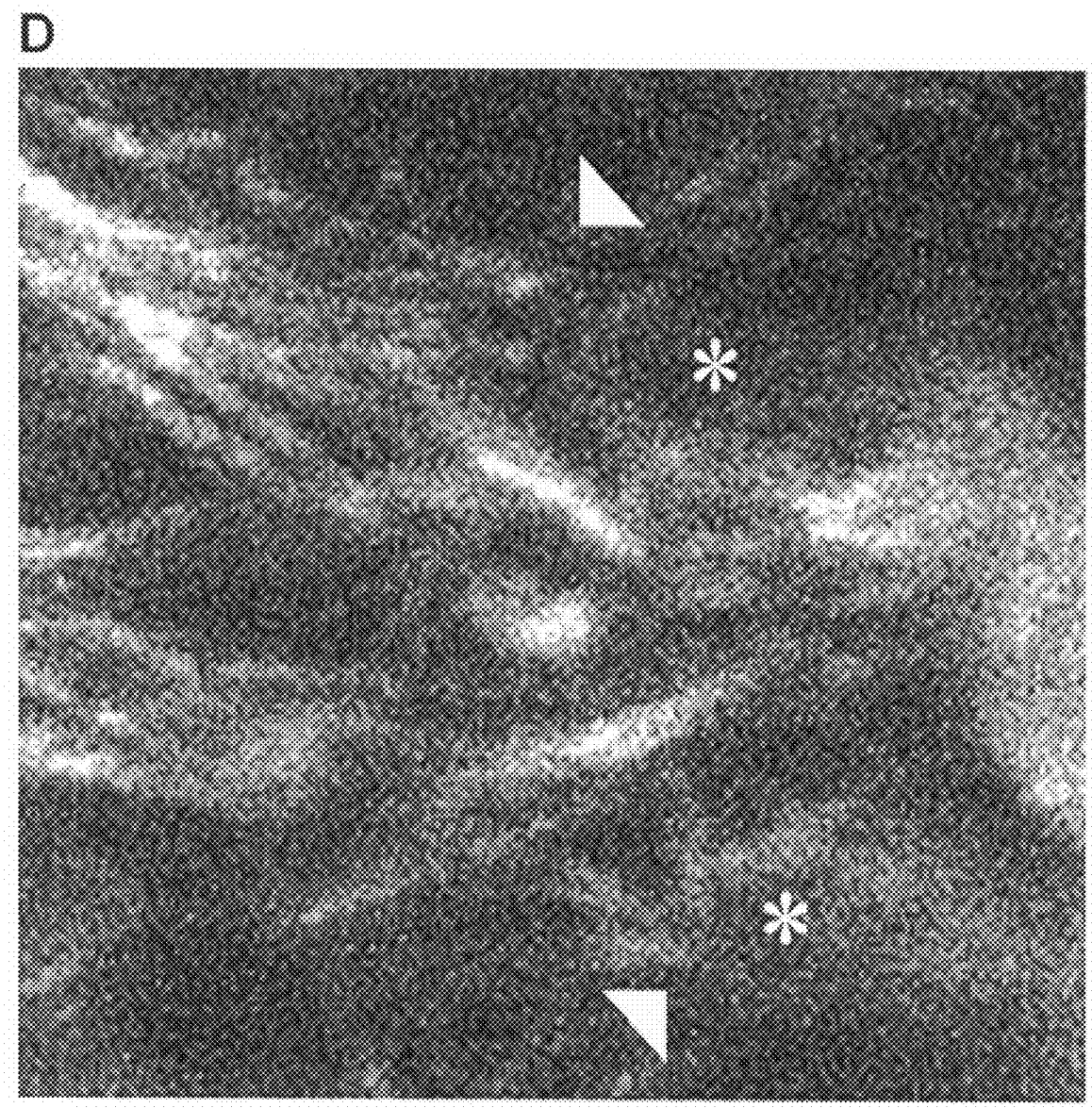

High breast tissue density (due to increased collagen) is one of the single largest risk factors for developing breast cancer, yet the molecular mechanisms behind this high risk are not known. One reason for this deficit has been the lack of adequate animal model systems for studying the effects of increased collagen density in vivo. As such, we sought to identify an animal model system possessing collagen-dense breast tissue. Analysis of the col1a1$^{tmJae}$ mouse model revealed such a system. These mice possess a type I collagen mutation in the α1 (I) chain, making them resistant to human collagenase, resulting in fibrosis of the skin and uterus due to excessive collagen accumulation, but increases in collagen deposition in the mammary gland have not been previously described. Analysis with standard histology clearly revealed increased collagen surrounding the mammary ducts in both homozygous and heterozygous female mice regardless of parous status (See, FIGS. 3A and C; Supp. FIG. 6). By utilizing histology and imaging H&E stained sections with MPLSM (SHG signal did not exist after formalin fixation), the presence of increased collagen was confirmed (See, FIGS. 3B and D), as well as an apparent hyperplasia in Col1a1 mice (See, FIGS. 3A-D; Supp. FIG. 6). This hyperplasia was further associated with invasive epithelial cells that resemble an epithelial-mesenchymal transition at the ductal end (See, FIGS. 3C-D). Therefore, we detect increased collagen in vivo in intact mammary glands. Analysis of glands from col1a1 heterozygous and homozygous mice, and associated wild-type littermates, noticeably revealed increased collagen surrounding epithelial ducts from transgenic mice (See, FIG. 3E-H), validating our ability to obtain images from deep (max. depth 440 nm) within intact mammary tissue (See, FIG. 3H) to detect density in intact tissue without fixing, sectioning, or staining the tissues. Interestingly, collagen was locally dense adjacent to (wrapped around) the epithelium as well as increased in the space extending from the duct resulting in an ~2.8 fold increase in quantifiable collagen signal (after thresholding in Imagej software) in transgenic animals. Hence, the col1a1 mouse model appears to be a promising candidate for studying the effects of increased collagen density in normal as well as transformed epithelial cells since appropriately crossed heterozygous col1a1 mice are capable of forming tumors without inhibition from the collagenase resistant matrix.

Tumor-Associated Collagen Signatures

Tumor-Associated Collagen Signature-1: Examination of the epithelial-stromal interaction in Wnt-1 mice, which possessed ductal hyperplasia (See, FIG. 4A-C), revealed abnormal mammary duct development with irregular collagen organization (See, FIG. 4B-C) that could be clearly be identified in tissues that were not fixed, sectioned, or stained (See, FIG. 4 F-G); validating the ability of MPLSM/SHG imaging to detect mammary abnormalities and abnormal collagen distribution in situ. Additional analysis of tumor bearing Wnt-1 mice revealed multiple epithelial clusters, containing hemorrhagic regions, intermixed and surrounded by increased collagenous stroma (i.e. desmoplasia; See, FIGS. 4D-E), consistent with previous reports. Importantly, we were able to identify pre-palpable tumors (See, FIGS. 4H and J) by the existence of what we are classifying as one of three tumor-associated collagen signatures (designated: TACS). Namely, TACS-1: the presence of dense collagen, indicated by increased signal intensity at a region near the tumor (See, FIGS. 4H and J) that served as a reliable hallmark for locating small tumor regions. However, it is unclear whether 1) a pre-tumor dense region is present that serves to stimulate tumor formation, 2) the dense region of collagen is pulled into a grouped cluster through increased contraction of an epithelial tumor mass, or 3) fibroblast activation results in increased local collagen deposition. Further analysis into this fundamental characteristic should provide useful information on tumor initiation and progression.

Figure 4:
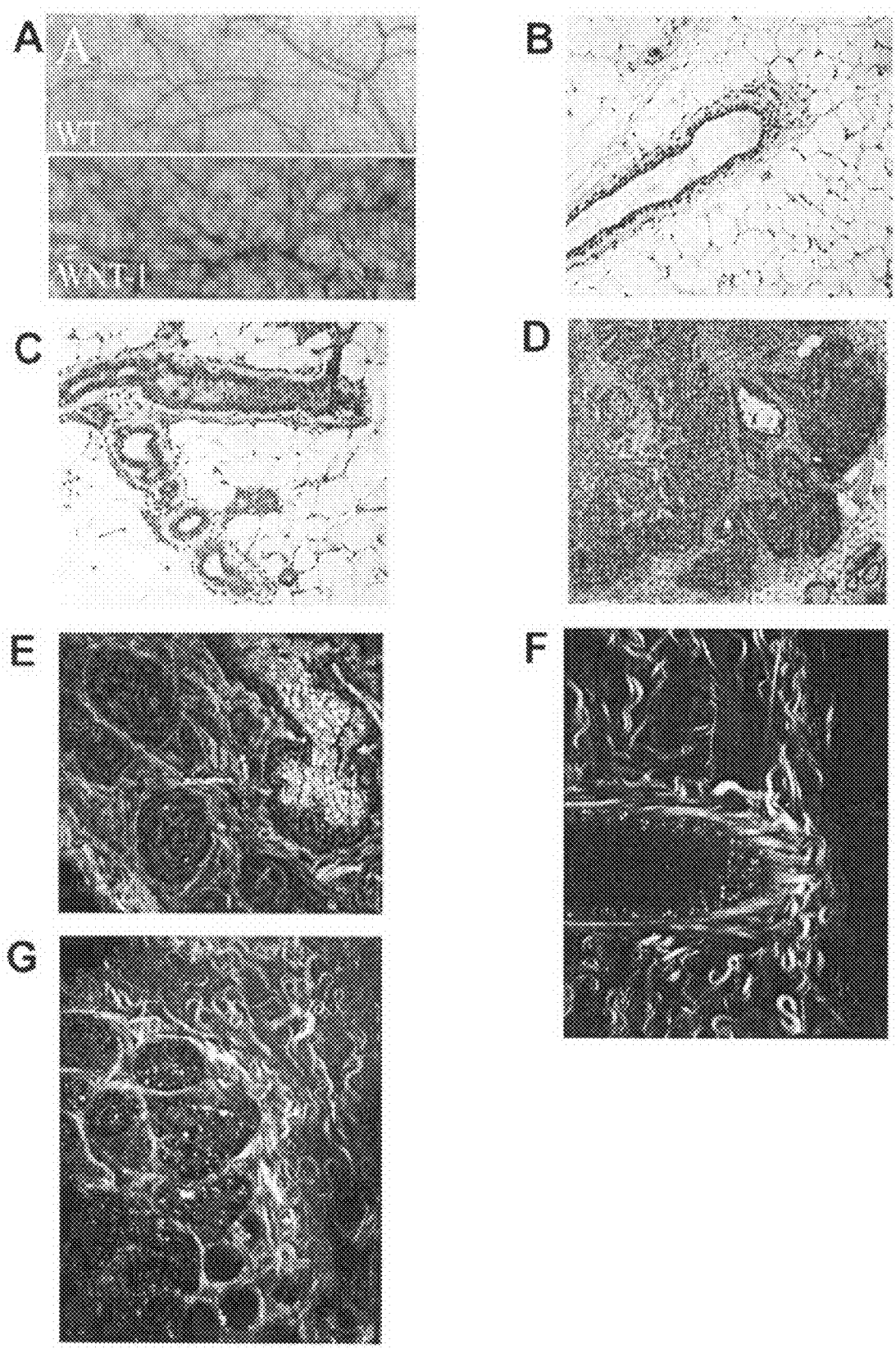
FIG. 4 provides images representing three Tumor-Associated Collagen Signatures of the present invention. (A) Whole mount analysis from Wnt-1 mice (bottom) and wild-type control (top) displaying hyperplasia. (B-C) Histology of wild-type control mammary (B; H&E) and abnormal ducts from Wnt-1 mice (C; Trichrome). (D) H&E stain of Wnt-1 mammary tumor. (E) MP image of an H&E section from Wnt-1 tumor showing increased visualization of collagen structure. (F) Wnt-1 wild-type control mammary duct. (G) Duct in Wnt-1 mice showing hyperplasia and abnormal structure. (H-S) Micrographs illustrating the identified Tumor-Associated Collagen Signatures (TACS): (H) MP/SHG image of the first TACS. Namely, a region of dense collagen "above" a non-palpable tumor that is indicative of the presence of a small tumor (see H). (I) MP/SHG image of the second TACS indicated by the presence of straightened (taut) fibers characteristic of a larger Wnt-1 tumor. (J) Zstack of (H) illustrating the detection of non-palpable tumor below locally dense collagen. (K-L) MP/SHG images of collagen fibers in Wnt-1 mice stretched around a relatively smooth tumor boundary. (M) MP/SHG image of a small Wnt-1 tumor showing collagen alignment at regions of tumor displaying a more irregular shape. (N) The third TACS: aligned collagen fibers at regions of cell invasion in Wnt-1 mice. (O-S) Further study of the third TACS in the more aggressive PyVT mouse tumor model, with enlarged cutout regions (T-V) shown at higher brightness and contrast levels and a rough demarcation of the tumor-stromal boundary (red line; s=stroma; t=tumor). Note that although some cells have moved past this boundary (examples=x) into the fibers, it serves as a general representation of irregular invasive region into radially aligned collagen fibers. * Indicates examples of fibers interdigitated with the invasive tumor boundary and in contact with the invading tumor cells. (O-Q) Tracking a tumor boundary shows regions of stretched collagen fibers around a relatively smooth tumor boundary (O), a region of reorganized (aligned) collagen fibers (P), which lead to regions of local invasion in region of aligned fibers (Q). This behavior can be further illustrated in a separate tumor shown in (R-S), demonstrating invasion at aligned regions implying the contractile reorganization of the collagen matrix plays a role in facilitating invasion. (W) Enlarged region of invasion illustrating cells (open arrow heads and dashed arrows) along fibers (*). Note the elongated (mesenchymal) phenotype of cells closely associated with the fibers. Note: F-W are from live intact tissues that are not fixed, sectioned, or stained; scale bar for MP/SHG images equals 25 µm.
Figure 4:
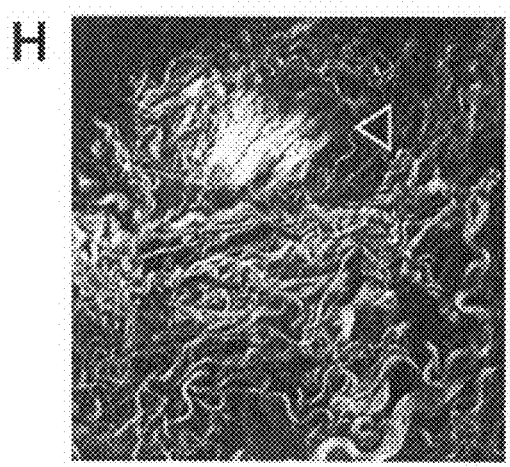
Figure 4:
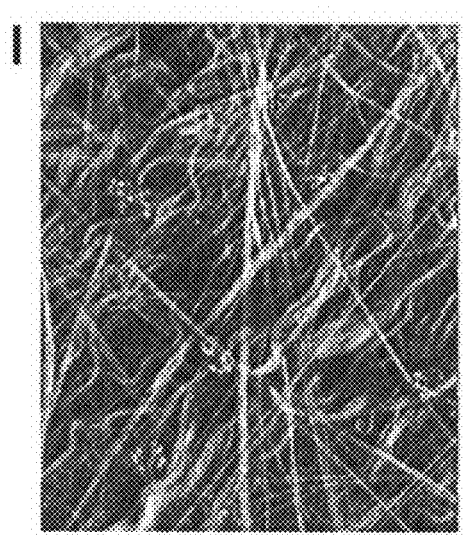
Figure 4:
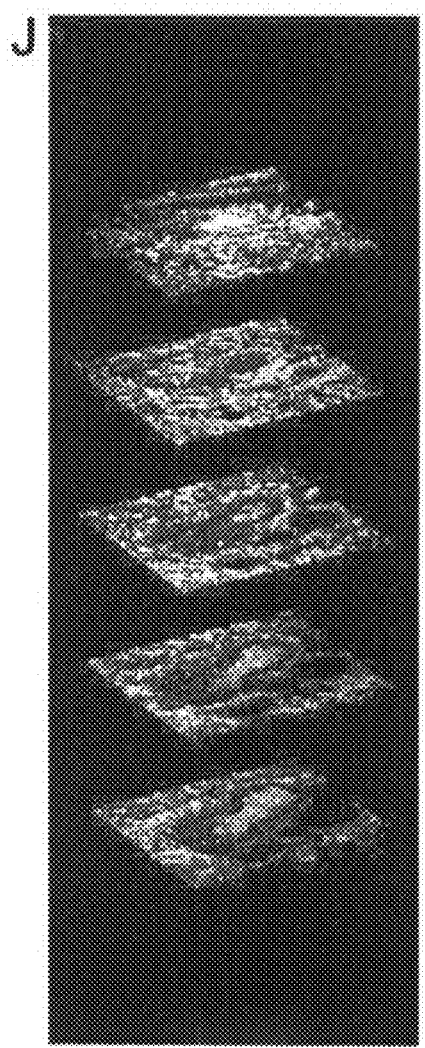
Figure 4:
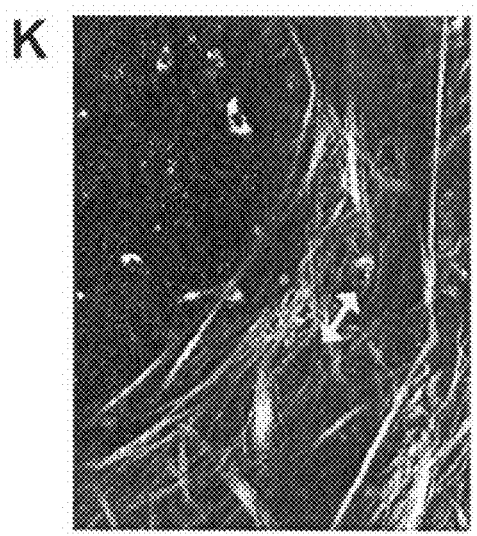
Figure 4:
Figure 4:
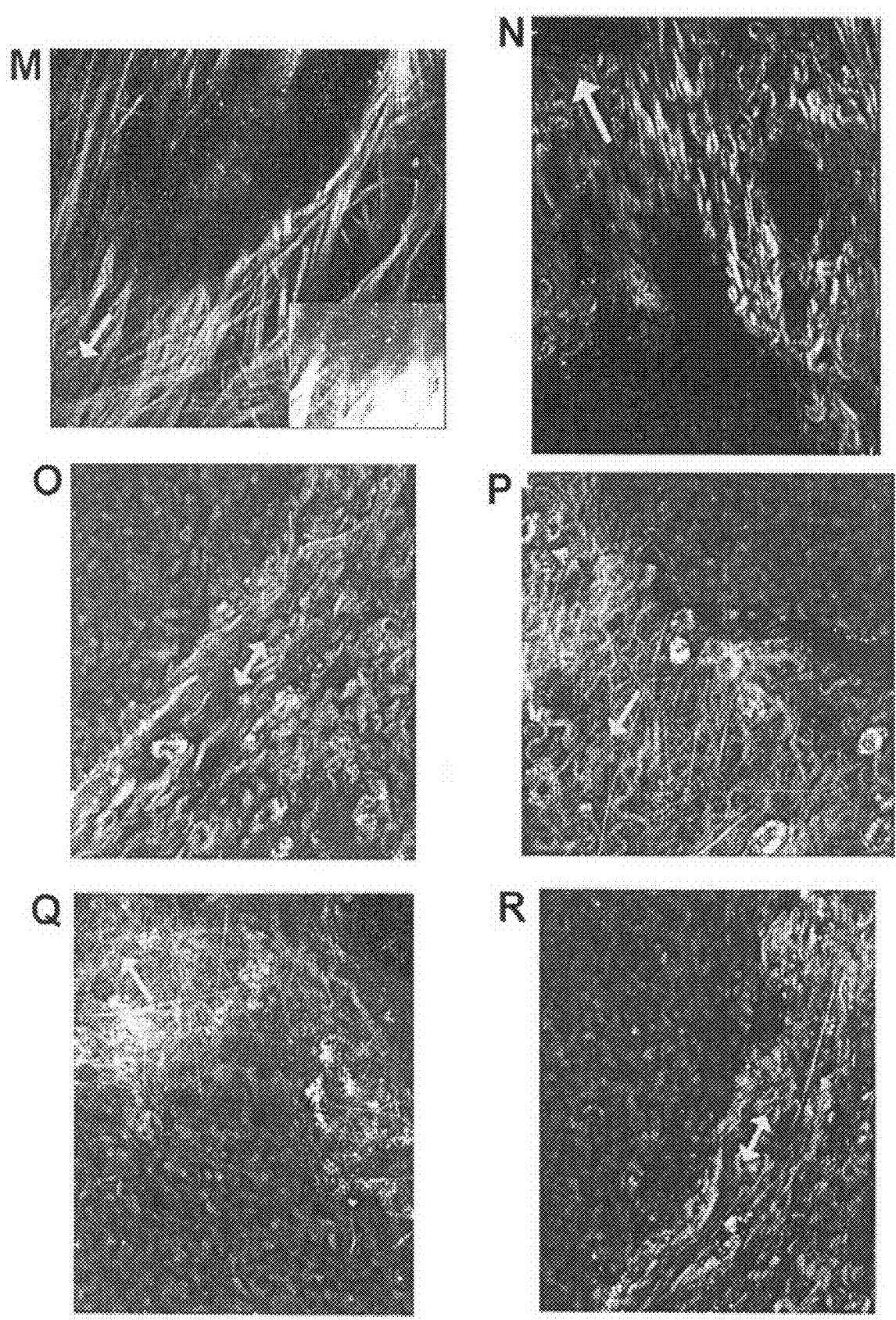
Figure 4:
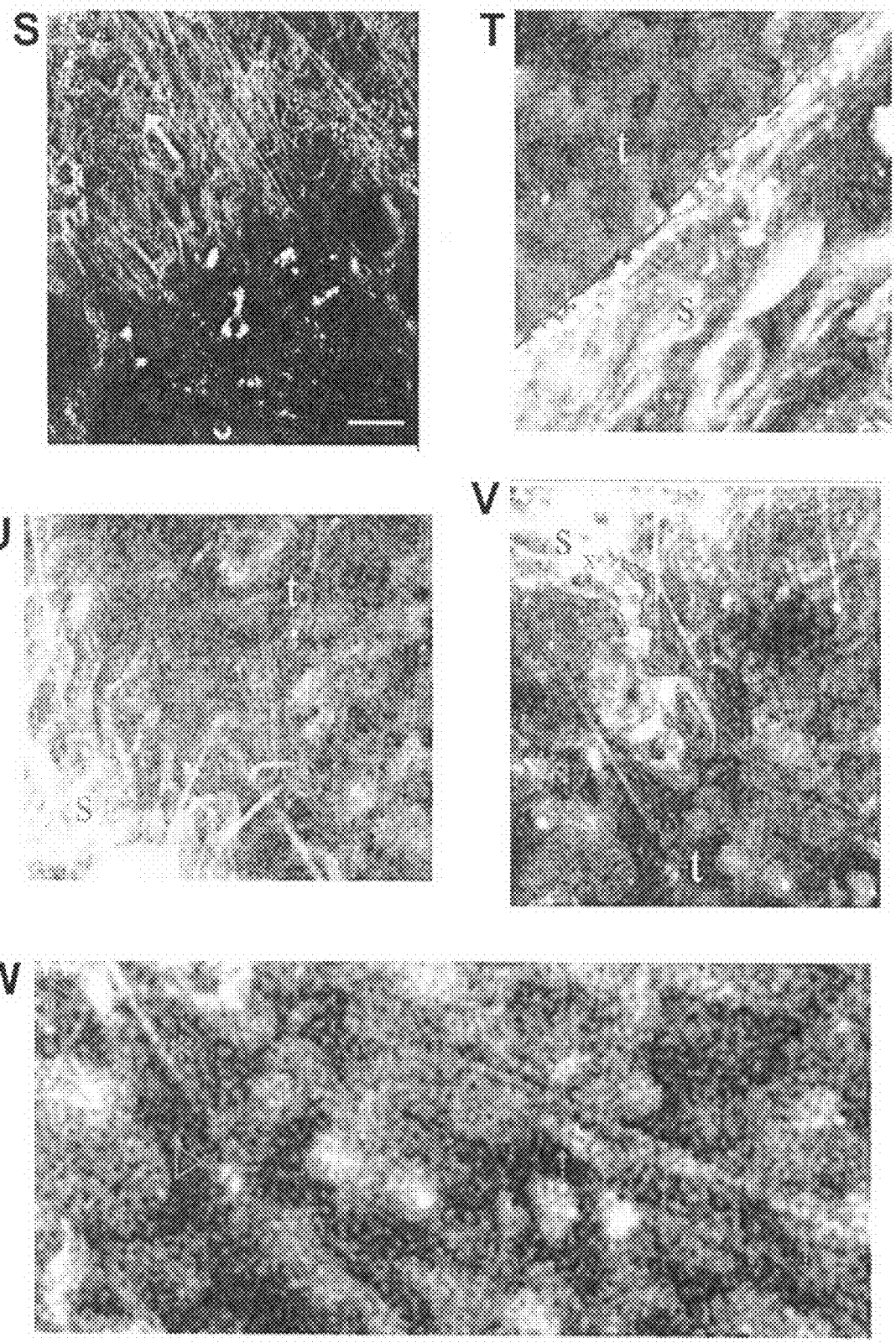

Tumor-Associated Collagen Signatures-2 and -3: As the size of the tumor increased, we identified a second collagen signature, TACS-2: "taut" collagen fibers stretched around the tumor (See, FIG. 4I). This collagen morphology likely arose from stretching of the stroma due to tumor growth, which may act to constrain portions of the tumor (i.e. compressive restraint) as well as provide a stretch induced tensile stress in expanded fibrils (larger resistance to cell contraction in the stroma) that stimulates and activates fibroblasts. Evidence for tumor restraint in Wnt-t mice can be seen in FIGS. 4 K-L, where collagen fibers are stretched around a relatively smooth tumor boundary. However in smaller tumor masses (See, FIG. 4M), that are likely undergoing rapid growth, a third tumor-associated collagen signature (TACS-3) was identified: collagen fibers aligned normal to tumor boundary regions that display irregular shape; possibly indicative of invasion through collective epithelial cell migration. This invasive tumor morphology was also seen in regions of large tumors where collagen fibers are aligned in the direction of cell invasion (i.e. TACS-3; FIG. 4N) and may be undergoing collective invasion as well as an epithelial-mesenchymal transition in individual cells that may relate to single cell migration that has been observed along collagen fibers in an in vivo xenograft model.

To further investigate the behavior of the third collagen signature in a more invasive and metastastic cancer model, we utilized the PyVT mouse model, which bears resemblance to many aspects of human cancer and therefore provides a good model for studying human disease. Tumor cell behavior and collagen morphology in this model were similar to observations from the Wnt-1 mouse tumors. For instance, tracking the tumor-stromal boundary around tumors (See, FIG. 4 set O-Q and set R-S) first revealed regions of restraining collagen wrapped around a relatively smooth boundary with cells having a mostly random alignment with a subset of cells aligned in the same direction as the collagen (See, FIG. 4O/T,R). The second region revealed a boundary where collagen has been aligned perpendicular to the tumor (See, FIG. 4P/U), most likely through morphogenesis and motility (contractility) events from cells at the tumor boundary, to organize the matrix, to assist invasion or to invade into regions with pre-aligned fibers. Evidence for this is seen by the invasion of cells in the Wnt-1 mice discussed above (See, FIGS. 4M-N) and in PyVT tumors in vivo (See, FIGS. 4Q/V and S and FIG. 5), where regions of tumor invasion show fibers aligned radially from the tumor in the direction of tumor cell invasion (See, FIGS. 4S-W). Additionally, some invading cells were in direct contact with fibers (See, FIG. 4W and FIG. 5) and some matrix disorganization present, possibly indicating proteolytic cleavage of collagen.

Analysis of tumor explants within type-I collagen gels revealed radial collagen alignment at regions of tumor cell invasion into previously randomly aligned collagen gels (See, FIG. 6), supporting information about invasion in vivo within intact live tissues. Following polymerization, collagen gels display a random orientation of collagen fibers (See, FIG. 6A) unless an outside force initiates structural reorganization. Tumor explants cultured within contracted collagen gels have collagen wrapped around the explant at non-invading regions (See, FIG. 6B). In contrast, at regions of invasion into the gels, collagen reorganization to a radial alignment is clearly present (See, FIG. 6C) with direct contact between collagen fibers and invading cells (See, FIGS. 6C and D). This demonstrates that tumor cells can de novo reorganize the random collagen matrix to facilitate invasion, supporting in vivo behavior, and indicating that matrix reorganization at the tumor interface facilitates local invasion. Hence, our results indicate that to facilitate invasion in vivo cells at the tumor boundary contract and align collagen fibrils (or whole fibers), perhaps with the assistance of proteolytic cleavage to facilitate matrix reorganization, and then invade along aligned collagen structure to expand the tumor and later metastasize.

Discussion

Intrinsic fluorescence detection with multiphoton excitation in combination with SHG facilitates three-dimensional, high resolution, imaging in non-fixed, non-sectioned, non-stained mammary tissues. This imaging provides information commonly obtained with classical histology and EM without the need for complex and destructive sample preparation, and with additional structural information in three dimensions. With MPLSM/SHG, mammary gland tissue could be clearly imaged at depths down to 440 nm with changes in collagen density reliably detected. Furthermore, three-dimensional imaging of tumors in situ revealed three "Tumor-Associated Collagen Signatures", or TACS, which provide standard hallmarks to locate and characterize tumors: TACS-1) the presence of dense collagen, indicated by increased signal intensity at a region around the tumor as a standard hallmark for locating small tumor regions, TACS-2) the presence of taut (straightened) collagen fibers stretched around the tumor, indicating tumor growth has progressed, TACS-3) the identification of radially aligned collagen fibers facilitating invasion, which is indicative of the invasive and metastatic growth potential of a tumor. Together these signatures serve a mechanism to help identify and characterize breast tumors in experimental animal models as well as human cancers and fresh tumor biopsies.

The breast epithelial cell-ECM interaction is responsible for influencing cell polarity, proliferation, differentiation, adhesion, and migration and type I collagen is an important regulator of mammary ductal formation during development. Analysis of normal mammary glands revealed collagen fibers wrapping around, as well as radiating away from, the duct (i.e. FIG. 2B). This organization is remarkably consistent with the observation that in fixed whole mounts of developing mammary gland, analyzed with MPM, collagen fibers are "pulled in" normal to the terminal end bud. Combined, these morphologies provide insight into the structure-function relationship in the mammary gland and imply that collagen may provide directional cues during development that also influence changes in the normal mammary gland. For instance, the crimped (wavy) collagen structure (i.e. FIG. 2AB, E, G) is consistent with numerous reports of crimped collagen fibers in connective tissue that allow normal tissue deformation with a strain-stiffening behavior. This behavior may hold true for the mammary gland as well, allowing for tissue deformation and normal ductal growth and involution without over constraining the system, yet providing adequate levels of tensile resistance to contracting cells and resisting large deformations that can damage the tissue. The less numerous taut fibers may serve a different purpose. They may act as locally constraining structures at the single cell level and may act to interconnect various ducts in the tissue together and to the nipple structure (See, FIG. 2F), which may transmit mechanical signals to the ducts during activities such as nursing to elicit mechanotransductive signaling related to lactation. Furthermore, such mechanical signals acting directly on epithelial cells or transmitting stress across the basement membrane would be amplified by increased breast tissue density. Hence, increased breast tissue density in vivo may promote carcinoma formation by increased mechanical signals events in dense tissue, that may relate to in vitro work showing that increased matrix density alters breast epithelial cell signaling.

The importance of matrix composition and morphology around the mammary epithelium is illustrated by studies showing that misregulated stromal-epithelial interactions can promote tumorigenesis and the fact that breast carcinomas often exhibit desmoplasia (excessive collagen surrounding an invasive tumor). Moreover, cancer cells can locally invade across basement membrane and collagenous stroma to spread into neighboring ECM environments where they can migrate further to enter lymphatic and blood vessels, resulting in metastatic growth in distant tissues. Therefore, understanding the mechanisms of invasion in vivo is of great importance. Yet, to our knowledge, no study has visualized local invasion in endogenous tumors in vivo in relation to stromal organization. Consequently, it is noteworthy that we observe alignment of collagen fibers, and association of individual cells with those fibers at regions of local invasion in vivo (TACS-3), which is similar to observations of individual cell migration along collagen fibers in a xenograft model, and confirms and expands upon in vitro studies in 3D matrices that have identified collagen reorganization (alignment) at the front of invading cells. Moreover, the concept of alignment-facilitated invasion appears to be of significance in collective cell migration (e.g. tubulogenesis in the mammary gland); as collagen alignment is noted at the terminal end bud during invasion of the mammary ductal tree. Thus, collagen alignment may facilitate motility and migration during development and tumor invasion may resemble misregulated developmental processes.

In summary, it tumor cells often localize near dense collagen or promote a desmoplastic response and contract and localize collagen, followed by tumor growth and expansion (stretching) of the collagen matrix leading to matrix reorganization (possibly assisted by proteolytic cleavage to release collagen fibers) to help facilitate local invasion. This matrix reorganization would require enhanced motility of the tumor cells, which may explain the increased presence of Rho and ROCK, in invasive cancers. Hence, the mechanisms behind local invasion may include matrix reorganization through GTPase mediated tumor cell contractility, leading to an aligned matrix facilitating local invasion.

EXAMPLE 2

Nonlinear Optical Imaging Systems for Detecting Cancer

It is a goal of the present invention to provide nonlinear optical imaging systems capable of generating information relevant to the diagnosis of cancer in biological materials, such as intact, unsectioned and unstained tissues. Useful imaging systems for some applications are noninvasive and nondestructive, and are capable of providing high resolution images of surface and subsurface components and features of tissue. Useful imaging systems are also capable of rapid in situ optical analysis, for example to provide real time imaging for facilitating therapeutic procedures, such as surgical removal of tumors and for quantitative analysis of the margins of a given tissue removal therapy.

In one embodiment, the present invention provides an optical system capable of generating, simultaneously or nonsimultaneously (e.g. sequentially) both MP laser-scanning microscopy images and harmonic generation (i.e., first, second, third, etc.) images of surface and subsurface regions or layers of tissue undergoing analysis.

Several optional features of the present nonlinear optical imaging instrumentation are useful for various diagnostic and therapeutic applications. These optional features are useful for generating high resolution images capable of providing valuable diagnostic information and for providing a user friendly, widely accessible, robust clinic tool.

To facilitate identification and characterization of tumor-associated collagen signatures a number of optional features may be incorporated to the present systems and methods to provide enhanced SHG and MP microscopy images by efficiently discriminating and isolating the SHG signal from fluorescence resulting upon illumination. First, embodiments of the present invention may employ spectral separation of the SHG and fluorescence signals via optical filtering. In one embodiment, for example, spectral separation is achieved by using one or more motorized optical filter wheels with different filters (e.g. bandpass filters, cut off filters etc.) provided in front of a photodetector(s) for isolating and discriminating SHG signal from fluorescence from endogenous fluorophors, such as elastin, NADH and FAD, and/or exogenous fluorophors (e.g. contrast agents) provided to the tissue. Use of a narrow band pass filter with a transmission maximum centered at half the excitation wavelength for SHG is useful for spectral filtering in some applications. Second, enhanced SHG image quality may be achieved in some embodiments by discriminating the SHG signal from fluorescence via lifetime separation techniques. The temporal evolution of fluorescence signals and SHG signals different substantially due to differences in the fundamental processing giving rise to these signals (e.g. radiative fluorescent decay typically occurs on a time scale significantly longer than SHG scattering). In some embodiments of the present invention providing lifetime spearation, the photodetector is gated temporally such that SHG and fluorescence signals are separated from each other in time, thus, allowing detection of the SHG signal without significant interference from fluorescence.

The present invention also includes a number of enhancements of the nonlinear optical imaging system to achieve SHG images from which tumor-associated collagen signatures and profiles may be accurately, sensitively and selectively detected and characterized. In one embodiment, forward scattered SHG light and backward scattered SHG radiation are simultaneously, but separately, collected, isolated and detected to generate a plurality of SHG images useful for diagnostic and therapeutic applications. In this embodiment, a first photodetector is positioned to detect backwards scattered SHG radiation and a second photodetector is positioned to detect forward scattered SHG radiation. In another embodiment, imaging is carried out by measuring third harmonic generation from the tissue, optionally in addition to imaging via SHG and MP microscopy methods. Additionally, the present systems and methods include additional means for quantifying fluorescent and SHG signals arising from interaction of collagen in the tissue with excitation radiation.

Nonlinear optical imaging systems of the present invention may include one or more optional components to enhanced detection sensitivity and/or functionality. In one embodiment, for example, backward scattered SHG light is detected using a Ga:Aasp photodetector providing enhanced detection sensitivity. However, systems of the present invention are not limited to use of a Ga:Aasp photodetector. Optionally, the present imaging systems include a first photodetector positioned to detect scattered SHG radiation propagating parallel to a first propagation axis and a second photodetector positioned to detect scattered SHG radiation propagating parallel to a second propagation axis that is different from the first propagation axis. This embodiment of the present invention is useful for generating a plurality of SHG images corresponding different SHG scatter angles, such as a first image corresponding to backward scattered SHG radiation and a second image corresponding to forward scattered SHG signal.

Use of a combination of images generating from MP laser-scanning microscopy and SHG in the present invention provides a number of advantages for identifying and characterizing tumor-associated collagen signatures and profiles, and for diagnosing cancer.

While the present methods are capable of generating images arising exclusive from endogenous materials in a tissue (e.g., using SHG or endogenous fluorescence), some methods of the present invention include the step of providing an exogenous agent to the sample for the purpose of enhancing image quality, such as a contrast agent, dye, or optically labeled material.

EXAMPLE 3

Nonlinear Optical Imaging of Cellular Processes in Breast Cancer

Nonlinear optical imaging techniques such as multiphoton and second harmonic generation microscopy used in conjunction with novel signal analysis techniques such as spectroscopic and fluorescence excited state life-time detection have begun to be used widely for biological studies. This is largely due to their promise to non-invasively monitor the intracellular processes of a cell together with the cell's interaction with its microenvironment. Compared to other optical methods these modalities provide superior depth penetration and viability and have the additional advantage in that they are compatible technologies that can be applied simultaneously. Therefore, application of these nonlinear optical approaches to the study of breast cancer holds particular promise as these techniques can be used to image exogenous fluorophores such as GFP as well as intrinsic signals such as second harmonic generation from collagen and endogenous fluorescence from NADH or FAD. In this example, the application of multiphoton excitation, second harmonic generation, and fluorescence lifetime imaging microscopy to relevant issues regarding the tumor-stromal interaction, cellular metabolism, and cell signaling in breast cancer is described. Furthermore, the ability to record and monitor the intrinsic fluorescence and second harmonic generation signals provides a unique tool for researchers to understand key events in cancer progression in its natural context.

As used herein the following abbreviations apply: extracellular matrix (ECM); green fluorescent protein (GFP); multiphoton laser scanning microscopy (MPLSM); multiphoton excitation (MPE); fluorescence lifetime imaging microscopy (FLIM); second harmonic generation (SHG); nicotinamide adenine dinucleotide (NAD(P)H referred to here as NADH); and flavin adenine dinucleotide (FAD).

1. Multiphoton Excitation

Multiphoton laser scanning microscopy (MPLSM) builds upon the advantages brought about by the widespread introduction of confocal laser-scanning microscopy which allows thick biological sections to be imaged through optical sectioning. Multiphoton microscopy, first introduced by Denk and colleagues (Denk et al. 1990), is an alternative optical sectioning technique where fluorescence excitation is restricted to the plane of focus, with an effective imaging depth that can greatly exceed conventional confocal microscopy (Denk et al. 1990; Centonze and White 1998), while better maintaining viability after prolonged exposure to excitation (Squirrell et al. 1999). This is largely due to the fact that multiphoton excitation occurs via multiple low-energy (typically 650-1050 nm excitation) photons acting in concert to produce an emitted photon at the same wavelength as the corresponding single photon excitation, but with less scattering and a nonlinear dependence for fluorescent intensity (Denk et al. 1990; Centonze and White 1998; Diaspro and Sheppard 2002; Helmchen and Denk 2002). Accordingly, for the case of two-photon excitation (TPE), the fluorescence intensity $I_f(t)$ is proportional to the square of the intensity of the laser light I(t) [after (Diaspro and Sheppard 2002)]:

$$I_f(t) \propto \delta_2 I(t)^2 \propto \delta_2 P(t)^2 \left[\pi \frac{(NA)^2}{hc\lambda}\right]^2,$$

where $\delta_2$ is defined as a molecular cross section that represents the dependence for the probability of TPE on the square of photon density, P(t) is the laser power, NA is the numerical aperture, h is Planck's constant, c is the speed of light, and $\lambda$ is the wavelength. Therefore, due to this quadratic dependence, and the fact that excitation only takes place when multiple low-energy photons are absorbed by a fluorophore, the probability of TPE outside the focal plane is low, resulting in the optical sectioning effect (Denk et al. 1990; Centonze and White 1998; Diaspro and Sheppard 2002; Zipfel et al. 2003); making MPLSM ideal for generating high-resolution images of introduced and/or endogenous fluorophores from deep inside live biological tissues.

2. Second Harmonic Generation

In contrast to the fluorescent emission resulting from multiphoton excitation, second harmonic generation arises from the laser field suffering a nonlinear, second-order, polarization when passing through non-centrosymmetric ordered structures (Freund and Deutsch 1986; Campagnola et al. 2002; Stoller et al. 2002; Cox et al. 2003; Mohler et al. 2003; Williams et al. 2005; Plotnikov et al. 2006), such as fibrillar collagen. In general form, this nonlinear polarization can be described as (Stoller et al. 2002; Mohler et al. 2003; Williams et al. 2005):

$$P = \chi^{(1)} * E + \chi^{(2)} * E * E + \chi^{(3)} * E * E * E + \ldots, \quad (2)$$

where the polarization (P) and electric field (E) are vectors, and the nonlinear susceptibilities, $\chi^{(i)}$, are tensors. It is the second term in equation 2 that represents SHG. Since SHG is a conserved polarizing process, the resulting coherent wave is exactly half the incident wavelength, with the intensity of the SHG signal proportional to the square of both I and $\chi^{(2)}$ (Shen 1989; Stoller et al. 2002; Mohler et al. 2003). As such, the SHG signal is proportional to the square laser intensity as well as the molecular concentration (Mohler et al. 2003), organization and orientation (Shen 1989; Williams et al. 2005) of the sample; allowing the acquisition of information regarding concentration and structure in biological materials. Furthermore, since multiphoton excitation and second harmonic generation can be executed simultaneously, yet still be differentiated due to their distinct emission signals, it provides a powerful tool for imaging heterogeneous biological tissues.

3. Application of Nonlinear Imaging in Cancer

The capacity to image live tumor cells in their native, as well as engineered, microenvironment significantly enhances our ability to understand cellular behavior and better understand tumor formation, progression, and metastasis. To this end, multiphoton excitation, second harmonic generation, and fluorescence lifetime imaging microscopy have all been successfully utilized to better identify, understand, and characterize cancer (Brown et al. 2001; Jain et al. 2002; Wang et al. 2002; Brown et al. 2003; Palmer et al. 2003; Tadrous et al. 2003; Wang et al. 2004; Bird et al. 2005; Parsons et al. 2005; Sahai et al. 2005; Skala et al. 2005). In particular, three-dimensional imaging of live tissues with MPLSM has been utilized with success to better understand two fundamental issues in cancer biology in vivo, namely: vascular behavior and metastasis (Brown et al. 2001; Jain et al. 2002; Wang et al. 2002; Wang et al. 2005). Employing intravital imaging methodologies, assisted by the introduction of xenograft cells with an engineered fluorophore such as GFP (Brown et al. 2001; Wang et al. 2002), or multiple fluorophores (Sahai et al. 2005), these researchers have gained insight into single and collective cell behavior in vivo (Brown et al. 2001; Wang et al. 2002; Wang et al. 2004) and correlated imaged cell migration and metastasis in vivo with gene expression patterns associated with tumor cell invasion and metastasis (Wang et al. 2002; Wang et al. 2004).

In addition to the ability to image exogenous fluorophores, such as GFP, specific biological molecules can be imaged due to their endogenous fluorescence or intrinsic polarization (such as the SHG signal from collagen), allowing examination of native cells and the cell-extracellular matrix (ECM) interaction in vivo. Specifically, intrinsic fluorescence from molecules such as NADH, FAD, and tryptophan (Patterson et al. 2000; Huang et al. 2002; Zipfel et al. 2003; Kirkpatrick et al. 2005), as well as SHG signals from collagen, muscle, and microtubules (Campagnola et al. 2002; Mohler et al. 2003; Zipfel et al. 2003; Williams et al. 2005; Plotnikov et al. 2006), allow direct in vivo imaging of endogenous cells and matrices, in addition to providing non-invasive fluorescent markers for studying metabolism and disease state. For instance, early work by Chance and co-workers (Galeotti et al. 1970) examined NADH in tumor cells, while others correlated changes in NADH intensity and lifetime with metastatic potential (Pradhan et al. 1995) or metabolic changes in response to chemopreventive drugs (Kirkpatrick et al. 2005).

Endogenous signals arising from polarization (i.e. SHG) or time domain studies of endogenous fluorescence (i.e. FLIM) also provide powerful tools for imaging and studying cancer in vivo, yet to date, have received less attention than multiphoton excitation for imaging live cells within intact 3D tumor microenvironments. One notable exception is the work by Jain and colleagues (Brown et al. 2003), which characterized decreases in collagen in tumors by examining SHG signals after pharmacologic intervention. Furthermore, recent work by our research group utilizing SHG in conjunction with MPE and FLIM have characterized changes in cellular autofluorescence and collagen density in mammary glands and tumors, as well as particular collagen structures associated with live tumor cell invasion. Hence, MPE, SHG, and FLIM are all capable of identifying and characterizing key features of carcinoma in vivo and provide robust tools separately, or in conjunction with one another, to elucidate important aspects of cancer biology.

4. Materials and Methods

4.i. Cell Culture

T47D cells were obtained from the American Type Culture Collection; MDA-MB-231 cells were obtained from Dr. Alan Rapraeger (University of Wisconsin); COS-7 cells were obtained from Dr. Richard Anderson (University of Wisconsin, Madison, Wis.). In certain experiments MDA-MB-231 or COS-7 were transfected with either EGFP, EGFP-Vinculin, EGFP-R-Ras, EGFP-Cdc42(WT), EGFP-Cdc42(61 L), or EGFP-Cdc42(17N), and as indicated in the text. EGFP-Vinculin was obtained from Dr. Anna Huttenlocher, (Univ. of Wisconsin), EGFP-R-Ras was subcloned into the EGFP-C1 vector, and cdc42 constructs were obtained from Dr. A. R. Howitz (University of Virginia). T47D cells were cultured at 37° C. with 10% $CO_2$ while being maintained RPMI supplemented with 10% fetal bovine serum and insulin (8 μg/mL). MDA-MB-231 cells were maintained in DMEM supplemented with 10% fetal bovine serum and cultured at 37° C. with 10% $CO_2$. COS-7 cells were maintained in DMEM (containing high glucose, L-glutamine, sodium pyruvate and pyridoxine hydrochloride) plus 10% fetal bovine serum at 37° C. with 5% $CO_2$.

Cells were cultured and imaged under standard 2D conditions or within 3D collagen matrices. For 3D culture cells were cultured within a 2.0 mg/mL type-I collagen gel (rat-tail collagen solution, BD Biosciences) neutralized with 100 mM HEPES in 2× PBS. Following gel polymerization for 1 hour, gels were soaked in cell specific media (described above) and maintained at 37° C. with 10% $CO_2$ until imaged as described in the text.

4.ii. Mammary Tumors

All animal experiments were approved by the institutional animal use and care committee and meet N.I.H. guidelines for animal welfare. To generate mammary tumors polyoma middle T (PyVT) mice (Lin et al. 2003) were employed.

4.iii. Instrumentation

For all microscopy experiments reported herein, two separate custom designed multiphoton systems were employed at the University of Wisconsin LOCI laboratory (Wokosin et al. 2003; Bird et al. 2004; Bird et al. 2005). The first system is a multiphoton laser scanning optical workstation (Wokosin et al. 2003) constructed around a Nikon Eclipse TE300 that facilitates multiphoton excitation, SHG, and FLIM. All SHG imaging was performed on this microscope and was detected from the back-scattered SHG signal (Williams et al. 2005). A 5 W mode-locked Ti:sapphire laser (Spectra-Physics-Millennium/Tsunami) excitation (laser field) source producing around 100 fs pulse widths was tuned to wavelengths between 780 or 900 nm. The beam was focused onto the sample with a Nikon 60× Plan Apo water-immersion lens (N.A.=1.2). Multiphoton and SHG signals were discriminated with 464 nm (cut-on) long pass and 445 nm narrow band pass filters, while GFP signals were isolated with a 480-550 nm (bandpass) filter (all filters: TFI Technologies, Greenfield, Mass.). Intensity and FLIM data were collected by a H7422 GaAsP photon counting PMT (Hamamatsu) connected to a time correlated single photon counting (TCSPC) system (SPC-730, Becker & Hickl).

The second microscope has been described in detail (Bird et al. 2004; Bird et al. 2005) and allows generation of multiphoton excitation intensity images in conjunction with FLIM images. In short, the system is built around an inverted microscope (Diaphot 200, Nikon, Melville, N.Y.) possessing a Bio-Rad MRC-600 confocal scanning unit (Bio-Rad, Hercules, Calif.) with source illumination from a Ti:Sapphire mode-locking laser (Coherent Mira, Coherent, Santa Clara, Calif.) pumped by an 8-W solid-state laser (Coherent Verdi) to generate pulse widths of approximately 120 fs at a repetition rate of 76 MHz, with a tuning range of ~700-1000 nm. The confocal scanning unit produces a focused scanning spot that moves across the focal plane of the imaging objective after which the laser beam is transmitted to the microscope through a transfer lens (01 LAO159, Melles Griot, Rochester, N.Y.) and impinges on a dichromatic mirror (650DCSP, Chroma, Inc., Rockingham, Vt.) that directs incident illumination to the imaging objective (60× oil immersion, 1.4 NA, Nikon) while allowing the emitted visible fluorescent light to be transmitted to a fast photon-counting detector (PMH-100, Becker & Hickl). FLIM images were acquired with an electronic system for recording fast light signals by time correlated single photon counting (SPC-830, Becker & Hickl).

Acquisition for both MPLSM systems was done with WiscScan (Nazir et al. 2006) a lab developed software acquisition package that can control both the MPLSM and FLIM collection. Image analysis for combined (and separated) MPE-SHG was performed with ImageJ (Abramoff et al. 2004) and VisBio (Rueden et al. 2004) software. Fluorescent lifetime analysis was carried out with SPCImage (Becker & Hickl), which can fit fluorescent decay data with the exponential function (Eq. 3), for one, two, or three terms, and sum individual photon counts for each pixel to construct a contrast image. The incomplete model approach in SPC Image (ref SPC Image manual) was used to compensate for instances where the fluorescence decay is slow compared to the time window defined by the repetition rate of the laser system.

5. Results and Discussion

5.i. Relevant Issues in Breast Cancer

It is estimated that 1 in 7 women have a lifetime probability of developing breast cancer and that in the year 2005 approximately 270,000 women will be diagnosed with breast cancer with an overall mortality rate of ~15% and lower survival associated with invasive and metastatic cancer. As such, techniques and tools to detect, characterize, study, and combat breast cancer are of great significance.

One of the largest risk factors for developing breast carcinoma is high breast tissue density (Boyd et al. 2002). Dense breast tissue is linked to a four-to-six fold increased risk of breast carcinoma (Boyd et al. 1998; Boyd et al. 2001), and it is known that high breast density is associated with increased collagen deposition and content (Guo et al. 2001). Therefore understanding epithelial-stromal (-collagen) interactions is of great relevance, and this importance is further highlighted by information that improper stromal-epithelial interactions can promote tumorigenesis (Ronnov-Jessen et al. 1995; Elenbaas et al. 2001; Tlsty and Hein 2001) and that metastatic breast carcinoma cells migrate away from tumors along collagen fibers (Wang et al. 2002). Moreover, aberrant signal transduction, altered metabolic state, genetic mutations, and altered transcriptional profiles have all been associated with carcinoma formation, progression, and metastasis (Hagios et al. 1998; Hanahan and Weinberg 2000; Jacks and Weinberg 2002; Muti 2004; Rangarajan et al. 2004; Condeelis et al. 2005; West et al. 2005). Therefore, as indicated in the previous section, MPE, SHG, and FLIM (or FRET-FLIM) either individually or in combination are very well suited to address important issues associated with each of these important areas of breast cancer research by utilizing both introduced (i.e. fluorescent probes, FRET probes in FRET-FLIM etc.) or endogenous (i.e. NADH, collagen etc.) signals. Examples of this utility are illustrated below.

5.ii. Breast Cancer Related Tumor-Stromal Interactions

Figure 7:
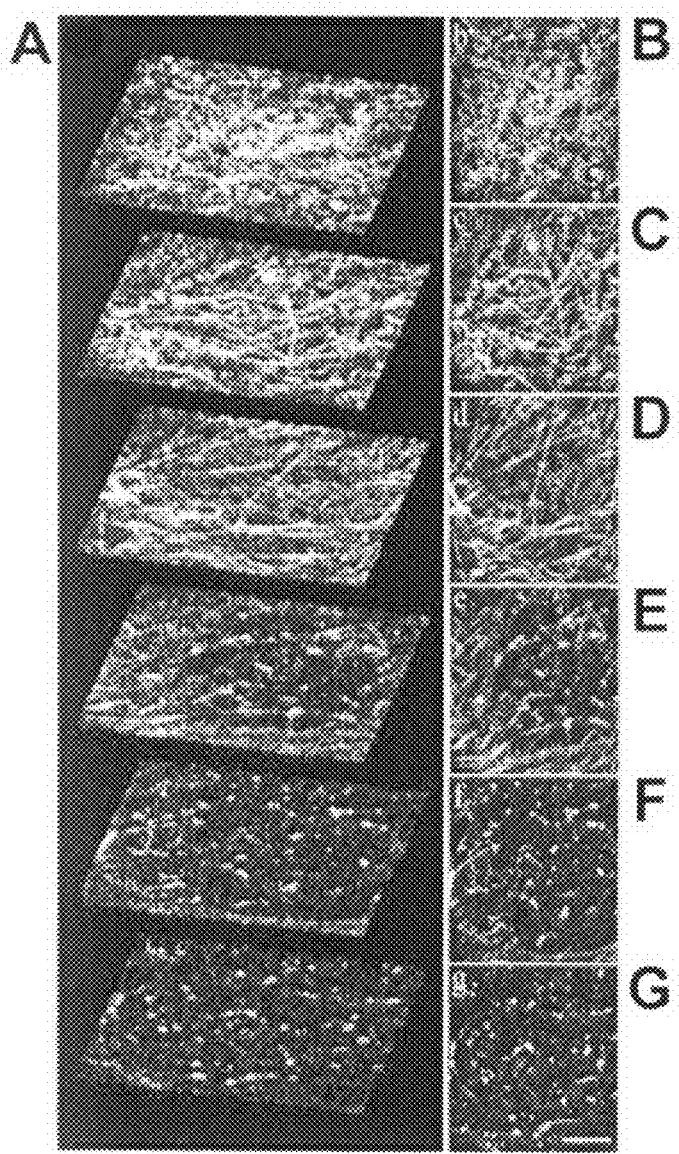
FIG. 7: Live mammary tumor. Combined MPE and SHG at $\lambda_{ex}$=890 nm facilitates imaging of intact live mammary tumor tissue. Panel (a) represents six planes of a 30-plane z-stack acquired every 10 µm (i.e. 300 µm total stack) into the tumor that was rendered and oriented with VisBio. Panels (b)-(g) show the flat images for each corresponding imaging plane. Combined panels clearly show variations in endogenous cellular fluorescence as well as collagen surrounding and within the tumor validating the ability to image deep into live tissue and obtain meaningful information. Bar=50 µm.

Understanding tumor-stromal interactions, both in vitro and in vivo, is an important aspect of the study of tumor formation and progression since stromal-epithelial interactions play a critical role in both tumorigenesis and metastasis (Ronnov-Jessen et al. 1995; Elenbaas et al. 2001; Tlsty and Hein 2001; Wang et al. 2002; Sato et al. 2004; West et al. 2005), and patients with collagen-dense breast tissue possess an increased risk of breast carcinoma (Boyd et al. 1998; Boyd et al. 2001). To help elucidate the mechanisms associated with tumor-stromal interactions in breast cancer, optical imaging modalities that allow deep imaging of live tissue are of great utility. As seen in FIG. 7, combined MPE and SHG facilitate viewing of intact live mammary tumor tissue. FIG. 7 represents six planes of a 30-plane z-stack (10 μm steps; 300 μm total range), obtained at 890 nm excitation, which clearly shows collagen surrounding and within the tumor (i.e. SHG signal), as well as endogenous tumor cell fluorescence (i.e. MPE). Importantly, variations in both collagen structure and tumor cell autofluorescence across and within imaging planes can be simultaneously acquired. Additionally, changes in local and global collagen density and specific stromal structures that influence tumor cell behavior can be obtained and defined (unpublished results). Hence, by studying the combined MPE/SHG signals in unfixed, unstained, non-sectioned tissues, the structure and composition of the stroma, as well as the degree and type of endogenous tumor-stromal interaction can be obtained.

Figure 8:
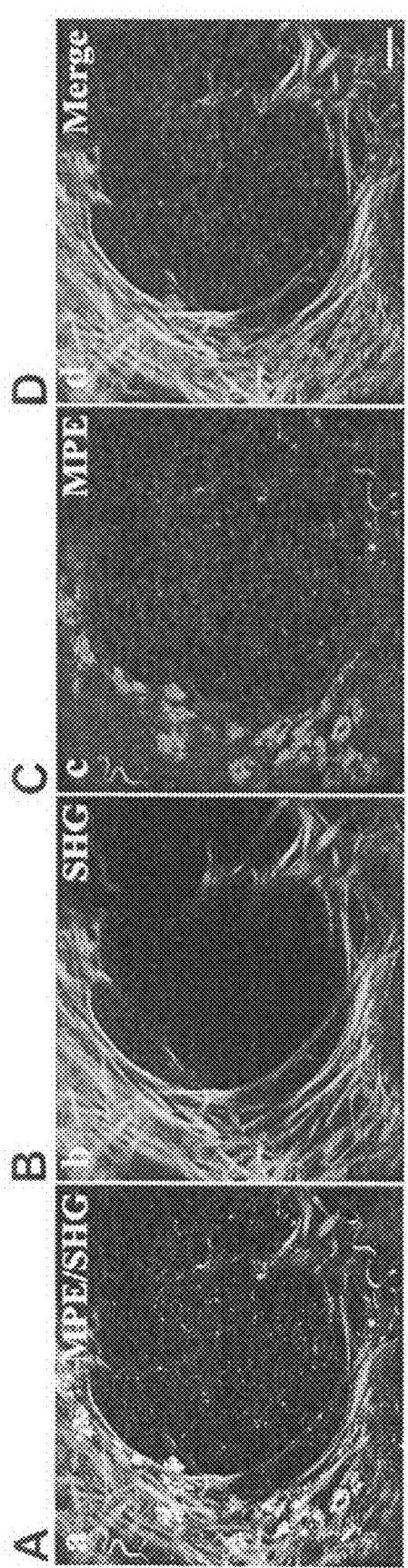
FIG. 8: MPE and SHG signal separation in live tumor. Since MPE excitation follows classical energy loss behavior while SHG signals are conserved, filtering techniques can be employed to separate the two signals following excitation with the same wavelength. Following excitation of live mammary tumor tissue with a wavelength ($\lambda_{ex}$=890 nm) that elicits both endogenous cellular fluorescence and SHG (a), the resultant emissions were separated using a 445 nm narrow band pass filter for SHG (b; pseudocolored green) and a 464 nm (cut-on) long pass filter for MPE (c; pseudocolored red). This approach allows clear visualization of the collagenous stroma (b) as well as stromal and tumor cells (c), while merging the two pseudocolored signals (d) helps reveal cell matrix interactions associated with the tumor-stromal interface. As such, the use of combined MPE/SHG has the potential to help identify and differentiate additional features that are not readily obtained with more traditional fluorescent microscopy techniques. Bar=25 µm.

To further differentiate signals (i.e. biological components) of the tumor, specific filtering techniques can be employed. By exploiting the fact that MPE excitation obeys the fundamental physical relationship of energy loss after excitation (i.e. emission of a lower energy, longer wavelength, photon following excitation by a higher energy photon) while SHG signals are exactly half of the excitation wavelength, the MPE and SHG signals can be separated (FIG. 8). Following excitation of live mammary tumor tissue at 890 nm (a wavelength that produces endogenous cellular fluorescence and SHG of type I collagen) a 464 nm (cut-on) long pass filter was used to isolate the MPE signal while a 445 nm narrow band pass filter was used to separate the signal resulting from SHG. This approach allows clear visualization of the structure and organization of collagen in the stroma as well as the presence and arrangement of stromal fibroblast-looking cells surrounding less fluorescent epithelial tumor cells (FIG. 8). Stromal cells clearly possess a more mesenchymal phenotype, demonstrate a greater fluorescent intensity, and associate with the collagenous stroma, with cells often aligned with collagen fibers. Thus, the use of combined MPE/SHG has the potential to help identify and differentiate additional features that are either not obtainable or not easily obtained with more traditional fluorescent microscopy techniques.

Figure 9:
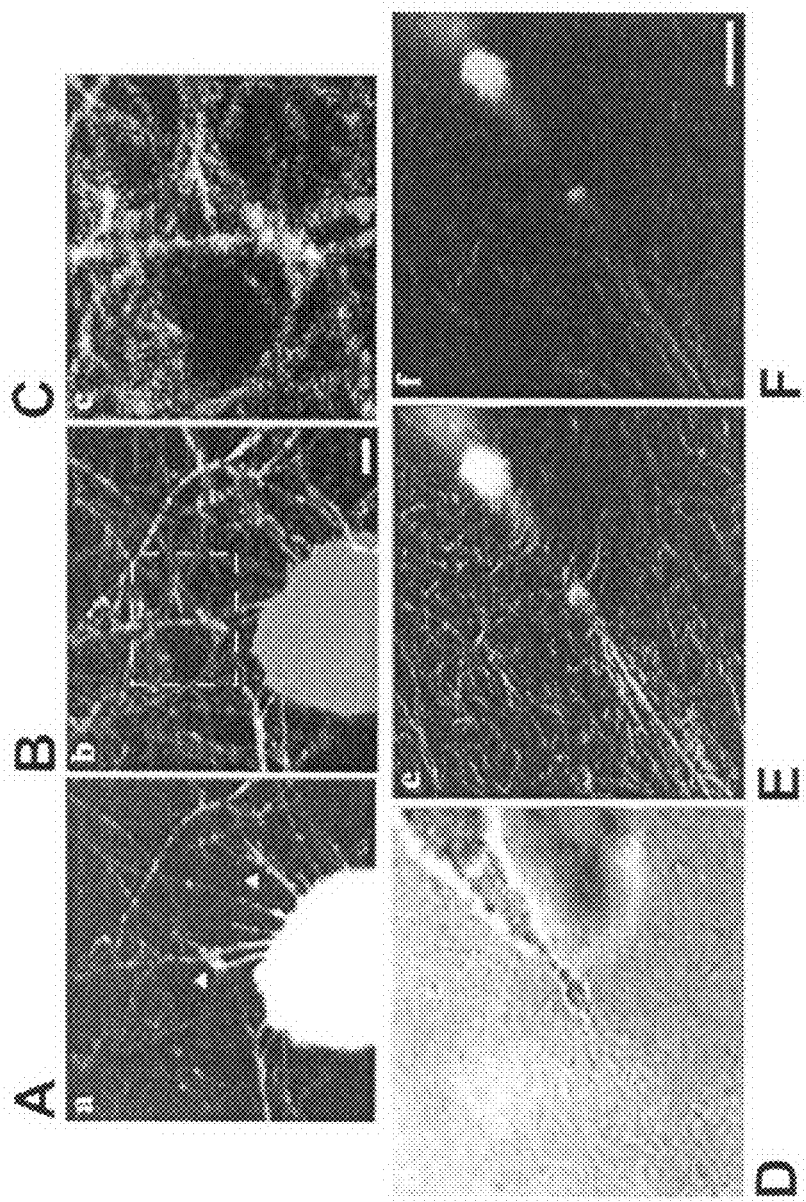
FIG. 9: Invasive breast carcinoma cells in 3D matrices. Highly invasive and migratory MDA-MB-231 breast carcinoma cells cultured within reconstituted 3D collagen matrices to further examine the utility of combined MPE/SHG to probe the cell-matrix interaction. After three hours in collagen gels (a-c), MDA-MB-231 cells expressing GFP-Vinculin form 3D matrix adhesions by presenting filopodia that interact with collagen fibers (arrows in (a)). As is shown in (b), this interaction can be highlighted by separating the SHG signal (445 nm narrow band pass filter; green pseudocolor) and the GFP signal (480-550 nm band pass filter; red pseudocolor), while (c) is a magnified region (dashed box) of (b) clearly demonstrating vinculin positive filopodia interacting with collagen fibers. After 24 hours in 3D collage matrices (d: transmitted light), MDA-MB-231 (GFP-vinculin) cells have aligned collagen fibers with vinculin localization at the cell-matrix interface (e, f: GFP=green pseudocolor; SHG blue pseudocolor). Hence, simultaneous imaging of cellular processes and matrix organization and structure with combined MPE/SHG not only facilitates imaging of non-native and endogenous signals in vivo, but also provides a robust tool to study tumor-stromal interactions in live (unfixed, unstained, non-sectioned) cells in vitro, which can further our understanding of the in vivo condition. Bar (a-c)=10 µm; Bar (d-f)=25 µm.

In addition to the powerful data obtained from live tissue imaging with MPE, SHG, and FLIM, significant understanding can be gained by applying these technologies to more controllable in vitro systems. For instance, studying breast epithelial cells within reconstituted three-dimensional (3D) matrices in vitro (Keely et al. 1995; Wozniak et al. 2003) provides a potent and relevant model system for understanding cell behavior in vivo, particularly the epithelial-stromal interaction. For instance, studies on breast epithelial cells in 3D have demonstrated that improper regulation of integrin behavior, integrin mediated adhesion to the ECM, and adhesion mediated signaling profoundly influence cell signaling that can result in a more transformed phenotype (Keely et al. 1995; Wozniak et al. 2003; Paszek et al. 2005). Furthermore the physical act of tumor cell invasion and metastasis is largely, but not solely, regulated by integrins and focal adhesion signaling (Friedl and Wolf 2003; Friedl et al. 2004), with staining for $\beta_1$ integrin (a primary collagen receptor) localized at the leading edge of migrated melanoma cells from 3D tumor explants (Hegerfeldt et al. 2002; Friedl et al. 2004). A similar behavior can be seen in live breast carcinoma cells. Inspection of live highly migratory MDA-MB-231 invasive breast carcinoma cells within reconstituted 3D collagen matrices further highlights the cell-matrix interaction via 3D-matrix adhesions (FIG. 9). Simultaneous imaging of GFP-Vinculin with MPE and the collagen gel with SHG reveals vinculin positive 3D-matrix adhesion at the cell-ECM interface. Early morphology of MDA-MB-231 (GFP-Vinculin) cells seeded into collagen matrices after three hours (FIG. 9a-c) indicates that the cells have not fully spread and exhibit vinculin positive filopodia-like structures that interact with collagen fibrils (see FIG. 9c). This early interaction is likely an early step in cell anchorage and spreading, followed by contractility-mediated reorganization of the ECM, and ultimately migration. As such, examination of migratory MDA-MB-231 (GFP-vinculin) cells after 24 hours in the 3D matrices show aligned collagen fibers associated with vinculin localization (FIG. 9d-f), which are similar to results from melanoma cells in 3D collagen gels in vitro (Hegerfeldt et al. 2002; Friedl et al. 2004). Hence, simultaneous imaging of cellular processes and matrix organization and structure with combined MPE/SHG not only facilitates imaging of non-native and endogenous signals in vivo, but also provides a robust tool to study tumor-stromal interactions in live (unfixed, unstained, non-sectioned) cells in vitro, which can further our understanding of the in vivo condition.

5.iii. Breast Cell Metabolism

Intrinsic fluorescence allows imaging of cells and tissues in their native environment, often conferring an advantage over imaging an introduced fluorophore when viewing biological structures in a relatively unperturbed environment is desired. Moreover, changes in metabolic status can be indicative of a diseased state (Galeotti et al. 1970; Pradhan et al. 1995; Pitts et al. 2001; Katz et al. 2002; Palmer et al. 2003; Kirkpatrick et al. 2005). For example, differences in NADH have been used to differentiate normal and cancerous epithelial tissues (Skala et al. 2005) with NADH intensity and lifetime altered with metastatic potential (Pradhan et al. 1995); and specific metabolic changes in NADH and tryptophan in response to chemopreventive drugs has been reported (Kirkpatrick et al. 2005).

Figure 10:
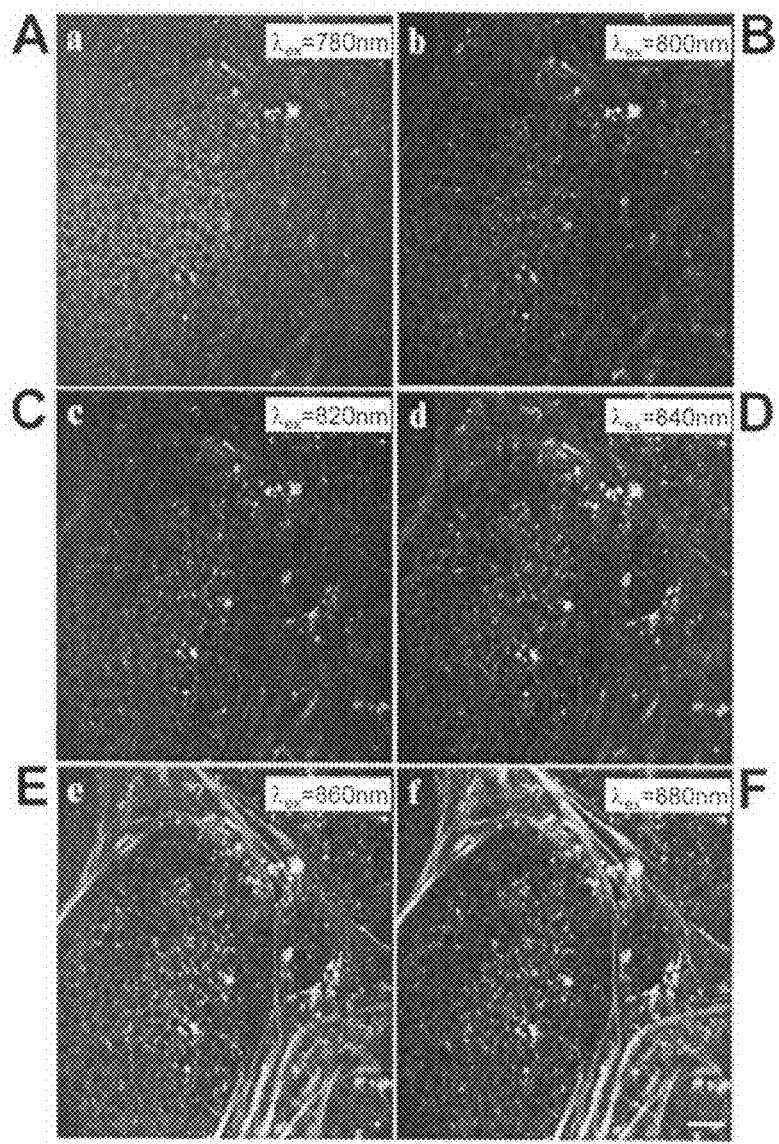
FIG. 10: Changes in breast tumor cell and matrix signals as a function of excitation wavelength. By increasing the excitation wavelength from 780 to 880 nm in 20 nm increments, changes in the intensity and localization of endogenous fluorescence as well the emergence of collagen SHG at 860-880 nm is detectable. Bar=25 µm.

Since biological tissues are heterogeneous, excitation often results in emission from multiple fluorophores with overlapping spectra. Therefore understanding the spectral properties of key fluorophores that correlate with specific cellular activity and that utilize specific excitation wavelengths as a tool to image endogenous structures are of great utility. While multiple sources of biological autofluorescence exist (see (Ramanujam 2000; Zipfel et al. 2003)), three strong (primary) sources of cellular autofluorescence are NADH (maximum $\lambda_{ex}/\lambda_{em}$: 350/450 nm), FAD (maximum $\lambda_{ex}/\lambda_{em}$: 450/535 nm), and tryptophan (maximum $\lambda_{ex}/\lambda_{em}$: 280/340 nm). FIG. 10 illustrates changes in breast tumor cell and matrix fluorescent intensity and localization as a function of excitation wavelength. At $\lambda_{ex}$=780 nm, a wavelength that is close to the ideal two-photon absorption peak of NADH, a reasonably homogeneous pattern of endogenous cellular fluorescence in the cytoplasm is clearly visible (FIG. 10a). However, as the excitation wavelength is increased in 20 nm increments to 880 nm, changes in fluorescent intensity and localization can be discerned and the emergence of collagen SHG signal at $\lambda_{ex}$=860-880 nm can be detected (FIG. 10); likely indicating changes in emission transitioning from two-photon excitation of NADH to FAD and possibly a relatively small three-photon excitation of tryptophan and/or three-photon excitation of a lower 260 nm peak for NADH.

5.iv. Imaging Signaling Events Relevant to Breast Cancer

Figure 11:
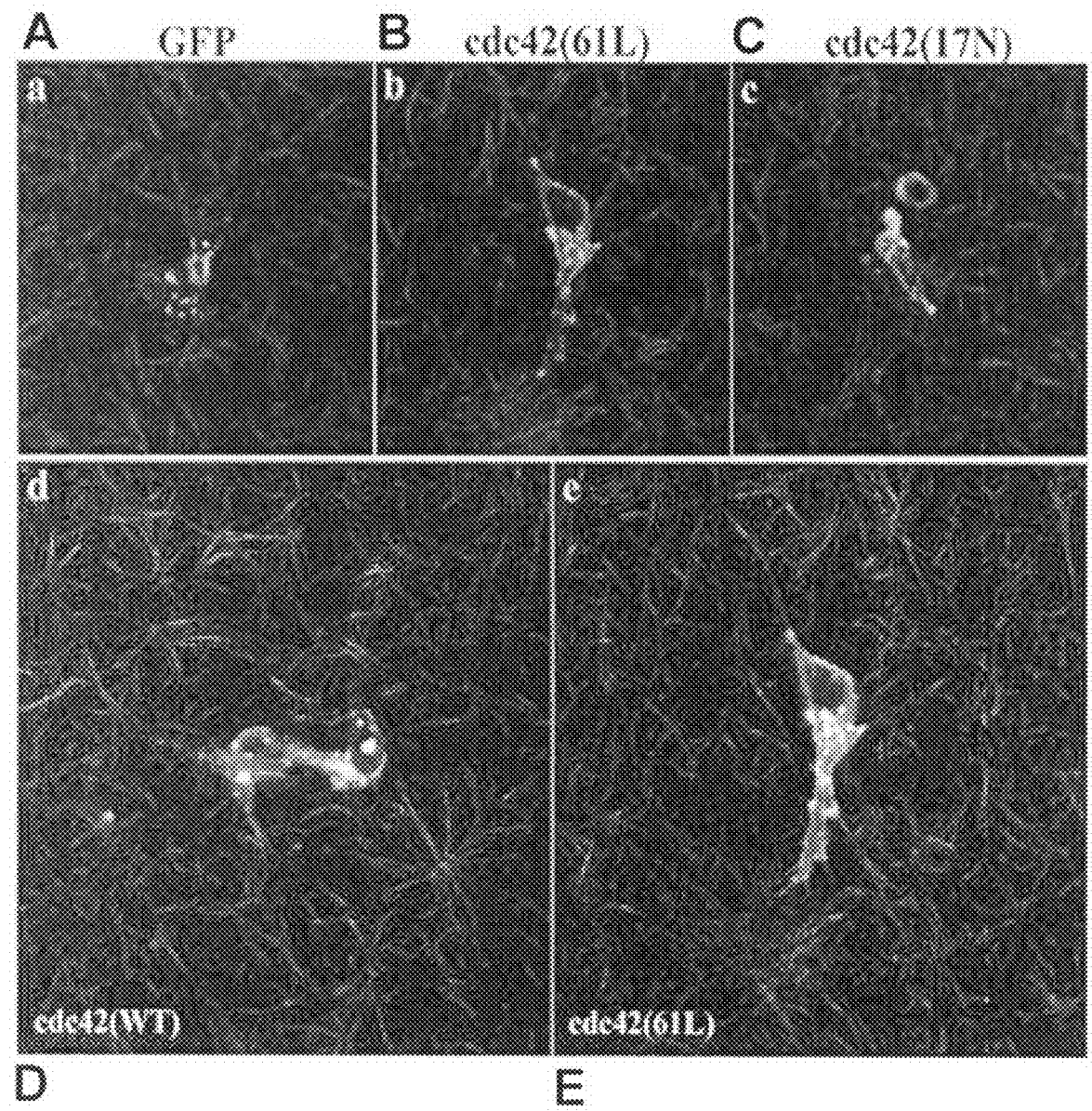
FIG. 11: Combined MPE/SHG of GFP-cdc42 in MDA-MB-231 cells within 3D collagen matrices. Live cells within type I collagen gels were imaged with combined MPE/SHG at $\lambda_{ex}$=890 nm. After six hours within 3D collagen gels differences in cell morphology and the cell matrix interaction could be detected as a function of cdc42 state. Cells expressing constitutively active cdc42 (b) were more spread and presented more cell protrusions than both control GFP cells (a) and dominant negative expressing cells (c). Additionally over-expression of wild type cdc42 resulted in cell protrusion (d), but were not as spread as cells expressing constitutively active cdc42 (e). Moreover, separation of the GFP signal (480-550 nm band pass filter; green pseudocolor) from SHG (445 narrow band pass filter, blue pseudocolor), reveals increased cell matrix attachments in cdc42(61 L) cells with cdc42 localized to cell protrusions that are interacting with the collagen matrix.

Aberrant cell signaling events and the signaling pathways associated with changes in cell survival, proliferation, and the transformed phenotype are critical phenomena that need to be elucidated in breast cancer. Although many studies have utilized GFP tagged signaling approaches to better understanding cellular processes with standard fluorescence and confocal microscopy (for example see (Lippincott-Schwartz et al. 2001; Zhang et al. 2002; Lippincott-Schwartz and Patterson 2003)), less work has been performed utilizing MPE of fluorescently-tagged signaling molecules in live cells, particularly utilizing combined MPE and SHG in 3D. However, several works have shown that MPE can be used in live cells to better understand key signaling events and other cellular processes (Strome et al. 2001; Robu et al. 2003; Poteryaev et al. 2005; Squirrell et al. 2006). In FIG. 11, MDA-MB-231 were transfected with either GFP, or GFP tagged wild-type (wt), constitutively active (61 L), or dominant negative (17N) constructs of cdc42. Live cells within type I collagen gels were imaged with combined MPE/SHG at $\lambda_{ex}$=890 nm to detect changes in cell morphology and tagged-cdc42 localization as well as cell-induced changes in collagen gel microstructure (FIG. 11). After six hours within 3D collagen gels, cells expressing constitutively active cdc42(61 L) were more spread and formed more cell protrusions than either control GFP cells or cells expressing dominant negative cdc42(17N) form and have began to align the collagen matrix (FIG. 10*a-c*). Moreover, cells with active cdc42(61 L) had begun to organize and align the collagen matrix with clear cell matrix interactions while cdc42(17N) expressing cells had not (FIG. 10*a-c*). Of additional note, cells expressing wild-type cdc42 (GFP-cdc42(WT)) possessed long cell protrusions compared to control GFP cells but were not as spread as cdc42(61 L) cells (FIG. 5*d,e*), possibly indicating that these cells overexpress cdc42 compared to control GFP cells, further suggesting that cellular protrusion (filopodia) and cell spreading correlates to the amount of active cdc42. Combined with the early filopodia-matrix interactions at three hours (FIG. 9) these data may suggest that activated cdc42 (which is known to regulate filopodia protrusion (DeMali and Burridge 2003; Jaffe and Hall 2005) results in increased early matrix interactions resulting in a more spread cell by six hours. However, additional studies are required to better understand the temporal relation of cell morphology and signaling in 3D environments. Yet, FIG. 11 clearly demonstrates the ability of combined MPE/SHG to image relevant signaling events in live breast carcinoma cells and their interaction with, and modulation of, the extracellular matrix.

REFERENCES

Abramoff, M. D., Magelhaes, P. J. and Ram, S. J. (2004). "Image Processing with ImageJ." Biophotonics International 11(7): 36-42.

Ada-Nguema, A. S., Xenias, H., Sheetz, M. P. and Keely, P. J. (2006). "The small GTPase R-Ras regulates organization of actin and drives membrane protrusions through the activity of PLC{epsilon}." J Cell Sci 119(Pt 7): 1307-19.

Becker, W., Bergmann, A., Hink, M. A., Konig, K., Benndorf, K. and Biskup, C. (2004). "Fluorescence lifetime imaging by time-correlated single-photon counting." Microsc Res Tech 63(1): 58-66.

Bird, D. and Gu, M. (2002). "Fibre-optic two-photon scanning fluorescence microscopy." J Microsc 208(Pt 1): 35-48.

Bird, D. and Gu, M. (2002). "Resolution improvement in two-photon fluorescence microscopy with a single-mode fiber." Appl Opt 41(10): 1852-7.

Bird, D. and Gu, M. (2003). "Two-photon fluorescence endoscopy with a micro-optic scanning head." Opt Lett 28(17): 1552-4.

Bird, D. K., Eliceiri, K. W., Fan, C. H. and White, J. G. (2004). "Simultaneous two-photon spectral and lifetime fluorescence microscopy." Appl Opt 43(27): 5173-82.

Bird, D. K., Yan, L., Vrotsos, K. M., Eliceiri, K. W., Vaughan, E. M., Keely, P. J., White, J. G. and Ramanujam, N. (2005). "Metabolic mapping of MCF10A human breast cells via multiphoton fluorescence lifetime imaging of the coenzyme NADH." Cancer Res 65(19): 8766-73.

Boyd, N. F., Dite, G. S., Stone, J., Gunasekara, A., English, D. R., McCredie, M. R., Giles, G. G., Tritchler, D., Chiarelli, A., Yaffe, M. J. and Hopper, J. L. (2002). "Heritability of mammographic density, a risk factor for breast cancer." N Engl J Med 347(12): 886-94.

Boyd, N. F., Lockwood, G. A., Byng, J. W., Tritchler, D. L. and Yaffe, M. J. (1998). "Mammographic densities and breast cancer risk." Cancer Epidemiol Biomarkers Prev 7(12): 1133-44.

Boyd, N. F., Martin, L. J., Stone, J., Greenberg, C., Minkin, S. and Yaffe, M. J. (2001). "Mammographic densities as a marker of human breast cancer risk and their use in chemoprevention." Curr Oncol Rep 3(4): 314-21.

Brakenhoff, G. J., van der Voort, H. T., van Spronsen, E. A., Linnemans, W. A. and Nanninga, N. (1985). "Three-dimensional chromatin distribution in neuroblastoma nuclei shown by confocal scanning laser microscopy." Nature 317(6039): 748-9.

Brown, E., McKee, T., diTomaso, E., Pluen, A., Seed, B., Boucher, Y. and Jain, R. K. (2003). "Dynamic imaging of collagen and its modulation in tumors in vivo using second-harmonic generation." Nat Med 9(6): 796-800.

Brown, E. B., Campbell, R. B., Tsuzuki, Y., Xu, L., Carmeliet, P., Fukumura, D. and Jain, R. K. (2001). "In vivo measurement of gene expression, angiogenesis and physiological function in tumors using multiphoton laser scanning microscopy." Nat Med 7(7): 864-8.

Campagnola, P. J., Millard, A. C., Terasaki, M., Hoppe, P. E., Malone, C. J. and Mohler, W. A. (2002). "Three-dimensional high-resolution second-harmonic generation imaging of endogenous structural proteins in biological tissues." Biophys J 82(1 Pt 1): 493-508.

Centonze, V. E. and White, J. G. (1998). "Multiphoton excitation provides optical sections from deeper within scattering specimens than confocal imaging." Biophys J 75(4): 2015-24.

Condeelis, J., Singer, R. H. and Segall, J. E. (2005). "The great escape: when cancer cells hijack the genes for chemotaxis and motility." Annu Rev Cell Dev Biol 21: 695-718.

Cox, G., Kable, E., Jones, A., Fraser, I., Manconi, F. and Gorrell, M. D. (2003). "3-dimensional imaging of collagen using second harmonic generation." J Struct Biol 141(1): 53-62.

Cremazy, F. G., Manders, E. M., Bastiaens, P. I., Kramer, G., Hager, G. L., van Munster, E. B., Verschure, P. J., Gadella, T. J., Jr. and van Driel, R. (2005). "Imaging in situ protein-DNA interactions in the cell nucleus using FRET-FLIM." Exp Cell Res 309(2): 390-6.

DeMali, K. A. and Burridge, K. (2003). "Coupling membrane protrusion and cell adhesion." J Cell Sci 116(12): 2389-2397.

Denk, W., Strickler, J. H. and Webb, W. W. (1990). "Two-photon laser scanning fluorescence microscopy." Science 248(4951): 73-6.

Diaspro, A. and Sheppard, C. J. R. (2002). Two-Photon Excitation Fluorescence Microscopy. Confocal and Two-Photon Microscopy: Foundations, Applications, and Advances. A. Diaspro. New York, Wiley-Liss, Inc.: 39-73.

Elenbaas, B., Spirio, L., Koerner, F., Fleming, M. D., Zimonjic, D. B., Donaher, J. L., Popescu, N.C., Hahn, W. C. and Weinberg, R. A. (2001). "Human breast cancer cells generated by oncogenic transformation of primary mammary epithelial cells." Genes Dev 15(1): 50-65.

Eliceiri, K. W., Fan, C. H., Lyons, G. E. and White, J. G. (2003). "Analysis of histology specimens using lifetime multiphoton microscopy." J Biomed Opt 8(3): 376-80.

Eliceiri, K. W. and Rueden, C. (2005). "Tools for visualizing multidimensional images from living specimens." Photochem Photobiol 81(5): 1116-22.

Flusberg, B. A., Cocker, E. D., Piyawattanametha, W., Jung, J. C., Cheung, E. L. and Schnitzer, M. J. (2005). "Fiber-optic fluorescence imaging." Nat Methods 2(12): 941-50.

French, T., So, P. T., Weaver, D. J., Jr., Coelho-Sampaio, T., Gratton, E., Voss, E. W., Jr. and Carrero, J. (1997). "Two-photon fluorescence lifetime imaging microscopy of macrophage-mediated antigen processing." J Microsc 185 (Pt 3): 339-53.

Freund, I. and Deutsch, M. (1986). "Second-harmonic microscopy of biological tissue." Optics Letters 11 (2): 94-96.

Friedl, P., Hegerfeldt, Y. and Tusch, M. (2004). "Collective cell migration in morphogenesis and cancer." Int J Dev Biol 48(5-6): 441-9.

Friedl, P. and Wolf, K. (2003). "Tumour-cell invasion and migration: diversity and escape mechanisms." Nat Rev Cancer 3(5): 362-74.

Galeotti, T., van Rossum, G. D., Mayer, D. H. and Chance, B. (1970). "On the fluorescence of NAD(P)H in whole-cell preparations of tumours and normal tissues." Eur J Biochem 17(3): 485-96.

Goldberg, I. G., Allan, C., Burel, J. M., Creager, D., Falconi, A., Hochheiser, H., Johnston, J., Mellen, J., Sorger, P. K. and Swedlow, J. R. (2005). "The Open Microscopy Environment (OME) Data Model and XML file: open tools for informatics and quantitative analysis in biological imaging." Genome Biol 6(5): R47.

Guo, Y. P., Martin, L. J., Hanna, W., Banerjee, D., Miller, N., Fishell, E., Khokha, R. and Boyd, N. F. (2001). "Growth factors and stromal matrix proteins associated with mammographic densities." Cancer Epidemiol Biomarkers Prev 10(3): 243-8.

Hagios, C., Lochter, A. and Bissell, M. J. (1998). "Tissue architecture: the ultimate regulator of epithelial function?" Philos Trans R Soc Lond B Biol Sci 353(1370): 857-70.

Hanahan, D. and Weinberg, R. A. (2000). "The hallmarks of cancer." Cell 100(1): 57-70.

Harpur, A. G., Wouters, F. S. and Bastiaens, P. I. (2001). "Imaging FRET between spectrally similar GFP molecules in single cells." Nat Biotechnol 19(2): 167-9.

Hegerfeldt, Y., Tusch, M., Brocker, E.-B. and Friedl, P. (2002). "Collective Cell Movement in Primary Melanoma Explants: Plasticity of Cell-Cell Interaction, {beta}1-Integrin Function, and Migration Strategies." Cancer Res 62(7): 2125-2130.

Helmchen, F. and Denk, W. (2002). "New developments in multiphoton microscopy." Curr Opin Neurobiol 12(5): 593-601.

Huang, S., Heikal, A. A. and Webb, W. W. (2002). "Two-photon fluorescence spectroscopy and microscopy of NAD (P)H and flavoprotein." Biophys J 82(5): 2811-25.

Jacks, T. and Weinberg, R. A. (2002). "Taking the study of cancer cell survival to a new dimension." Cell 111(7): 923-5.

Jaffe, A. B. and Hall, A. (2005). "RHO GTPASES: Biochemistry and Biology." Annual Review of Cell and Developmental Biology 21(1): 247-269.

Jain, R. K., Munn, L. L. and Fukumura, D. (2002). "Dissecting tumour pathophysiology using intravital microscopy." Nat Rev Cancer 2(4): 266-76.

Jung, J. C. and Schnitzer, M. J. (2003). "Multiphoton endoscopy." Opt Lett 28(11): 902-4.

Katz, A., Savage, H. E., Schantz, S. P., McCormick, S. A. and Alfano, R. R. (2002). "Noninvasive native fluorescence imaging of head and neck tumors." Technol Cancer Res Treat 1(1): 9-15.

Keely, P., Fong, A., Zutter, M. and Santoro, S. (1995). "Alteration of collagen-dependent adhesion, motility, and morphogenesis by the expression of antisense a2 integrin mRNA in mammary cells." J Cell Science 108: 595-607.

Keely, P. J., Rusyn, E. V., Cox, A. D. and Parise, L. V. (1999). "R-Ras signals through specific integrin alpha cytoplasmic domains to promote migration and invasion of breast epithelial cells." J Cell Biol 145(5): 1077-88.

Kirkpatrick, N. D., Zou, C., Brewer, M. A., Brands, W. R., Drezek, R. A. and Utzinger, U. (2005). "Endogenous fluorescence spectroscopy of cell suspensions for chemopreventive drug monitoring." Photochem Photobiol 81(1): 125-34.

Lakowicz, J. R., Szmacinski, H., Nowaczyk, K., Berndt, K. W. and Johnson, M. (1992). "Fluorescence lifetime imaging." Anal Biochem 202(2): 316-30.

Lee, K. C., Siegel, J., Webb, S. E., Leveque-Fort, S., Cole, M. J., Jones, R., Dowling, K., Lever, M. J. and French, P. M. (2001). "Application of the stretched exponential function to fluorescence lifetime imaging." Biophys J 81(3): 1265-74.

Lin, E. Y., Jones, J. G., Li, P., Zhu, L., Whitney, K. D., Muller, W. J. and Pollard, J. W. (2003). "Progression to malignancy in the polyoma middle T oncoprotein mouse breast cancer model provides a reliable model for human diseases." Am J Pathol 163(5): 2113-26.

Lippincott-Schwartz, J. and Patterson, G. H. (2003). "Development and use of fluorescent protein markers in living cells." Science 300(5616): 87-91.

Lippincott-Schwartz, J., Snapp, E. and Kenworthy, A. (2001). "Studying protein dynamics in living cells." Nat Rev Mol Cell Biol 2(6): 444-56.

Marsh, P., Burns, D. and Girkin, J. (2003). "Practical implementation of adaptive optics in multiphoton microscopy." Opt. Express 11: 1123-1130.

Mohler, W., Millard, A. C. and Campagnola, P. J. (2003). "Second harmonic generation imaging of endogenous structural proteins." Methods 29(1): 97-109.

Muti, P. (2004). "The role of endogenous hormones in the etiology and prevention of breast cancer: the epidemiological evidence." Ann N.Y. Acad Sci 1028: 273-82.

Nazir, M. Z., Eliceiri, K. W., Ahmed, A., Hashmi, A., Agarwal, V., Rao, Y., Kumar, S., Lukas, T., Nasim, M., Rueden, C., Gunawan, R. and White, J. G. (2006). "WiscScan: A Software Defined Laser-Scanning Microscope." Scanning: Submitted.

Palmer, G. M., Keely, P. J., Breslin, T. M. and Ramanujam, N. (2003). "Autofluorescence spectroscopy of normal and malignant human breast cell lines." Photochem Photobiol 78(5): 462-9.

Parsons, M., Monypenny, J., Ameer-Beg, S. M., Millard, T. H., Machesky, L. M., Peter, M., Keppler, M. D., Schiavo, G., Watson, R., Chernoff, J., Zicha, D., Vojnovic, B. and Ng, T. (2005). "Spatially distinct binding of Cdc42 to PAK1 and N-WASP in breast carcinoma cells." Mol Cell Biol 25(5): 1680-95.

Paszek, M. J., Zahir, N., Johnson, K. R., Lakins, J. N., Rozenberg, G. I., Gefen, A., Reinhart-King, C. A., Margulies, S. S., Dembo, M., Boettiger, D., Hammer, D. A. and Weaver, V. M. (2005). "Tensional homeostasis and the malignant phenotype." Cancer Cell 8(3): 241-54.

Patterson, G. H., Knobel, S. M., Arkhammar, P., Thastrup, O. and Piston, D. W. (2000). "Separation of the glucose-stimulated cytoplasmic and mitochondrial NAD(P)H responses in pancreatic islet beta cells." Proc Natl Acad Sci USA 97(10): 5203-7.

Peter, M. and Ameer-Beg, S. M. (2004). "Imaging molecular interactions by multiphoton FLIM." Biol Cell 96(3): 231-6.

Peter, M., Ameer-Beg, S. M., Hughes, M. K., Keppler, M. D., Prag, S., Marsh, M., Vojnovic, B. and Ng, T. (2005). "Multiphoton-FLIM quantification of the EGFP-mRFP1 FRET pair for localization of membrane receptor-kinase interactions." Biophys J 88(2): 1224-37.

Pitts, J. D., Sloboda, R. D., Dragnev, K. H., Dmitrovsky, E. and Mycek, M. A. (2001). "Autofluorescence characteristics of immortalized and carcinogen-transformed human bronchial epithelial cells." J Biomed Opt 6(1): 31-40.

Plotnikov, S. V., Millard, A. C., Campagnola, P. J. and Mohler, W. A. (2006). "Characterization of the myosin-based source for second-harmonic generation from muscle sarcomeres." Biophys J 90(2): 693-703.

Poteryaev, D., Squirrell, J. M., Campbell, J. M., White, J. G. and Spang, A. (2005). "Involvement of the Actin Cytoskeleton and Homotypic Membrane Fusion in ER Dynamics in *Caenorhabditis elegans*." Mol. Biol. Cell 16(5): 2139-2153.

Pradhan, A., Pal, P., Durocher, G., Villeneuve, L., Balassy, A., Babai, F., Gaboury, L. and Blanchard, L. (1995). "Steady state and time-resolved fluorescence properties of metastatic and non-metastatic malignant cells from different species." J Photochem Photobiol B 31(3): 101-12.

Ramanujam, N. (2000). "Fluorescence spectroscopy of neoplastic and non-neoplastic tissues." Neoplasia 2(1-2): 89-117.

Rangarajan, A., Hong, S. J., Gifford, A. and Weinberg, R. A. (2004). "Species- and cell type-specific requirements for cellular transformation." Cancer Cell 6(2): 171-83.

Robu, V. G., Pfeiffer, E. S., Robia, S. L., Balijepalli, R. C., Pi, Y., Kamp, T. J. and Walker, J. W. (2003). "Localization of Functional Endothelin Receptor Signaling Complexes in Cardiac Transverse Tubules 10.1074/jbc.M304396200." J. Biol. Chem. 278(48): 48154-48161.

Ronnov-Jessen, L., Petersen, O. W., Koteliansky, V. E. and Bissell, M. J. (1995). "The origin of the myofibroblasts in breast cancer. Recapitulation of tumor environment in culture unravels diversity and implicates converted fibroblasts and recruited smooth muscle cells." J Clin Invest 95(2): 859-73.

Rueden, C., Eliceiri, K. W. and White, J. G. (2004). "VisBio: a computational tool for visualization of multidimensional biological image data." Traffic 5(6): 411-7.

Sahai, E., Wyckoff, J., Philippar, U., Segall, J. E., Gertler, F. and Condeelis, J. (2005). "Simultaneous imaging of GFP, CFP and collagen in tumors in vivo using multiphoton microscopy." BMC Biotechnol 5: 14.

Sato, N., Maehara, N. and Goggins, M. (2004). "Gene Expression Profiling of Tumor-Stromal Interactions between Pancreatic Cancer Cells and Stromal Fibroblasts 10.1158/0008-5472.CAN-04-0677." Cancer Res 64(19): 6950-6956.

Shen, y. r. (1989). "Surface properties probed by second-harmonic and sum-frequency generation." Nature 337(9): 519-525.

Skala, M. C., Squirrell, J. M., Vrotsos, K. M., Eickhoff, J. C., Gendron-Fitzpatrick, A., Eliceiri, K. W. and Ramanujam, N. (2005). "Multiphoton microscopy of endogenous fluorescence differentiates normal, precancerous, and cancerous squamous epithelial tissues." Cancer Res 65(4): 1180-6.

Squirrell, J. M., Eggers, Z. T., Luedke, N., Saari, B., Grimson, A., Lyons, G. E., Anderson, P. and White, J. G. (2006). "CAR-1, a Protein That Localizes with the mRNA Decapping Component DCAP-1, Is Required for Cytokinesis and ER Organization in *Caenorhabditis elegans* Embryos 10.1091/mbc.E05-09-0874." Mol. Biol. Cell 17(1): 336-344.

Squirrell, J. M., Wokosin, D. L., White, J. G. and Bavister, B. D. (1999). "Long-term two-photon fluorescence imaging of mammalian embryos without compromising viability." Nat Biotechnol 17(8): 763-7.

Stoller, P., Kim, B. M., Rubenchik, A. M., Reiser, K. M. and Da Silva, L. B. (2002). "Polarization-dependent optical second-harmonic imaging of a rat-tail tendon." J Biomed Opt 7(2): 205-14.

Strome, S., Powers, J., Dunn, M., Reese, K., Malone, C. J., White, J., Seydoux, G. and Saxton, W. (2001). "Spindle Dynamics and the Role of {gamma}-Tubulin in Early *Caenorhabditis elegans* Embryos." Mol. Biol. Cell 12(6): 1751-1764.

Tadrous, P. J., Siegel, J., French, P. M., Shousha, S., Lalani el, N. and Stamp, G. W. (2003). "Fluorescence lifetime imaging of unstained tissues: early results in human breast cancer." J Pathol 199(3): 309-17.

Tlsty, T. D. and Hein, P. W. (2001). "Know thy neighbor: stromal cells can contribute oncogenic signals." Curr Opin Genet Dev 11(1): 54-9.

van Munster, E. B. and Gadella, T. W. (2005). "Fluorescence lifetime imaging microscopy (FLIM)." Adv Biochem Eng Biotechnol 95: 143-75.

Verveer, P. J., Wouters, F. S., Reynolds, A. R. and Bastiaens, P. I. (2000). "Quantitative imaging of lateral ErbB1 receptor signal propagation in the plasma membrane." Science 290(5496): 1567-70.

Wang, W., Goswami, S., Lapidus, K., Wells, A. L., Wyckoff, J. B., Sahai, E., Singer, R. H., Segall, J. E. and Condeelis, J. S. (2004). "Identification and testing of a gene expression signature of invasive carcinoma cells within primary mammary tumors." Cancer Res 64(23): 8585-94.

Wang, W., Goswami, S., Sahai, E., Wyckoff, J. B., Segall, J. E. and Condeelis, J. S. (2005). "Tumor cells caught in the act of invading: their strategy for enhanced cell motility." Trends Cell Biol 15(3): 138-45.

Wang, W., Wyckoff, J. B., Frohlich, V. C., Oleynikov, Y., Huttelmaier, S., Zavadil, J., Cermak, L., Bottinger, E. P., Singer, R. H., White, J. G., Segall, J. E. and Condeelis, J. S. (2002). "Single cell behavior in metastatic primary mammary tumors correlated with gene expression patterns revealed by molecular profiling." Cancer Res 62(21): 6278-88.

West, R. B., Nuyten, D. S., Subramanian, S., Nielsen, T. O., Corless, C. L., Rubin, B. P., Montgomery, K., Zhu, S., Patel, R., Hernandez-Boussard, T., Goldblum, J. R., Brown, P. O., van de Vijver, M. and van de Rijn, M. (2005). "Determination of stromal signatures in breast carcinoma." PLoS Biol 3(6): e187.

White, J. G., Amos, W. B. and Fordham, M. (1987). "An evaluation of confocal versus conventional imaging of biological structures by fluorescence light microscopy." J Cell Biol 105(1): 41-8.

Williams, R. M., Zipfel, W. R. and Webb, W. W. (2005). "Interpreting second-harmonic generation images of collagen I fibrils." Biophys J 88(2): 1377-86.

Wokosin, D. L., Squirrell, J. M., Eliceiri, K. E. and White, J. G. (2003). "An optical workstation with concurrent, independent multiphoton imaging and experimental laser microbeam capabilities." Review of Scientific Instruments 74(1).

Wozniak, M. A., Desai, R., Solski, P. A., Der, C. J. and Keely, P. J. (2003). "ROCK-generated contractility regulates breast epithelial cell differentiation in response to the physical properties of a three-dimensional collagen matrix." J Cell Biol 163(3): 583-95.

Wozniak, M. A., Kwong, L., Chodniewicz, D., Klemke, R. L. and Keely, P. J. (2005). "R-Ras controls membrane protrusion and cell migration through the spatial regulation of Rac and Rho." Mol Biol Cell 16(1): 84-96.

Zhang, J., Campbell, R. E., Ting, A. Y. and Tsien, R. Y. (2002). "Creating new fluorescent probes for cell biology." Nat Rev Mol Cell Biol 3(12): 906-18.

Zipfel, W. R., Williams, R. M., Christie, R., Nikitin, A. Y., Hyman, B. T. and Webb, W. W. (2003). "Live tissue intrinsic emission microscopy using multiphoton-excited native fluorescence and second harmonic generation." Proc Natl Acad Sci USA 100(12): 7075-80.

Zipfel, W. R., Williams, R. M. and Webb, W. W. (2003). "Nonlinear magic: multiphoton microscopy in the biosciences." Nat Biotechnol 21(11): 1369-77.

Zoumi, A., Yeh, A. and Tromberg, B. J. (2002). "Imaging cells and extracellular matrix in vivo by using second-harmonic generation and two-photon excited fluorescence." Proc Natl Acad Sci USA 99(17): 11014-9.

EXAMPLE 4

Collagen Reorganization Accompanying Invasion

Figure 12:
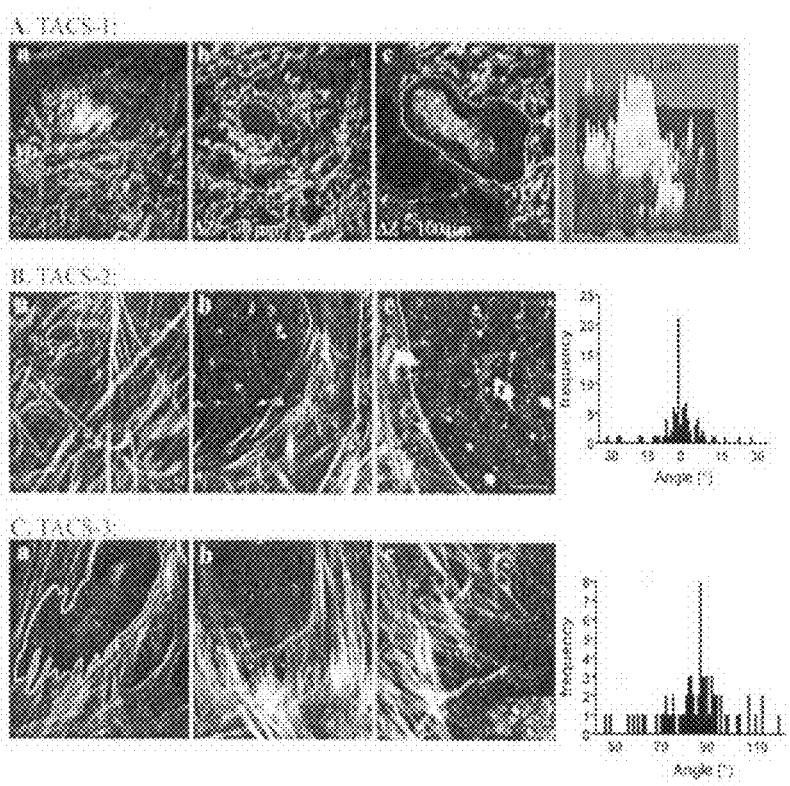
FIG. 12 provides images illustrating the tumor-stromal interaction involved in three Tumor-Associated Collagen Signatures in Wnt-1 mouse tumors.

FIG. 12 provides images illustrating the tumor-stromal interaction involved in three Tumor-Associated Collagen Signatures in Wnt-1 mouse tumors. (A-C) Micrographs illustrating the identified Tumor-Associated Collagen Signatures (TACS): (A. TACS-1) MP/SHG image of TACS-1. Namely, a region of dense collagen (a and surface map) "above" a non-palpable tumor (b-c; yellow outline) that is indicative of the presence of a small tumor. The surface map quantifies the intensity of the fluorescent signal relative to x-y location, and clearly demonstrates an increased collagen signal, and is representative of six Wnt-1 tumors and eight PyVT tumors (not shown) (B. TACS-2) MP/SHG image of the second TACS indicated by the presence of straightened (taut) fibers characteristic of a larger Wnt-1 tumor. (B: a-c) MP/SHG images of collagen fibers in Wnt-1 mice stretched around a relatively smooth tumor boundary as demonstrated by the fact that majority of the fibers are parallel to the tumor boundary. (B: histogram). The angle of collagen fibers relative to a line tangential to the tumor boundary was measured for 86 regions in 6 independent tumors, and graphed as a frequency distribution resulting in a fibers distribution around 0°. (C. TACS-3) The third TACS: aligned collagen fibers at regions of cell invasion in Wnt-1 mice. (C: a-c). The irregular tumor boundary associated with local invasion is outlined in (a; yellow) and connected to fibers that are primarily distributed normal to the initial tumor boundary, represented by a frequency distribution around 90° relative to the tumor boundary. (C: histogram) The angle of collagen fibers relative to a line tangential to the tumor boundary was measured for 71 regions in 6 independent tumors, and graphed as a frequency distribution resulting in a fibers distribution near 90°.

Figure 13:
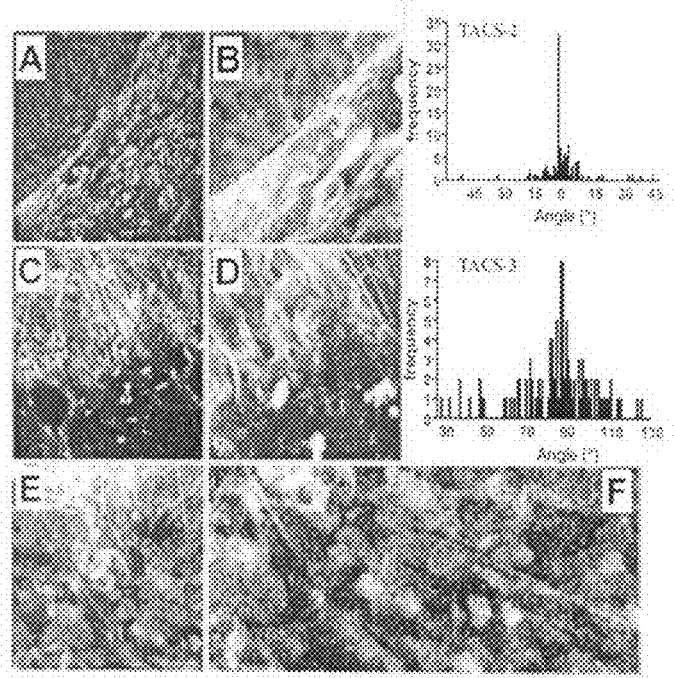
FIG. 13 provides further images illustrating TACS-2 and -3 in the more aggressive PyVT mouse tumor model.

FIG. 13 provides further images illustrating TACS-2 and -3 in the more aggressive PyVT mouse tumor model. (A) TACS-2, with an enlarged cutout region (B) shown at higher brightness and contrast levels and a rough demarcation of the tumor-stromal boundary (red line; s=stroma; t=tumor) to further indicate the wrapping of the collagen parallel to the tumor boundary (distribution near 0°, see top right TACS-2 histogram of 106 regions from eight independent tumors). (C) TACS-3, with an enlarged cutout region (D) shown at higher brightness and contrast levels and a rough demarcation of the tumor-stromal boundary (red line; s=stroma; t=tumor). Note that although some cells have moved past this boundary (examples=x) into the fibers, the boundary serves as a general representation of irregular invasive region into radially aligned collagen fibers (frequency distribution around 90°, see middle right TACS-3 histogram of 109 regions from eight independent tumors).

Furthermore, analysis of TACS-3 regions (E) at higher magnification (F) show endogenous cells associated with fibers at the tumor-stromal boundary and within the tumor. * Indicates examples of fibers interdigitated with the invasive tumor boundary and in contact with the invading tumor cells (red arrows). Scale bar for MP/SHG images equals 25 mm (A-E).

EXAMPLE 5

Collagen Density Promotes Mammary Tumor Initiation and Progression

Abstract

Mammographically dense breast tissue is one of the greatest risk factors for developing breast carcinoma. Despite the strong clinical correlation, breast density has not been causally linked to tumorigenesis, largely because no animal system has existed for studying breast tissue density. Thus, the influence of the extracellular-matrix on breast carcinoma development and the underlying molecular mechanisms are not understood. Importantly, areas of high breast density are associated with increased stromal collagen. In this Example, we demonstrate that increased stromal collagen in mouse mammary tissue increases tumor formation ~3-fold and results in a more invasive phenotype. Using nonlinear optical imaging approaches we demonstrate that local invasion is facilitated by stromal collagen re-organization and that this behavior is increased in collagen dense tissues. Additionally, we identify a metabolic signature in invading metastatic tumor cells and show that increased lung metastases result from tumors that progressed in a collagen-dense microenvironment. To Applicants knowledge, this Example provides the first data causally linking increased stromal collagen to tumor formation and metastasis.

Introduction

Mammographically dense breast tissue is linked to a greater than four-fold increased risk of breast carcinoma[1-3], and is one of the greatest independent risk factors for breast cancer[1,2]. For instance, breast density in more than 50% of the tissue may account for up to 30% of breast cancers, while BRCA1 and BRCA2 mutations, though conferring a greater relative risk, account for only 5% of breast cancers (see Boyd et al[4] and references therein). Furthermore, high breast tissue density is associated with a shift to more malignant tumors[5], and ductal carcinoma in situ (DCIS), a local precursor to some invasive breast cancers, arises overwhelmingly in dense regions of the breast[6]. Breast tissue density, which is additionally increased with hormone replacement therapy[7], is further linked to an increased likelihood of DCIS[5,8], invasive breast carcinoma[8,9], lymphatic and vascular invasions[10], and ~three-fold greater risk of developing a second breast carcinoma[9]. However, although there is considerable correlative data identifying breast density as a risk factor for developing carcinoma, the molecular mechanisms driving breast density-related tumor formation and progression remain largely unknown.

Importantly, areas of increased breast density are not only associated with increased epithelial and stromal cellularity[11-13], but also significantly increased fibrillar collagen deposition[5,12,13]. In addition it has been reported that levels of total collagen increase as radiographic breast tissue density increases[5,12]. This is significant since tissue microenvironments play an important role in maintaining normal cellular behavior[14,15], and stroma surrounding breast epithelial cells is believed to be critically involved in epithelial transformation, carcinoma growth, and metastasis[16-19]. Consistent with this concept, adipose-derived type VI collagen promotes tumor growth[20], while disturbing the epithelial-stromal interaction by disrupting the β1-integrin in mammary epithelial cells inhibits tumorigenesis[21]. A less considered aspect of the complexity of the epithelial-stromal interaction is the fact that the stroma is a dynamic mechanical microenvironment, with dense collagenous stroma transmitting multi-axial deformations to breast cells during tissue deformation and increasing resistance to cellular contractility. Such mechanical signals arising from increased density or rigidity of the microenvironment play a role in the transformed phenotype of breast epithelial cells[22,23]. Hence, although tumor formation is a multistep process involving genetic alterations of the epithelial cell, it has become clear that the epithelial-stromal interaction plays a crucial role in tumor formation and progression. Therefore, due to the increased stroma associated with breast tissue density it is likely that increasing collagen density in the mammary gland would promote tumorigenesis. Although there is a strong correlative link between breast density and carcinoma, to date collagen density has not been causally linked to tumorigenesis, largely because studies utilizing animal models with different stromal density have not been previously performed. In this Example, we demonstrate that mammary tumor formation, invasion, and metastasis are enhanced in collagen-dense stroma in a transgenic mouse model.

Results

Increased Tumor Incidence in Collagen Dense Mammary Tissues

In order to develop a murine tumor model possessing collagen-dense mammary tissue, we examined the mammary tissues from Col1a1$^{tmJae}$ transgenic mice (FIG. 14a). These mice carry mutations near the highly conserved matrix metalloproteinase (MMP) cleavage site for type I collagen (between $Gly_{775}$ and $Ile_{776}$ of the α1(I) chain) that make the collagen resistant to human collagenase digestion[24]. Although an additional cleavage site on type I collagen is vulnerable to rodent collagenase (often termed rat collagenase) and the collagen is susceptible to other proteases[24], these are not sufficient to achieve the proper balance of collagen synthesis and degradation, resulting in excessive collagen accumulation in the skin, uterus, and bone[24]. These phenotypes raised the possibility that the mammary gland, which undergoes dynamic changes in collagen deposition and degradation during development, puberty, and estrous, would rapidly accumulate excess stromal collagen. To explore this possibility, we previously analyzed mammary glands from wild-type, heterozygous, and homozygous Col1a1$^{tmJae}$ mice and reported a greater than 2.5 fold increase in stromal collagen associated with heterozygous and homozygous mice25 (FIG. 14a).

With a defined model for breast tissue density in place, we set out to test the hypothesis that increased mammary collagen density increases tumor formation. Mammary tumors were initiated with the polyomavirus middle-T (PyVT) transgene. This breast tumor model correlates well with many features of human cancer, progresses from hyperplasia to adenoma to early and late carcinoma[26], and is reliably invasive and metastatic[26]. When mice carrying the PyVT transgene under the control of the mammary epithelial-specific MMTV promoter were crossed with heterozygous Col1a1$^{tmJae}$ mice, we observed an approximately three-fold increase in early tumor formation in collagen-dense tissues (FIG. 14b). This trend of increased tumor incidence in collagen-dense glands continued through week 15 (FIG. 14b), with two additional PyVT/Col1a1 mice requiring euthanasia by week 13 due to excessive tumor burden (not shown). Consistent with these observations, quantitative analysis of whole mounts of the 4$^{th}$ mammary gland (n=3 pairs) show significantly increased areas of hyperplasia (FIG. 14c) with collagen-dense tissues showing increased growth out from the gland (FIG. 14c arrowhead and FIG. 14d)). Furthermore, tumors progressing in collagen-dense tissues at 10 weeks had a more invasive morphology (FIG. 14e). Of note is the fact that tumors arising in collagen dense mammary tissue retain increased collagen density (FIG. 14e and confirmed with collagen selective picrosirius red staining: not shown). In fact, collagen levels in PyVT/Col1a1 tumor-bearing glands appear to be increased relative to non-tumor bearing collagen dense glands (FIG. 14e). This observation possibly indicates an amplified shift in the unbalance between collagen synthesis and degradation in the Col1a1 mice following tumor initiation, and may represent an increased desmoplastic response.

Changes in the Tumor-Stromal Interaction Associated with Increased Stromal Collagen Collagen content, fiber structure, and organization are potentially key determinants of tumor cell behavior[25,27]. Therefore, to better understand the tumor-stromal interactions associated with collagen density we employed nonlinear optical imaging of intact live tumors. Multiphoton laser-scanning microscopy (MPLSM) was used to simultaneously generate intrinsic signals from cellular autofluorescence by multiphoton excitation (MPE) and fibrillar collagen by second harmonic generation (SHG)25,28-30. Using this approach described herein (e.g., See examples 1-4) three Tumor-Associated Collagen Signatures (TACS; FIG. 15a) in mammary tumors from both Wnt-1 and PyVT transgenic mice. Specifically, TACS-1: the presence of locally dense collagen (FIG. 15a-i) within the globally increased collagen concentration surrounding tumors, indicated by increased signal intensity (FIG. 15a-iii) at a region near the tumor, which serves as a reliable hallmark for locating small tumor regions (FIG. 15a-ii); TACS-2: straightened (taut) collagen fibers stretched around the tumor, constraining the tumor volume (FIG. 15a-iv and -v); and TACS-3: identification of radially aligned collagen fibers that facilitate local invasion (FIG. 15a-vi). With TACS-3, a distribution of collagen fiber angles around 90° relative to the tumor boundary was indicative of high levels of local invasion while a distribution around 0° was associated with non-invading regions of the tumor[25]. In comparing tumors in the wild-type and heterozygous Col1a1$^{tmJae}$ backgrounds carrying the MMTV-PyVT transgene, we identified critical differences in the temporal progression in density-associated tumors (FIG. 15b-d). At 8 weeks of age, TACS-1 formation in wild-type tumors (FIG. 15bi-ii;) was not yet well developed, and tumors were primarily non-invasive with collagen fibers distributed around 0° (FIG. 15c-d). In contrast, collagen-dense tumors (PyVT/Col1a1) displayed more developed TACS-1 with increased collagen signal and more straightened fibers, indicating early progression to TACS-2 (FIG. 15biii-iv) and some regions of TACS-3 (FIG. 15c). Dense tissues (PyVT/Col1a1) began to show regions of local invasion at 8 weeks (FIG. 15c; highlighted with arrowhead) corresponding to an increased frequency of reorganized collagen fibers with a peak realignment near 90° (FIG. 15d). By 10 weeks of age this difference was enhanced. While tumors from PyVT/wt animals were still largely non-invasive, tumors that arose in collagen-dense tissues continued to have more collagen signal, enhanced realignment to TACS-3, and increased local invasion (FIGS. 15c and d), supporting histological findings shown in FIG. 14e. Moreover, this shift in the temporal onset of TACS-3 to an earlier occurrence in collagen-dense tumors indicates the more advanced and invasive state of these tumors.

Figure 15:
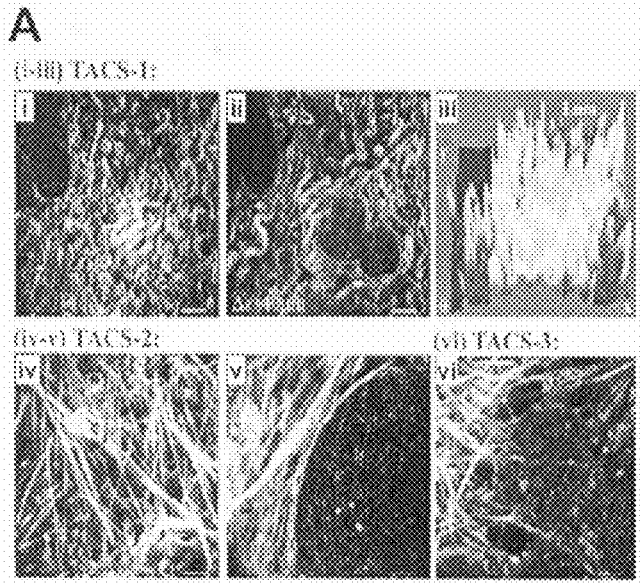
FIG. 15. Tumor-associated collagen signatures (TACS) and Increased Local Invasion with High Collagen Density. (a) Example of TACS-1 (i-iii). A region of locally dense collagen (i) near a small tumor region (ii) that is within the globally increased collagen region surrounding tumors, resulting from increased SHG (collagen) signal intensity (iii; 3D surface plot of luminescence (Lum) showing an ~3-fold signal increase at TACS-1). Example of TACS-2 (iv-v), showing straightened (taut) collagen fibers stretched around and constraining an expanded epithelial tumor volume. At regions of TACS-2, quantitative analysis[25] of fiber angles relative to the tumor boundary shows a distribution of fibers around 0° that correlates to non-invading regions of tumor cells. Example of TACS-3 (vi), showing radially aligned collagen fibers, reorganized by tumor cells, at regions of tumor cell invasion. At regions of TACS-3, quantitative analysis[25] of fiber angles relative to the tumor boundary shows a distribution of fibers around 90° that correlates with local invasion of tumor cells. (b) TACS-1 in 8 week old normal (wt; i-ii) and collagen dense (Col1a1; iii-iv) tumors showing more developed TACS-1 associated with density (early transition between TACS-1 and -2) while showing very early TACS-1 formation in wild-type tumors (yellow arrowheads; white arrowhead indicates a TACS-1 region that is not shown since it is out of the focal plane). The displayed tumor regions (i and iii) are at a $\Delta z=40$ µm from collagen signatures (ii and iv). Note the increased endogenous cellular autofluorescence associated with tumor cells in collagen-dense tissues when PyVT/wt (ii) and PyVT/Col1a1 (iv) tumors were imaged sequentially at the same power settings (ii versus iv). Representative of n=4 pairs of tumors. (c) Tumors were imaged and MPE (red) and SHG (green) signals were separated. Top panels: 8 week old tumors showing early TACS-3 regions and some local invasion in collagen dense tumors (PyVT/Col1a1) while PyVT/wt tumors were still primarily bound by collagen (TACS-2) and non-invasive. Bottom panels: 10 week old tumors from dense tissues (PyVT/Col1a1) displayed further regions of TACS-3 progression and an invasive phenotype, compared to control tissues (PyVT/wt) that were largely non-invasive and had little collagen reorganization. Representative of n≧6 tumors from each background. (d) Quantitative analysis of collagen fiber angles relative to the tumor boundary for 8 week (top) and 10 week (bottom) old animals. PyVT/wt animals displayed little TACS-3 and are primarily non-invasive with only 23% (8 weeks) and 24% (10 weeks) of their fibrils having angles outside of the TACS-2 distribution around 0° (i.e. <−15° or >15°). In contrast PyVT/Col1a1 tumors had some regions of TACS-3 (distribution around 90°) and local invasion with 46% of the fibril distributed outside of the TACS-2 distribution (0°) at 8 weeks. At 10 weeks, PyVT/Col1a1 tumors were more invasive and had a broader distribution of TACS-3 with 51% of fiber angles outside of the TACS-2 distribution. Calculated from ≧185 of tumor regions from ≧6 separate tumors. All scale bars=25 µm.
Figure 15:
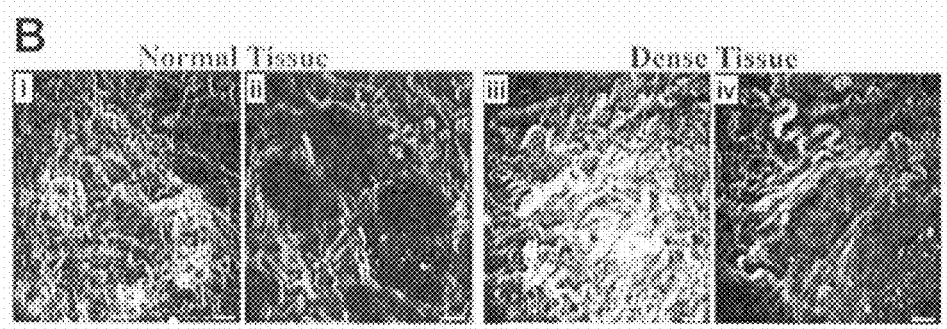
Figure 15:
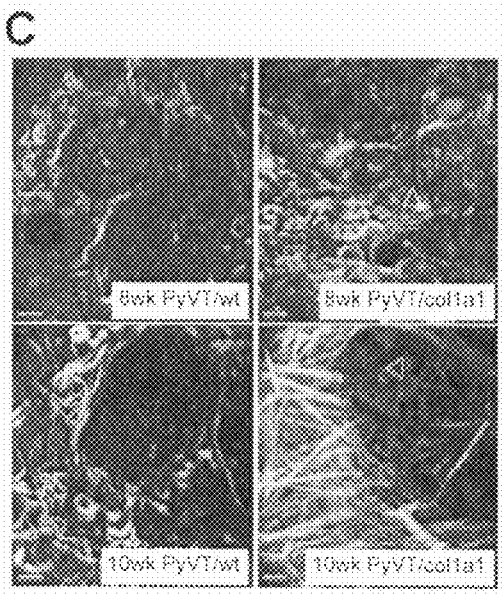
Figure 15:
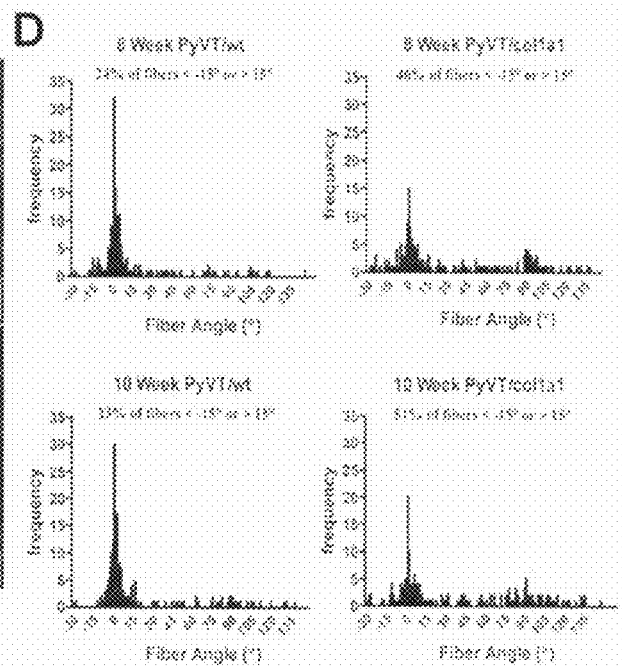
Figure 16:
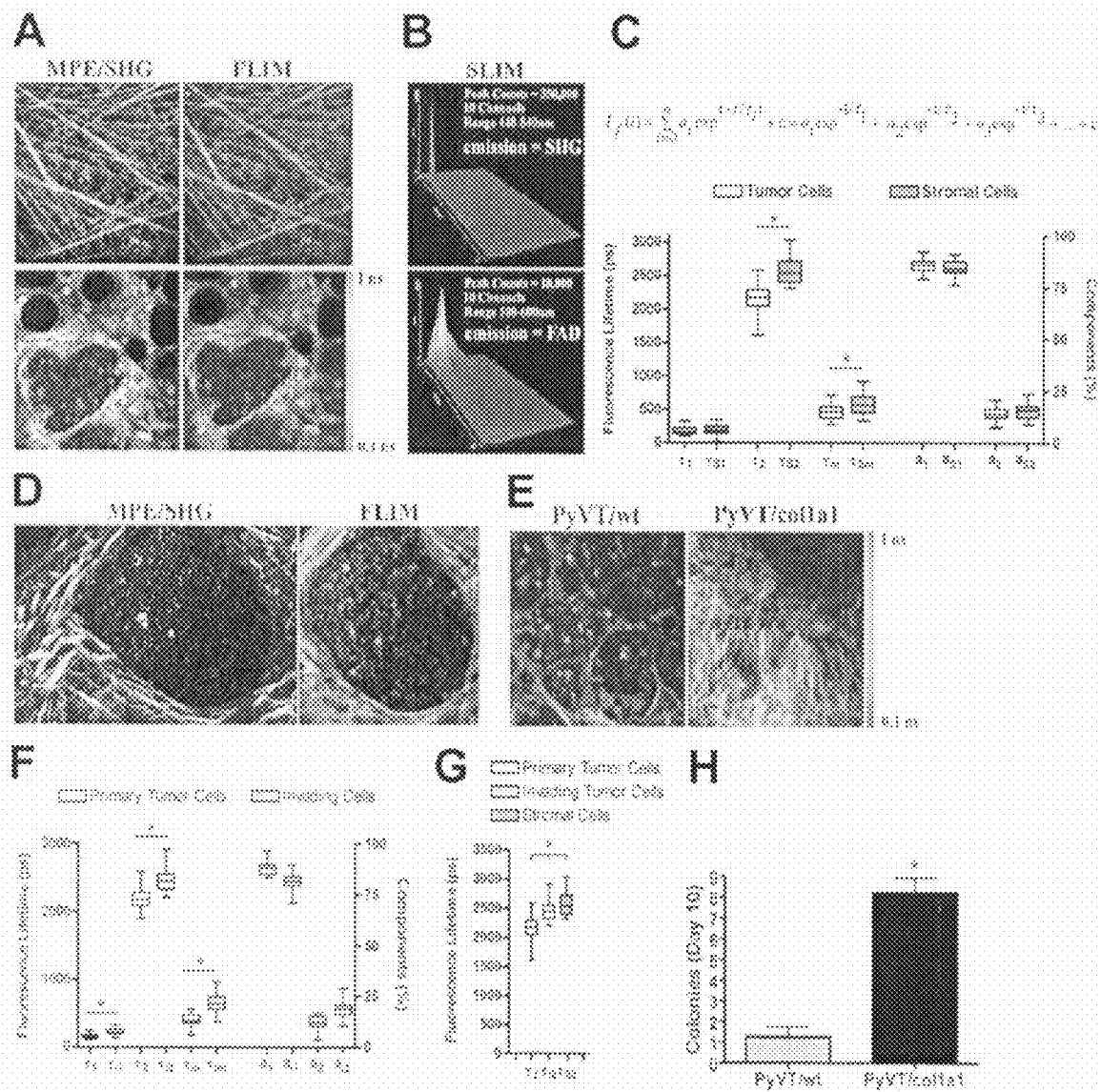
FIG. 16. FLIM and SLIM Analysis of Invading Tumor Cells. (a) Multiphoton intensity and fluorescence lifetime imaging microscopy (FLIM) images of the stroma near a tumor (top) and the tumor and stromal components (bottom) from wild-type tumors showing the utility of FLIM to image tumor cells, stromal cells, and extracellular matrix components. Note the increased intensity and fluorescent lifetimes of stromal cells (quantified in c) and the low lifetime of collagen (matching system response, i.e. no actual lifetime). The color map in (a) represents the weighted average of the two-term model components $[\tau_m=(a_1\tau_1+a_2\tau_2)/(a_1+a_2)]$ using the equation shown in (c). (b) Multiphoton spectral lifetime imaging microscopy (SLIM) analysis of the emission spectrum from endogenous fluorescence resulting from excitation at 890 nm. The emission signals were separated by 10 nm spectral steps over 16 channels (10 channels are displayed) and the photons collected in each channel used to generate fluorescence lifetime images and signals for each channel plotted with SLIM-Plotter (shown). Emission from collagen (at half of the input wavelength) showed a very strong and sharp signal with a no appreciable decay (lifetime) confirming the SHG nature of the collagen signal (top). Emission spectra of endogenous fluorescence from tumor and stromal cells showed that the only substantial emission signal is at 530 nm, indicating that the source of the autofluorescence signal is FAD, and not NADH or tryptophan[50], with lifetime values from the 530 channel matching values obtained with FLIM. (c) Quantitative analysis of fluorescent lifetime components from tumor and stromal (subscript s) cells using the equation shown. Note the increase in the second (long) component and weighted mean component (see equation above) for stromal cells when compared to cells from the primary tumor mass. Note, ≧30 measurements per tumor image from 4 independent tumors were used to calculate lifetime values for tumor cells in the primary tumor mass while ≧6 measurements per tumor image from 4 independent tumors were used for stromal cells. (d) Intensity and FLIM images of cells away from and near invasive TACS-3 regions showing increased fluorescent intensity and lifetime near invasive regions (left side of images). (e) FLIM images of tumors from 10 week old PyVT/wt and PyVT/Col1a1 animals confirming the increased TACS-3 for collagen dense tumors shown in FIG. 15. Note the increased fluorescent lifetimes for invading cells (right panel) quantified in f. Like stromal cells the second (long) and mean component are increased in invading cells. However, the short component is also increased in invading cells when compared to cells in the primary tumor mass. Note, 45 measurements for cells within the primary tumor mass and 45 measurements for invading cells adjacent to the tumor primary tumor mass were used to calculate lifetime values. (g) The second (long) component from cells with the primary tumor mass, invading tumor cells, and stromal cells showing a progressive increase as cells move from a primary epithelial tumor phenotype to a more mesenchymal phenotype. (h) 3D tumor cell invasion assay showing that tumor explants from collagen dense tumors (PyVT/Col1a1) resulted in more invasion into 3D collagen gels and colony formation after 10 days than explants from PyVT/wt tumors (mean ±SEM; n=4 PyVT/wt and n=14 PyVT/Col1a1 tumor explants from four sibling mice). *Indicates a statistically significant (p<0.05) difference following analysis with 1-way Analysis of Variance (ANOVA) with a post-hoc Tukey-Kramer test for c, f, and g, and a paired t-test for h.
Figure 18:
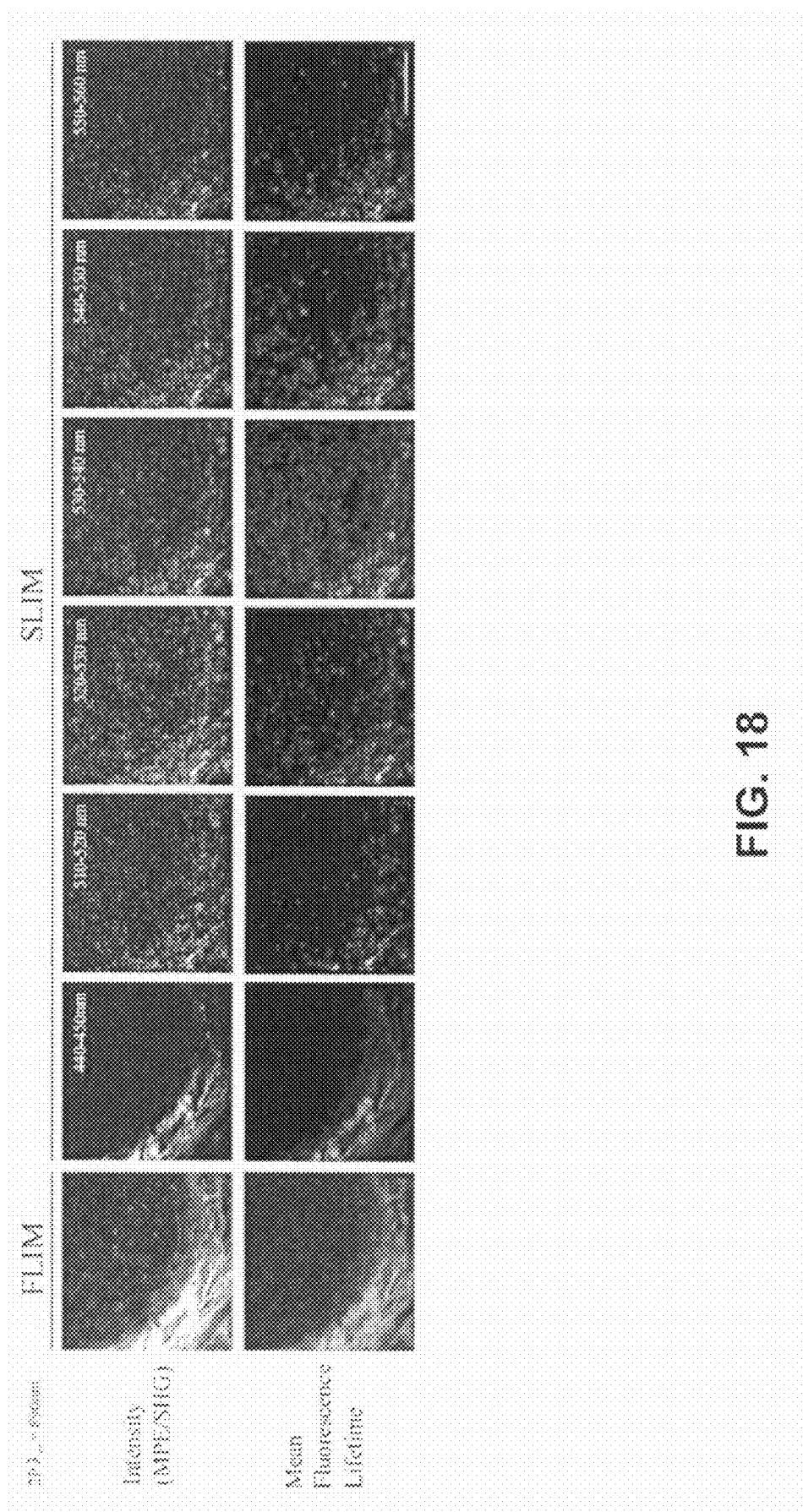
FIG. 18. Multiphoton intensity and fluorescence lifetime imaging microscopy (FLIM) images and Multiphoton spectral lifetime imaging microscopy (SLIM) images of FIG. 19. Use of MPLSM, and SHG to better image tumor-associated changes in collagen fibers (green in F) and invading cells at the tumor/stromal boundary.

In concert with changes in the alignment of stromal collagen and increased local invasion, higher cellular autofluorescence intensity was observed in stromal cells and invading tumor cells when compared to cells in the primary tumor mass (FIGS. 15 and 16). To examine these progression-associated changes in more detail, we imaged the tumors with multiphoton fluorescence lifetime imaging microscopy (FLIM) and spectral lifetime imaging microscopy (SLIM). Using these techniques, we were able to further confirm the presence of collagen, which has a theoretical zero lifetime that experimentally equals the system signal response due to background noise (100 ns (blue) in FIG. 16a). The spectral properties of the endogenous cellular fluorophore identify it as FAD (FIG. 16b and FIG. 18).

Exploiting cellular FAD as an endogenous biomarker to visualize cells, we further explored the difference in FAD signal between stromal and tumor cells, using FLIM. Differences in the fluorescence lifetime of FAD between primary tumor cells and stromal cells were color mapped (FIG. 16a) and quantified (FIG. 16c). Stromal cells possessed a higher second component ($\tau_2$) and weighted mean ($\tau_m$) of the fluorescent lifetime, allowing stromal cells to be easily differentiated from epithelial tumor cells (FIGS. 16a and c). Interestingly, invading cells displayed a fluorescent intensity more closely resembling stromal cells than cells from the primary tumor mass (FIGS. 16d and e). Consistent with this finding, changes in fluorescent intensity and fluorescent lifetimes of NADH and tryptophan have also been associated with cells of differing metastatic potential[31]. Because invading tumor cells commonly undergo an epithelial-to-mesenchymal transition (EMT), it is possible that shifts in the fluorescent lifetime may be indicative of EMT. In fact, higher FAD fluorescent intensity was observed in cells near invading regions when compared to non-invading regions (FIG. 16d) while invading tumor cells showed a longer FAD fluorescent lifetime (FIG. 16e—right panel), having higher first ($\tau_1$), second ($\tau_2$), and weighted mean ($\tau_m$) lifetime components (FIG. 16f), and could be differentiated from stromal cells and cells in the primary tumor mass. Additionally, examination of $\tau_2$ values indicates a progressive increase in lifetimes from cells within the tumor mass to invading cells to stromal cells (FIG. 16g) supporting the idea that an EMT may be taking place.

Increased Invasion and Metastasis Associated with Dense Stromal Collagen

In addition to identifying key differences in measurable fluorescent intensity and lifetime associated with invading cells, FLIM analysis confirmed results shown in FIG. 15 demonstrating a shift towards TACS-3 and increased local invasion with higher collagen density (see FIG. 16e). Invading cells associated with TACS-3 could be clearly differentiated in collagen-dense tissues (FIG. 16e—right panel) while PyVT/wt tumors (FIG. 16e—left panel) were non-invasive at this stage (week 10). Confirmation of increased invasion in tumors that arose in collagen-dense tissue was obtained by examining invasion from tumor explants into 3D collagen gels. Tumor explants of defined size were placed into 3D collagen gels and the number of distant colonies was counted. After 10 days in culture, explants from collagen-dense tissues resulted in significantly more colonies (FIG. 16h) corroborating data from live tissues (FIGS. 15 and 16) that tumors associated with collagen dense tissues are more invasive.

Figure 14:
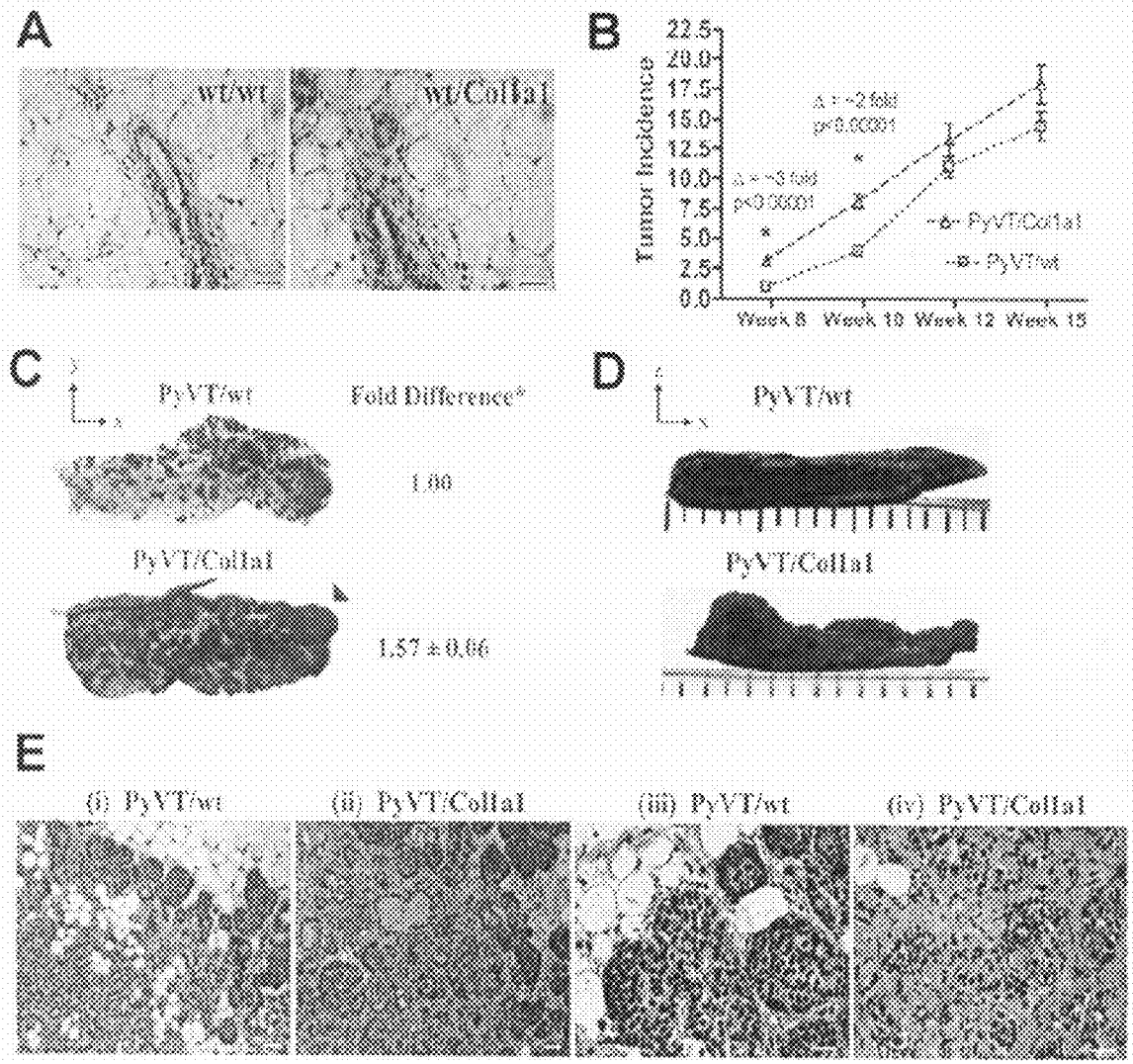
FIG. 14. High mammary collagen density promotes tumor formation. (a) Histology of mammary glands from 10-week-old wild-type and heterozygous Col1a1$^{tmJae}$ mice showing increased stromal collagen and hypercellularity associated with the Col1a1$^{tmJae}$ mouse model. Scale bar=25 µm. (b) Significantly increased tumor incidence in collagen dense (Col1a1) mammary glands. (c) Whole mount preparations of the 4th inguinal mammary glands from PyVT/wt and PyVT/Col1a1 mice at 10 weeks of age. Quantitative analysis of the area of hyperplasia from three pairs of glands calculated from a common threshold value set with density slicing in ImageJ software revealed a greater than 1.5-fold increase in hyperplasia associated with increased stromal collagen (t-test: p=0.03). Additionally, at age-matched time points, tumors in mice with dense stroma not only displayed more hyperplastic area but also tumor regions that grew out away from the gland (arrow in c; and d). (e) Low (i-ii) and high (iii-iv) magnification images of H&E stained histology sections from 10 week old mice showing increased collagen in PyVT/Col1a1 tumors (ii and iv) and a more invasive phenotype when compared to PyVT/wt (i and iii) tumors. Scale bars=50 µm (i-ii) and 25 µm (iii-iv).
Figure 17:
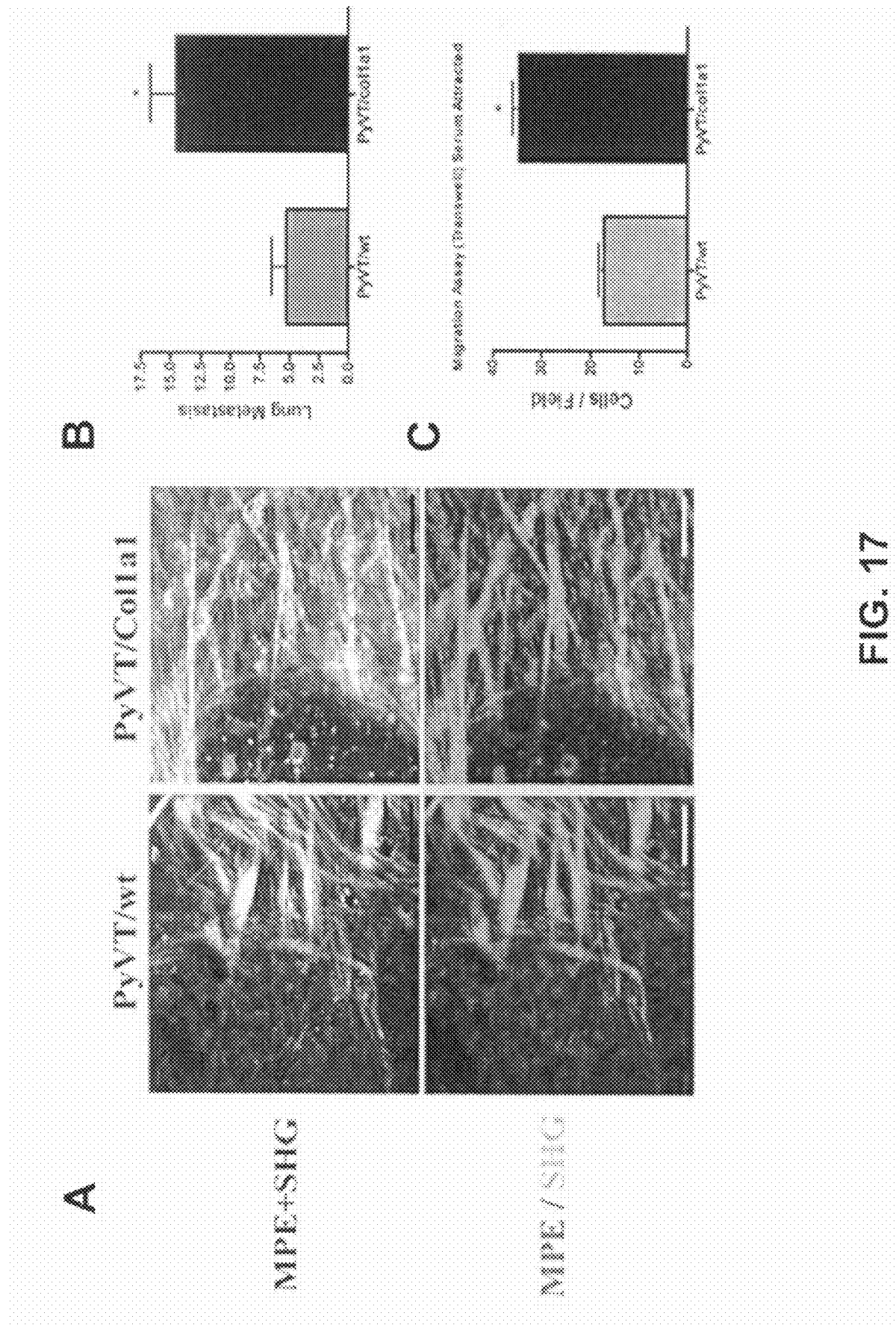
FIG. 17. Increased Metastasis Associated with Dense Stromal Collagen. (a) Combined and signal separated MPE/SHG images of late stage (15 week) invasive PyVT/wt and PyVT/Col1a1 tumors. Note that tumors arising in either wt or Col1a1 backgrounds are invasive at 15 weeks and display significant regions of TACS-3. Scale bars=25 µm. (b) Increased lung metastasis at 15 weeks in mice that formed tumors in collagen-dense mammary glands (PyVT/Col1a1) when compared to mice that formed tumors in control glands (PyVT/wt). (c) Tumor cells extracted from collagen dense tumors (PyVT/Col1a1) showed increased migration when compared to tumor cells from control tumors (PyVT/wt) as measured by transwell migration assays with serum as the chemotractant. *Indicates a statistically significant (p<0.05) following analysis with paired t-tests.

Examination of later stage tumors (week 15) demonstrated that both PyVT/wt and PyVT/Col1a1 tumors were invasive and possessed regions of TACS-3 mediated invasion (FIG. 17a), confirming an earlier report that late stage wild-type PyVT tumors have invasiveness associated with TACS-3[25]. Moreover, since the MMTV-PyVT tumor model reliably results in lung metastases we examined lung tissue in late stage mice (week 15). In animals in which tumors were initiated and progressed in a collagen-dense microenvironment, significantly increased lung metastases were observed (FIG. 17b). This raised the possibility that increased lung metastasis may be the result of a more invasive and migratory cell population, or may result from the earlier onset of invasiveness as seen in FIGS. 14-16. To address this question, we isolated tumor cells and performed migration assays over the first 24 hours following tumor harvest. Tumor cells isolated from collagen-dense tissues were in fact more migratory (FIG. 17c), indicating that the earlier onset of invasiveness is likely not the sole cause for increased metastasis but that the tumor cells themselves are more invasive (FIG. 16h) and migratory (FIG. 17c).

Discussion

Although the increased risk for breast carcinoma associated with collagen-dense breast tissue has been described[1-3], little is known of the molecular mechanisms underlying increased collagen deposition and its influence on the interactions between stromal collagen, fibroblasts, and epithelial cells, nor how increased collagen affects tumorigenesis. This is due in large part to the fact that no animal model system had previously existed to study these phenomena in vivo. Herein we demonstrate that mice with increased stromal collagen have increased mammary tumors that are more invasive and metastatic, consistent with reports of the human carcinoma progression.

As discussed throughout this description, the use of collagen alignment to quantify local invasion with the level of TACS-2 (alignment tangential to the tumor boundary at a 0° angle) and TACS3 (alignment radial to the tumor boundary at an angle of 90°) providing a novel quantitative assessment of tumor progression[25]. In this study, the analysis of collagen radial alignment in samples from 8 and 10 week tumors demonstrates a transition from TACS-2 to TACS-3. We observe a broad distribution of fiber angles away from zero but not yet tightly grouped at the radial alignment (90°) associated with a high degree of local invasion previously reported for 15 week tumors[25]. This result suggests that the move toward invasive behavior is a transitional process increasing with time. We find that tumor cells in collagen-dense tumors are not only more invasive and metastatic in vivo, but were also more invasive and migratory in vitro (FIG. 16h and FIG. 17c), indicating that the increased invasiveness is not only the result of earlier tumorigenesis that had more time to progress, but also due to tumor cells that are fundamentally more invasive because they arose within collagen-dense tissues. This finding suggests that cellular behavior is altered by epigenetic changes signaled from the collagen-dense stroma, consistent with findings that increased collagen density alters epithelial cell signaling and behavior in vitro23.

Herein the data have demonstrated that increased stromal collagen in the mammary gland is part of a mechanism that results in increased tumorigenesis and a more invasive phenotype. This may be the result of two likely mechanisms. The first is that increased breast density is associated with a stiffer extracellular matrix resulting in high local mechanical loads and higher resistance to cellular contractility for breast epithelial cells. Such changes in the physical microenvironment has been shown to alter focal adhesion and Rho GTPase signaling, resulting in a more transformed phenotype[22,23]. A second, and more indirect mechanism may be the influence of increased stromal collagen on mammary fibroblasts that in turn influence epithelial cells. Stromal fibroblasts can regulate epithelial cells in part through secretion of specific soluble growth factors and chemokines[19,32-34]. For instance, TGF-β has been associated with reactive stroma, fibrosis, and epithelial cell invasion[35], while numerous studies indicate that the epidermal growth factor (e.g. EGFR, HER-2/neu/ErbB2, ErbB3 etc.), insulin-like growth factor (e.g. IGF-I, IGFBP3, etc.), and hapatocyte growth/scatter factor (HGF/SF, c-Met) systems are important not only in the normal mammary gland but also during tumorigenesis and metastasis[34,36-39]. Furthermore, the IGF family has been implicated in association with dense breast tissue[13,40,41] with both local[13] and circulating[40,41] levels of IGF-I positively correlated with breast tissue density. In fact, both of these mechanisms are plausible and are likely to be acting in concert with one another to produce fundamental changes in both the breast epithelial and stromal cells. Since both adhesion-mediated and growth factor-mediated signaling pathways are often interrelated[42-47], understanding each of these possible mechanisms and their convergence is likely to be of great importance to understanding breast tissue density-related carcinoma.

In conclusion, increased collagen density increases tumorigenesis, local invasion, and metastasis, causally linking increased stromal collagen to tumor formation and progression. Imaging with combined MPE and SHG in tumors allows visualization of cellular autofluorescence and defined collagen structures that identify key differences associated with high collagen density and may provide useful diagnostic tools to rapidly assess fresh tissue biopsies. Furthermore, imaging live tissues with FLIM and SLIM confirms results obtained with MPE/SHG and identifies significant differences in fluorescence lifetimes that are indicative of invasive cells. As demonstrated herein FLIM and SLIM may serve as tools to evaluate the invasiveness of tumor cells in mammary tissues. Given the significant findings associated with high breast tissue density and the now available utility of a mouse model for breast tissue density, fundamental questions regarding the molecular mechanisms associated with breast tissue density-related carcinoma can now be further addressed in vivo.

Methods

Mice. The University of Wisconsin animal use and care committee approved this study. Breeding pairs of Col1a1$^{tmJae}$ mice[24] in the B6/129 background were obtained from Jackson Laboratory. Male FVB Polyomavirus middle-T mice under the control of the mammary specific MMTV promoter were originally obtained from Dr. Amy Moser (University of Wisconsin) and are abbreviated PyVT following the Jackson Laboratory (from which they originated) nomenclature, but are also commonly abbreviated as PyMT or PyV MT. Col1a1$^{tmJae}$ homozygote males were crossed to C57BL/6 females to generate heterozygous females that were crossed to PyVT males to generate mice with normal and collagen dense mammary tissues carrying the polyoma transgene. Genotyping by PCR was performed on DNA extracted from tail biopsies (Wizard SV Genomic DNA Purification System, Promega, Madison, Wis.) using primers indicated in the strain information provided by The Jackson Laboratory. Mice were examined for palpable tumors starting at seven weeks of age and euthanized at 15 weeks or when the tumor burden became excessive.

Histology and Mammary Gland Whole Mounts. Selected mammary tissues and tumors were fixed in 4% paraformaldehyde in PBS followed by paraffin-embedding. Additionally, all tissues imaged with multiphoton microscopy were subsequently fixed and processed for histology. Tissue sections were stained with hematoxylin and eosin (H&E) with adjacent sections stained with the selective collagen stain, picrosirius red. Mammary whole mounts were prepared by fixing tissues in Carnoy's solution (10% glacial acetic acid/ 30% chloroform/60% absolute ethanol), followed by rehydration and staining with carmine alum. Tissues were then dehydrated, cleared with xylene, and mounted.

Multiphoton Laser-Scanning Microscopy (MPLSM). For live tissue imaging by multiphoton excitation (MPE) and second harmonic generation (SHG), mammary tumors were harvested and live tissue maintained in buffered media at 37° C. All tissues were imaged immediately following tissue harvest using an Optical Workstation[25] that was constructed around a Nikon Eclipse TE300. A 5W mode-locked Ti:sapphire laser (Millennium/Tsunami, Spectra-Physics, Mountain View, Calif.) excitation source producing around 100 fs pulse widths and tuned to 890 nm was utilized to generate both MPE and SHG. The beam was focused onto the sample with a Nikon 60× Plan Apo water-immersion lens (N.A.=1.2). All SHG imaging was detected from the back-scattered SHG signal[48], and the presence of collagen confirmed in our tissues using fluorescence lifetime imaging microscopy (FLIM) on the same optical workstation, since the SHG from collagen has no lifetime. Furthermore, due to the fundamentally different physical behavior of MPE and SHG, signals could be discriminated by filtering the emission signal. We used a 464 nm (cut-on) long pass to isolate the emission from autofluorescence from the conserved 445 nm SHG emission. A 445 nm (narrow band pass) filter was therefore used to isolate the SHG emission. Acquisition was performed with WiscScan a software acquisition package developed at LOCI (Laboratory for Optical and Computational Instrumentation, University of Wisconsin, Madison, Wis.) and image analysis for MPE/SHG was performed with Imagej and VisBio software. For TACS-1 image analysis additional surface rendering plug-ins for Imagej were utilized (see http://rsb.info.nih.gov/ij/). For TACS-2 and -3, Imagej was used to quantify the collagen fiber angle relative to the tumor. The tumor boundary was defined and the angle relative to the tangent of tumor boundary was measured every 10 microns as previously reported[25].

Fluorescence and Spectral Lifetime Imaging Microscopy (FLIM and SLIM). FLIM was performed on live tissue with the Optical workstation described above as previously described[25]. Briefly, the 5W Ti:sapphire laser (Millennium/Tsunami, Spectra-Physics, Mountain View, Calif.) was tuned to 890 nm with the beam focused onto the sample with a Nikon 60× Plan Apo water-immersion lens (N.A.=1.2). Intensity and FLIM data were collected by a H7422 GaAsP photon-counting PMT (Hamamatsu, Bridgewater, N.J.) connected to a time correlated single photon counting (TCSPC) system (SPC-730, Becker & Hickl, Berlin, Germany). Multiphoton SLIM was performed using a second generation system that evolved from a previously described instrument[49] built around an inverted microscope (Eclipse TE2000, Nikon, Melville, N.Y.). Briefly, an 8-W solid-state Ti:Sapphire mode-locking laser (Coherent Mira, Coherent, Santa Clara, Calif.) was used to generate pulse widths of approximately 120 fs at a repetition rate of 76 MHz. Intensity and fluorescence lifetime data were collected over 16 individual 10 nm spectral-width channel using a 16-anode photon counting linear PMT array (PML-16, Becker & Hickl) connected to a TCSPC system (SPC-830, Becker&Hickl). Fluorescent lifetime analysis from FLIM and SLIM was carried out with SPCImage (Becker & Hickl) as well as with a LOCI created computational tool, SlimPlotter, which allows visualization and analysis of the lifetimes by spectral channel.

3D Invasion Assay. Uniform sized tumor explants were harvested from intact tumors using a tissue biopsy punch (3 mm diameter), rinsed with PBS (containing 100 units penicillin/100 ug streptomycin/0.25 ug/mL amphotericin B), and placed into 2.0 mg/mL collagen gels (BDBioscience, San Diego, Calif.) that were neutralized with 2× HEPES buffer. Tumors were maintained in collagen gels floated in DMEM containing 5% FBS, penicillin (100 units), streptomycin (100 ug), and amphotericin B (0.25 ug/mL) for 10 days over which time the number of distant multicellular colonies were counted.

Lung metastasis. Lungs from PyVT/wt and PyVT/Col1a1 mice (as well as wt/wt and wt/Col1a1 as negative controls) were harvested at 15 weeks, fixed in formalin, and processed for histology. Sections were cut every 50 μm through the entire tissue and sections stained with hematoxylin and eosin. Total lung metastases over all sections were then counted.

Isolation of tumor cells and migration assay. Tumors from PyVT/wt and PyVT/Col1a1 backgrounds we minced and digested with 2 mg/mL collagenase and 10 μg/mL hyaluronidase in DMEM containing penicillin (100 units), streptomycin (100 ug), and amphotericin B (0.25 ug/mL). Following gentle shaking at 37° C. for three hours, cell were pelleted, washed, and plated in DMEM containing 5% FBS. Thirty-six hours post-harvest the tumor cells were transferred in to Transwell plates (Corning Inc., Corning, N.Y.) using serum and soluable collagen containing media as the chemotractant.

Statistical Analysis. For multi-group comparisons, one-way Analysis of Variance (ANOVA) with a post-hoc Tukey-Kramer test was used. For two-group comparisons t-testing was performed.

REFERENCES

1. McCormack, V. A. & dos Santos Silva, I. Breast density and parenchymal patterns as markers of breast cancer risk: a meta-analysis. *Cancer Epidemiol Biomarkers Prev* 15, 1159-69 (2006).
2. Boyd, N. F., Lockwood, G. A., Byng, J. W., Tritchler, D. L. & Yaffe, M. J. Mammographic densities and breast cancer risk. *Cancer Epidemiol Biomarkers Prev* 7, 1133-44. (1998).
3. Boyd, N. F., Martin, L. J., Stone, J., Greenberg, C., Minkin, S. & Yaffe, M. J. Mammographic densities as a marker of human breast cancer risk and their use in chemoprevention. *Curr Oncol Rep* 3, 314-21. (2001).
4. Boyd, N. F., Rommens, J. M., Vogt, K., Lee, V., Hopper, J. L., Yaffe, M. J. & Paterson, A. D. Mammographic breast density as an intermediate phenotype for breast cancer. *Lancet Oncol* 6, 798-808 (2005).
5. Alowami, S., Troup, S., Al-Haddad, S., Kirkpatrick, I. & Watson, P. H. Mammographic density is related to stroma and stromal proteoglycan expression. *Breast Cancer Res* 5, R129-35 (2003).
6. Ursin, G., Hovanessian-Larsen, L., Parisky, Y. R., Pike, M. C. & Wu, A. H. Greatly increased occurrence of breast cancers in areas of mammographically dense tissue. *Breast Cancer Res* 7, R605-8 (2005).
7. Rutter, C. M., Mandelson, M. T., Laya, M. B., Seger, D. J. & Taplin, S. Changes in breast density associated with initiation, discontinuation, and continuing use of hormone replacement therapy. *Jama* 285, 171-6. (2001).
8. Gill, J. K., Maskarinec, G., Pagano, I. & Kolonel, L. N. The association of mammographic density with ductal carcinoma in situ of the breast: the Multiethnic Cohort. *Breast Cancer Res* 8, R30 (2006).
9. Habel, L. A., Dignam, J. J., Land, S. R., Salane, M., Capra, A. M. & Julian, T. B. Mammographic density and breast cancer after ductal carcinoma in situ. *J Natl Cancer Inst* 96, 1467-72 (2004).
10. Aiello, E. J., Buist, D. S., White, E. & Porter, P. L. Association between mammographic breast density and breast cancer tumor characteristics. *Cancer Epidemiol Biomarkers Prev* 14, 662-8 (2005).
11. Hawes, D., Downey, S., Pearce, C. L., Bartow, S., Wan, P., Pike, M. C. & Wu, A. H. Dense breast stromal tissue shows greatly increased concentration of breast epithelium but no increase in its proliferative activity. *Breast Cancer Res* 8, R24 (2006).
12. Li, T., Sun, L., Miller, N., Nicklee, T., Woo, J., Hulse-Smith, L., Tsao, M. S., Khokha, R., Martin, L. & Boyd, N. The association of measured breast tissue characteristics with mammographic density and other risk factors for breast cancer. *Cancer Epidemiol Biomarkers Prev* 14, 343-9 (2005).
13. Guo, Y. P., Martin, L. J., Hanna, W., Banerjee, D., Miller, N., Fishell, E., Khokha, R. & Boyd, N. F. Growth factors and stromal matrix proteins associated with mammographic densities. *Cancer Epidemiol Biomarkers Prev* 10, 243-8. (2001).
14. Barcellos-Hoff, M. H., Aggeler, J., Ram, T. G. & Bissell, M. J. Functional differentiation and alveolar morphogenesis of primary mammary cultures on reconstituted basement membrane. *Development* 105, 223-35. (1989).
15. Keely, P., Fong, A., Zutter, M. & Santoro, S. Alteration of collagen-dependent adhesion, motility, and morphogenesis by the expression of antisense α2 integrin mRNA in mammary cells. *J Cell Science* 108, 595-607 (1995).

16. Tlsty, T. D. & Hein, P. W. Know thy neighbor: stromal cells can contribute oncogenic signals. *Curr Opin Genet Dev* 11, 54-9 (2001).
17. Noel, A. & Foidart, J. M. The role of stroma in breast carcinoma growth in vivo. *J Mammary Gland Biol Neoplasia* 3, 215-25. (1998).
18. Elenbaas, B., Spirio, L., Koerner, F., Fleming, M. D., Zimonjic, D. B., Donaher, J. L., Popescu, N. C., Hahn, W. C. & Weinberg, R. A. Human breast cancer cells generated by oncogenic transformation of primary mammary epithelial cells. *Genes Dev* 15, 50-65. (2001).
19. Orimo, A., Gupta, P. B., Sgroi, D. C., Arenzana-Seisdedos, F., Delaunay, T., Naeem, R., Carey, V. J., Richardson, A. L. & Weinberg, R. A. Stromal fibroblasts present in invasive human breast carcinomas promote tumor growth and angiogenesis through elevated SDF-1/CXCL12 secretion. *Cell* 121, 335-48 (2005).
20. Iyengar, P., Espina, V., Williams, T. W., Lin, Y., Berry, D., Jelicks, L. A., Lee, H., Temple, K., Graves, R., Pollard, J., Chopra, N., Russell, R. G., Sasisekharan, R., Trock, B. J., Lippman, M., Calvert, V. S., Petricoin, E. F., III, Liotta, L., Dadachova, E., Pestell, R. G., Lisanti, M. P., Bonaldo, P. & Scherer, P. E. Adipocyte-derived collagen VI affects early mammary tumor progression in vivo, demonstrating a critical interaction in the tumor/stroma microenvironment. *J. Clin. Invest.* 115, 1163-1176 (2005).
21. White, D. E., Kurpios, N. A., Zuo, D., Hassell, J. A., Blaess, S., Mueller, U. & Muller, W. J. Targeted disruption of beta1-integrin in a transgenic mouse model of human breast cancer reveals an essential role in mammary tumor induction. *Cancer Cell* 6, 159-70 (2004).
22. Paszek, M. J., Zahir, N., Johnson, K. R., Lakins, J. N., Rozenberg, G. I., Gefen, A., Reinhart-King, C. A., Margulies, S. S., Dembo, M., Boettiger, D., Hammer, D. A. & Weaver, V. M. Tensional homeostasis and the malignant phenotype. *Cancer Cell* 8, 241-54 (2005).
23. Wozniak, M. A., Desai, R., Solski, P. A., Der, C. J. & Keely, P. J. ROCK-generated contractility regulates breast epithelial cell differentiation in response to the physical properties of a three-dimensional collagen matrix. *J Cell Biol* 163, 583-95 (2003).
24. Liu, X., Wu, H., Byrne, M., Jeffrey, J., Krane, S. & Jaenisch, R. A targeted mutation at the known collagenase cleavage site in mouse type I collagen impairs tissue remodeling. *J Cell Biol* 130, 227-37 (1995).
25. Provenzano, P. P., Eliceiri, K. W., Campbell, J. M., Inman, D. R., White, J. G. & Keely, P. J. Collagen reorganization at the tumor-stromal interface facilitates local invasion. *BMC Medicine* 4:38, 2006.
26. Lin, E. Y., Jones, J. G., Li, P., Zhu, L., Whitney, K. D., Muller, W. J. & Pollard, J. W. Progression to malignancy in the polyoma middle T oncoprotein mouse breast cancer model provides a reliable model for human diseases. *Am J Pathol* 163, 2113-26 (2003).
27. Wang, W., Wyckoff, J. B., Frohlich, V. C., Oleynikov, Y., Huttelmaier, S., Zavadil, J., Cermak, L., Bottinger, E. P., Singer, R. H., White, J. G., Segall, J. E. & Condeelis, J. S. Single cell behavior in metastatic primary mammary tumors correlated with gene expression patterns revealed by molecular profiling. *Cancer Res* 62, 6278-88 (2002).
28. Zipfel, W. R., Williams, R. M., Christie, R., Nikitin, A. Y., Hyman, B. T. & Webb, W. W. Live tissue intrinsic emission microscopy using multiphoton-excited native fluorescence and second harmonic generation. *Proc Natl Acad Sci USA* 100, 7075-80 (2003).
29. Zoumi, A., Yeh, A. & Tromberg, B. J. Imaging cells and extracellular matrix in vivo by using second-harmonic generation and two-photon excited fluorescence. *Proc Natl Acad Sci USA* 99, 11014-9 (2002).
30. Brown, E., McKee, T., diTomaso, E., Pluen, A., Seed, B., Boucher, Y. & Jain, R. K. Dynamic imaging of collagen and its modulation in tumors in vivo using second-harmonic generation. *Nat Med* 9, 796-800 (2003).
31. Pradhan, A., Pal, P., Durocher, G., Villeneuve, L., Balassy, A., Babai, F., Gaboury, L. & Blanchard, L. Steady state and time-resolved fluorescence properties of metastatic and non-metastatic malignant cells from different species. *J Photochem Photobiol B* 31, 101-12 (1995).
32. Bavik, C., Coleman, I., Dean, J. P., Knudsen, B., Plymate, S. & Nelson, P. S. The gene expression program of prostate fibroblast senescence modulates neoplastic epithelial cell proliferation through paracrine mechanisms. *Cancer Res* 66, 794-802 (2006).
33. Allinen, M., Beroukhim, R., Cai, L., Brennan, C., Lahti-Domenici, J., Huang, H., Porter, D., Hu, M., Chin, L., Richardson, A., Schnitt, S., Sellers, W. R. & Polyak, K. Molecular characterization of the tumor microenvironment in breast cancer. *Cancer Cell* 6, 17-32 (2004).
34. Chung, L. W., Baseman, A., Assikis, V. & Zhau, H. E. Molecular insights into prostate cancer progression: the missing link of tumor microenvironment. *J Urol* 173, 10-20 (2005).
35. De Wever, O. & Mareel, M. Role of tissue stroma in cancer cell invasion. *J Pathol* 200, 429-47 (2003).
36. Condeelis, J., Singer, R. H. & Segall, J. E. THE GREAT ESCAPE: When Cancer Cells Hijack the Genes for Chemotaxis and Motility. *Annual Review of Cell and Developmental Biology* 21, 695-718 (2005).
37. Parr, C., Watkins, G., Mansel, R. E. & Jiang, W. G. The Hepatocyte Growth Factor Regulatory Factors in Human Breast Cancer. *Clin Cancer Res* 10, 202-211 (2004).
38. Sachdev, D. & Yee, D. The IGF system and breast cancer. *Endocr Relat Cancer* 8, 197-209 (2001).
39. Surmacz, E. Function of the IGF-I receptor in breast cancer. *J Mammary Gland Biol Neoplasia* 5, 95-105 (2000).
40. Byrne, C., Colditz, G. A., Willett, W. C., Speizer, F. E., Pollak, M. & Hankinson, S. E. Plasma insulin-like growth factor (IGF) I, IGF-binding protein 3, and mammographic density. *Cancer Res* 60, 3744-8 (2000).
41. Boyd, N. F., Stone, J., Martin, L. J., Jong, R., Fishell, E., Yaffe, M., Hammond, G. & Minkin, S. The association of breast mitogens with mammographic densities. *Br J Cancer* 87, 876-82 (2002).
42. Benlimame, N., He, Q., Jie, S., Xiao, D., Xu, Y. J., Loignon, M., Schlaepfer, D. D. & Alaoui-Jamali, M. A. FAK signaling is critical for ErbB-2/ErbB-3 receptor cooperation for oncogenic transformation and invasion. *J Cell Biol* 171, 505-16 (2005).
43. Aplin, A. E. & Juliano, R. L. Integrin and cytoskeletal regulation of growth factor signaling to the MAP kinase pathway. *J Cell Sci* 112 (Pt 5), 695-706 (1999).
44. Baron, V., Calleja, V., Ferrari, P., Alengrin, F. & Van Obberghen, E. p125Fak focal adhesion kinase is a substrate for the insulin and insulin-like growth factor-I tyrosine kinase receptors. *J Biol Chem* 273, 7162-8 (1998).
45. Ishizawar, R. & Parsons, S. J. c-Src and cooperating partners in human cancer. *Cancer Cell* 6, 209-14 (2004).
46. Hauck, C. R., Sieg, D. J., Hsia, D. A., Loftus, J. C., Gaarde, W. A., Monia, B. P. & Schlaepfer, D. D. Inhibition of focal adhesion kinase expression or activity disrupts epidermal growth factor-stimulated signaling promoting the migration of invasive human carcinoma cells. *Cancer Res* 61, 7079-90 (2001).

47. Sieg, D. J., Hauck, C. R., Ilic, D., Klingbeil, C. K., Schaefer, E., Damsky, C. H. & Schlaepfer, D. D. FAK integrates growth-factor and integrin signals to promote cell migration. *Nat Cell Biol* 2, 249-56 (2000).
48. Williams, R. M., Zipfel, W. R. & Webb, W. W. Interpreting second-harmonic generation images of collagen I fibrils. *Biophys J* 88, 1377-86 (2005).
49. Bird, D. K., Eliceiri, K. W., Fan, C. H. & White, J. G. Simultaneous two-photon spectral and lifetime fluorescence microscopy. *Appl Opt* 43, 5173-82 (2004).
50. Huang, S., Heikal, A. A. & Webb, W. W. Two-photon fluorescence spectroscopy and microscopy of NAD(P)H and flavoprotein. *Biophys J* 82, 2811-25 (2002).

EXAMPLE 6

Quantitative Analysis of Collagen Signatures to Determine Breast Cancer Progression in Clinical Samples The field of Biophotonics has greatly advanced over the last ten years, but has not been systematically applied to the study of breast cancer, particularly in a clinical context. The unrivaled ability of nonlinear optical methods (Multiphoton microscopy (MP), second harmonic generation (SHG)) to obtain deep high-resolution imaging can be exploited to better understand breast cancer progression. In this Example, we describe approaches for imaging tumor progression in mammary tissue combining nonlinear spectroscopic techniques and statistical analysis approaches.

Breast cancer biopsies and histopathology identification are still the gold standards for pathologists to identify and characterize carcinoma. Multiphoton microscopy and second harmonic generation imaging also provides useful tools for identifying and characterizing carcinoma. The present invention provides methods, for example, wherein, tumor-associated collagen signatures (TACS) observed in image date are identified and characterized so as to provide information relevant to the diagnosis and treatment of carcinoma. Importantly, these collagen signatures can be detected early in tumor development, and, therefore, can contribute to early diagnosis. These signatures also manifest in specific ways during tumor progression, and therefore, can be used to characterize the staging and prognosis of disease. Accordingly, TACS can be exploited to better image, diagnose, and stage carcinomas, particularly in the context of human tumor tissue. These optical methods are non-invasive and require no changes to current clinical techniques and yet can yield additional information that is useful in diagnosis. These methods also contribute quantitative information relevant to the histopathology process. The analysis of TACS is particularly important, as increased collagen density of breast tissue is one of the greatest risk factors for developing carcinoma (2).

This Example provides advanced techniques for histologic cancer imaging, in order to produce clinically useful information for diagnosis and staging of human breast carcinoma. Quantitative parameters of tumor-associated collagen signatures can be derived and characterized from images generated by multiphoton microscopy and second harmonic generation imaging methods. These quantitative parameters provide a means of enhancing the clinical applications of the present invention for diagnosing and treating breast cancer. For example, a "fingerprint" of collagen matrices can readily be determined and mapped spatially using multiphoton laser-scanning microscopy (MPLSM) and Second Harmonic Generation Imaging (SHG). Such quantitative parameters related to TACS can be extracted from these images by applying numerical values to intensity and fiber alignment in histologic samples from defined mouse mammary tumor progression models (MMTV-PyVT, -Wnt, and -neu models). The present methods are particularly useful for characterizing stromal changes in human breast carcinoma samples.

The present imaging approaches and analysis techniques are capable of improving the diagnostic information that is obtained from biopsy specimens, and, thus, may provide a means of enhancing the detection and or characterization of disease. Accordingly, the present multiphoton microscopy Second Harmonic Generation Imaging (SHG) methods and associated analysis techniques provide a valuable tool for clinical pathology.

In an embodiment, the present methods are useful for characterizing changes in collagen in breast cancer patients, and provide information that can be correlated to disease stage and outcome. This aspect of the present invention adds molecular information to the observation correlating mammographic density to carcinoma risk.

Mammographic density is linked to a four to six-fold increased risk of breast carcinoma (2). Importantly, increased breast density is associated with not only increased cellularity, but also with a significant increase in the deposition of extracellular matrix (ECM) components, especially collagen and fibronectin (4). Increased deposition of collagen and other extracellular matrix proteins surrounding tumors, termed desmoplasia, is associated with poor prognosis. Moreover, hormonal replacement therapy, in widespread use in the United States, increases breast density (7).

The molecular basis for the effects of dense breast tissue on development of breast carcinoma is not known. Increased collagen density, however, results in a three-fold increase in mammary tumor formation and invasion and metastasis in a dense collagen mouse model. Further, changes in local collagen density can promote adhesive signaling, and enhance cell proliferation and cell migration in vitro (10).

An increase in local collagen deposition is particularly relevant, as tumor cells migrate through and along collagen matrices (9). In particular, carcinoma migration in vivo occurs along tracks of collagen fibers (8) ((6)). Thus, changes in the local deposition of collagen surrounding tumors are likely to promote tumor cell invasion.

6.1 Tumor-Associated Collagen Signatures (TACS)

We have recently optimized the use of multiphoton microscopy to characterize consistent changes in the structure of collagen associated with mouse mammary carcinomas, termed Tumor-associated collagen signatures or TACS, which provide standard hallmarks to locate and characterize tumors: TACS-1) the presence of dense collagen, indicated by increased signal intensity at a region around the tumor as a standard hallmark for locating small tumor regions, TACS-2) the presence of taut (straightened) collagen fibers stretched around the tumor, indicating growth leading to increased tumor volume, TACS-3) the identification of radially aligned collagen fibers facilitating invasion, which may be indicative of the invasive and metastatic growth potential of a tumor. (see FIGS. 20 and 21).

Importantly, these collagen signatures can be detected early in tumor development and, therefore, identification and characterization of one or more tumor-associate collagen signatures can contribute to early diagnosis. Further, tumor-associate collagen signatures manifest in specific ways during tumor progression, and therefore, analysis of tumor-associate collagen signatures can contribute to determination of the staging and prognosis of disease. As such, these TACS provide indications that a tumor is, or could become, invasive and may serve as part of a strategy to help identify and characterize breast tumors in animal and human tissues.

6.2 Multiphoton Laser Scanning Microscopy (MPLSM) and Second Harmonic Generation (SHG)

Figure 19:
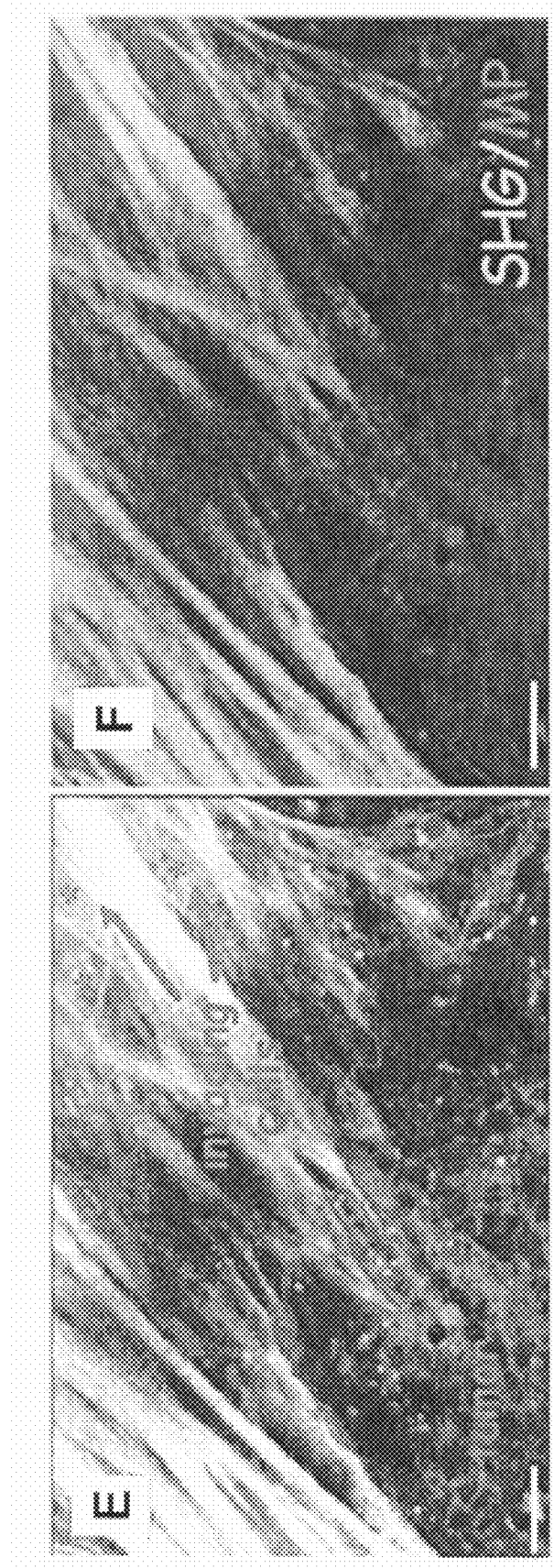

The extracellular matrix protein collagen has autofluorescent signal components at 325 nm and 400 nm, which have been attributed to the presence of intermolecular crosslinks between collagen fibrils. Interestingly, collagen fibers also exhibit a strong second harmonic generation signal, which can be exploited to study changes in collagen architecture with respect to cancer progression. SHG results from scattering due to the orientation, polarization and local symmetry found in chiral molecules such as collagen (3). Both multiphoton induced intensity image data and SHG data can be simultaneously detected on the same multiphoton system (FIG. 19).

Figure 21:
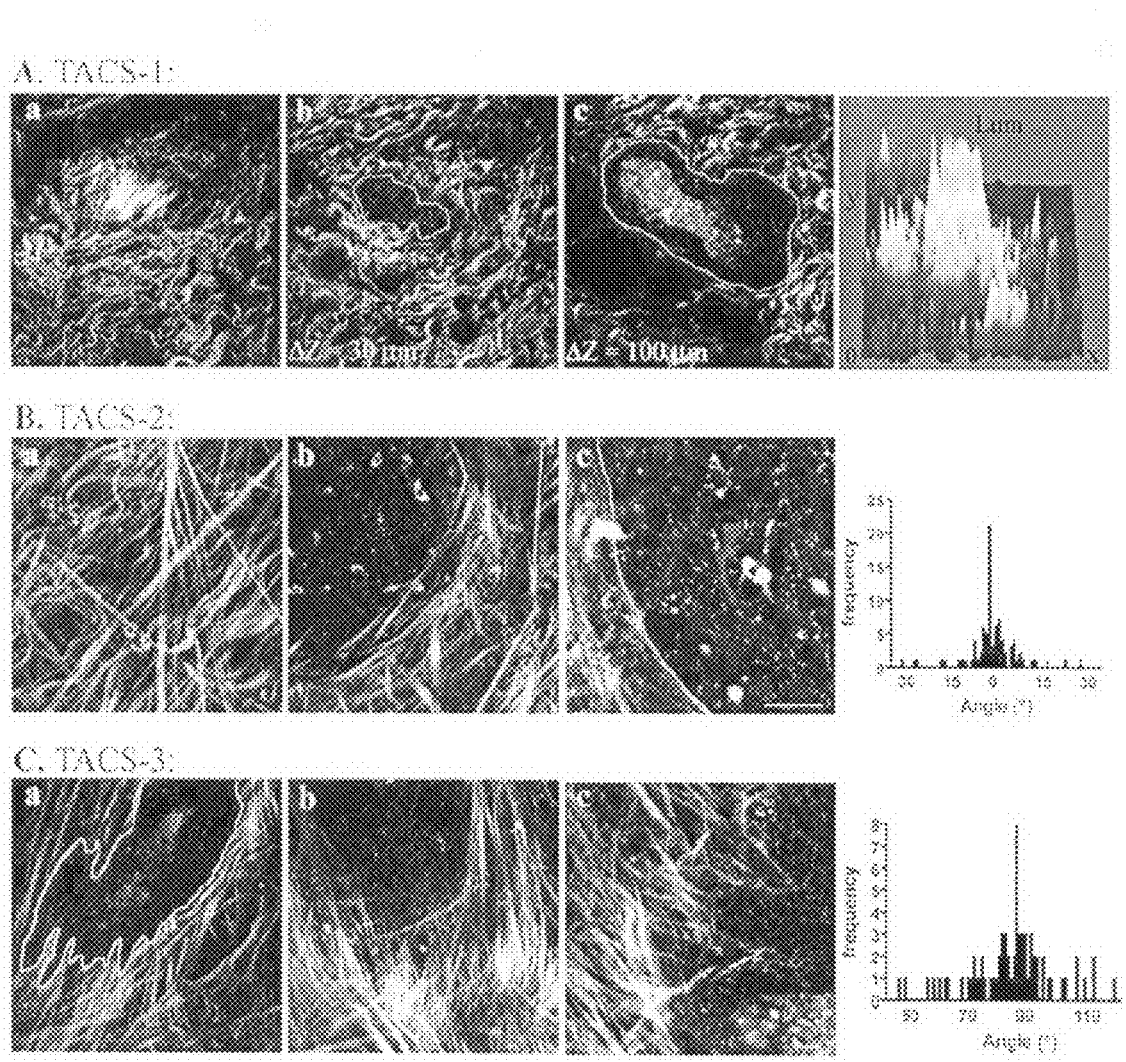
FIG. 21. The tumor-stromal interaction: representation of the three Tumor-Associated Collagen Signatures. (A. TACS-1) A region of dense collagen (a and surface map) "above" a non-palpable tumor (b-c; yellow outline) that is indicative of the presence of a small tumor. The surface map quantifies the intensity of the fluorescent signal relative to x-y location, and clearly demonstrates an increased collagen signal, and is representative of 14 analyzed mouse tumors. (B. TACS-2) MP/SHG images of collagen fibers stretched around a relatively smooth tumor boundary as demonstrated by the fact that majority of the fibers are parallel (at a 0° angle relative to the tumor boundary, as quantified in the B histogram). (C. TACS-3) The irregular tumor boundary associated with local invasion is outlined in a (a; yellow) and connected to fibers that are primarily distributed normal (90°) to the initial tumor boundary (C histogram).

6.3 Development of Quantitative Parameters of Tumor-Associated Collagen Signatures We have made a characterization of TACS in mouse mammary carcinoma models (6), and found that there is an initial deposition of collagen at a very early stage (=TACS1). In some methods of the present invention, a quantitative value is assigned to the intensity of collagen deposition corresponding to early stage carcinoma. This allows a threshold value for TACS1 to be quantified, wherein intensity values larger than this threshold correlate to cancerous or precancerous conditions, and optionally the staging and prognosis of disease. Moreover, the angle of collagen fibers relative to the tumor boundary is initially tangential (angle of 0°, =TACS2), and these fibers are realigned to be perpendicular to the tumor boundary (angle of 90°, =TACS3) upon progression to invasiveness (FIG. 21). In some embodiments, observed "angle of alignment" data corresponding to the angular orientation of the collagen fibers with respect to the tumor bundary is extracted from images to provide a quantitative numerical descriptor to the progression of mammary tumors. Accordingly, threshold intensities and angles of collagen fiber alignment are useful quantitative parameters in the present invention for identifying and characterizing carcinoma progression.

We have archived tumors from three different mouse models of mammary tumor progression: MMTV-PyVT, -Wnt, and -neu models. These models demonstrate spontaneous metastasis and local invasion, as well as desmoplasia. We have already demonstrated TACS progression in the PyVT and Wnt models (6). Because these tumors progress in predictable ways, TACS are valuable indicators for developing useful quantitative parameters for defined stages in carcinoma progression from early lesions to invasion and metastasis.

Figure 20:
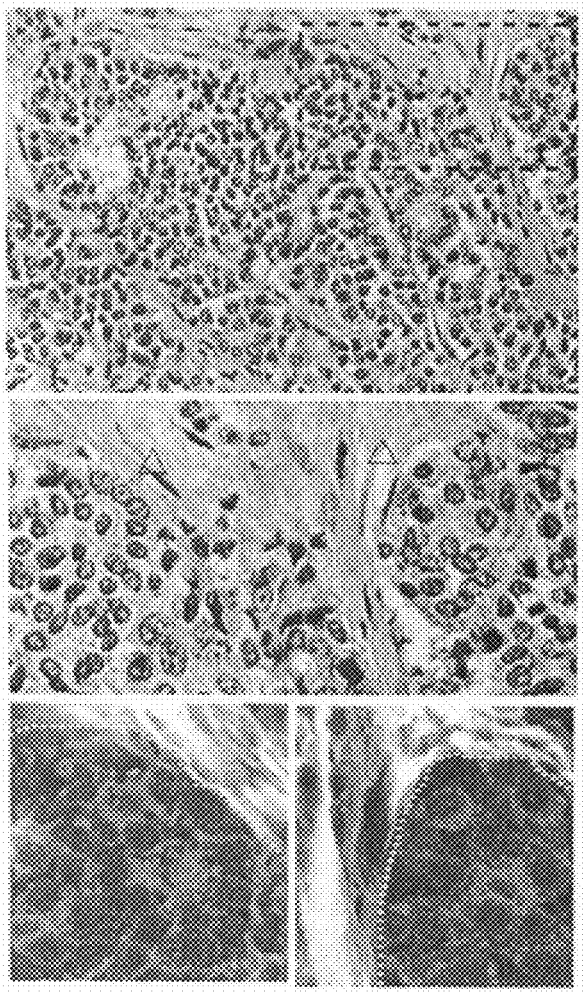
FIG. 20. MPLSM examination of TACS-2 and TACS-3 in H&E sections of MMTV-PyVT tumors. Left Column: Non-invading region of the tumor showing TACS-2 (see middle left panel arrows) that can be confirmed with MPLSM (bottom left). Right Column: Invading region of the tumor showing TACS-3 (see middle right panel arrows for examples of invading cells) that can be detected and confirmed with MPLSM (bottom right). Boxes in top row indicate region examined in the middle panels.
Figure 20:
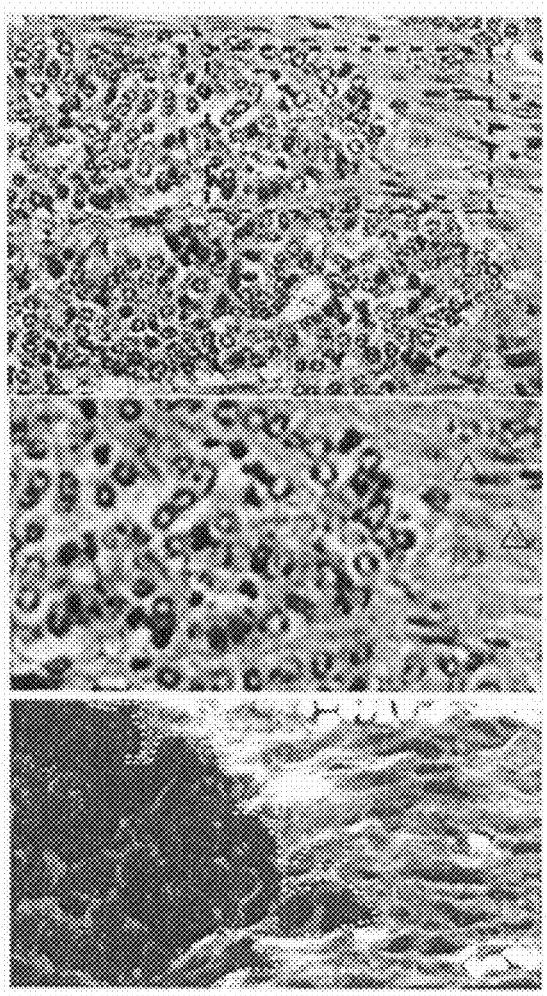

In an embodiment, quantitative parameters for identifying and characterizing TACS, are developed by cutting sections from each stage of tumor progression (e.g.: MMTV-PyVT weekly from 7-15 weeks). The sections are next stained with hematoxylin/eosin (H&E), in the manner of routine clinical pathology. At least 6 tumors for each time point are imaged by SHG and MPLSM. FIGS. 19, 20 & 21 shows exemplary collected images. Each tumor is independently assessed for tumor stage and TACS progression. For early tumors, a threshold level of intensity is determined that allows us to identify and characterize TACS1. For more progressed tumors, the collagen fiber angles relative to the tumor boundary is measured for each image. At least 20 fibers per tumor is measured, and a distribution for that tumor's population is determined. FIG. 21 provides exemplary distributions of the angle of collagen fibers relative to the tumor boundary. As shown in these plots, the distributions of the angle of collagen fibers relative to the tumor boundary are centered around 0 degrees and 90 degrees (corresponding to TACS3). A numerical value is determined from the image data for a tumor by averaging the angles observed, a numerical specification for the TACS that we will henceforth call the "TACS classifier." These numbers are graphed and compared to progression stage, such that a TACS classifier value is determined that reliably predicts the transition into invasion at the earliest stage. These quantitative TACS parameters provide guidance for applying numerical values to human samples, and making predictions useful for diagnostic and/or treatment applications.

6.4 Investigate Stromal Changes in Human Breast Carcinoma Samples

Although we have directly shown that there are significant and consistent changes in collagen structures during the progression of tumors in mouse mammary gland ((6)), the TACS of the present invention are also useful for diagnostic applications in human tissue, and are likely to be highly relevant for diagnosis or staging of human breast cancer. Given the result in mouse model systems, it is likely that the TACS analysis is also a useful predictor of tumor grade, matrix density, or clinical outcome for human subjects.

To demonstrate the applicability of the present methods for evaluation of human breast tissue, the following protocol can be carried out. Human breast tissue samples are imaged by both SHG and MPLSM, as shown in FIGS. 20 & 21. Imaging data relevant to identifying and characterizing TACS 1, 2, and 3, including intensity values for local collagen deposition, is collected. The angle of collagen fiber alignment relative to the tumor boundaries is determined for at least 20 fibers at random locations around the tumor boundary. Distribution graphs and "TACS Classifiers" are determined for each tumor, and compared to obtained values for mouse tumor progression. The "TACS Classifier data is compared with the known clinical diagnosis and outcome for each patient.

6.5 Statistical Analysis

In some embodiments, statistical analysis techniques are used in the present invention to ensure that numerical values derived from imaging data for tumor associate signatures (TACS1, TACS2 and/or TACS3) are statistically significant. TACS classifier values are first characterized using standard descriptive statistics in terms of means, standard deviations, medians and ranges. In some embodiments, intraclass correlation coefficients (ICCs) are computed to evaluate the inter-rater reliability of the TACS measurements. In some embodiments, TACS classifier values are correlated with clinical outcomes (disease-free survival, overall survival, time to recurrence), diagnosis, disease stage, and hormone receptor status of 207 breast cancer carcinoma cases, as described in (1, 5). Analysis of variance (ANOVA) with subject specific random effects can also be performed so as to compare TACS values between disease stages and hormone receptor status (ER+, ER−). The associations between TACS values and expression levels of molecular markers, including Ki67, syndecan 1, and syndecan 4, Her2/neu, can also be examined in the methods of the present invention using linear or non-linear regression analyses. In some embodiments, Univariate Cox regression analyses is performed to evaluate the associations between TACS and disease-free survival, overall survival and time to recurrence. Furthermore, in order to determine if the change in TACS is an independent prognostic marker of disease-free survival, overall survival or time to recurrence, we can fit multivariate Cox proportional hazards models with additional covariates, including (but not limited to) the following: size of primary tumor, stage, patient age at diagnosis, estrogen and progesterone expression, Her2/neu levels, and nodal status. Predictive markers are selected in some methods via backward or forward stepwise selection with a p-value cutoff of <0.05. Additional analyses may also be performed, such as sub-group analyses for each histologic subtype.

A sample size of 207 breast cases is sufficient to detect moderate effect sizes (less than ½ standard deviation units) in TACS classifier values between various subsets of patients (e.g., grade, receptor status, etc) with adequate power. For example, assuming 28% (n=58) of the patients had a grade 1 tumor while 40% (n=83) had a grade 3 tumor. In our data (6), the overall standard deviation of TACS-2 and TACS-3 fiber angle values relative to the tumor boundary is 15°. Assuming a sample size of 58 cases with grade 1 tumor, 83 cases with grade 3 tumor, and an overall standard deviation of 15°, a mean differences of 45° or more in fiber angel values relative to tumor boundary can be detected with >95% power at a two-sided significance level of 5%.

6.6 Clinical Outcomes

An advantage of the present methods, is that they provide quantitative parameters (threshold collagen intensities, collagen fiber angles of alignment and distributions thereof, TACS classifiers, TACS values for collagen, etc.) that are intended to supplement the convention qualitative assessment of excised breast tissue via convention methods (e.g., a pathologist "reading" an H&E slide). Therefore the present invention provides additional quantitative diagnostic parameters that facilitate pathologists stage disease and determine prognosis.

6.7 REFERENCES

1. Baba, F., K. Swartz, R. van Buren, J. Eickhoff, Y. Zhang, W. Wolberg, and A. Friedl. 2006. Syndecan-1 and syndecan-4 are overexpressed in an estrogen receptor-negative, highly proliferative breast carcinoma subtype. Breast Cancer Res Treat 98:91-8.
2. Boyd, N. F., L. J. Martin, J. Stone, C. Greenberg, S. Minkin, and M. J. Yaffe. 2001. Mammographic densities as a marker of human breast cancer risk and their use in chemoprevention. Curr Oncol Rep 3:314-21.
3. Campagnola, P. J., H. A. Clark, W. A. Mohler, A. Lewis, and L. M. Loew. 2001. Secondharmonic imaging microscopy of living cells. J Biomed Opt 6:277-86.
4. Guo, Y. P., L. J. Martin, W. Hanna, D. Banerjee, N. Miller, E. Fishell, R. Khokha, and N. F. Boyd. 2001. Growth factors and stromal matrix proteins associated with mammographic densities. Cancer Epidemiol Biomarkers Prev 10:243-8.
5. McNeel, D. G., J. Eickhoff, F. T. Lee, D. M. King, D. Alberti, J. P. Thomas, A. Friedl, J. Kolesar, R. Marnocha, J. Volkman, J. Zhang, L. Hammershaimb, J. A. Zwiebel, and G. Wilding. 2005. Phase I trial of a monoclonal antibody specific for alphavbeta3 integrin (MEDI-522) in patients with advanced malignancies, including an assessment of effect on tumor perfusion. Clin Cancer Res 11:7851-60.
6. Provenzano, P. P., K. W. Eliceiri, J. M. Campbell, D. R. Inman, J. G. White, and P. J. Keely. 2006. Collagen reorganization at the tumor-stromal interface facilitates local invasion. BMC Med 4:38.
7. Rutter, C. M., M. T. Mandelson, M. B. Laya, D. J. Seger, and S. Taplin. 2001. Changes in breast density associated with initiation, discontinuation, and continuing use of hormone replacement therapy. Jama 285:171-6.
8. Sahai, E., J. Wyckoff, U. Philippar, J. Segall, F. Gertler, and J. Condeelis. 2005. Simultaneous imaging of GFP, CFP and collagen in tumors in vivo using multiphoton microscopy. BMC Biotechnology 5:14.
9. Wolf, K., I. Mazo, H. Leung, K. Engelke, U. H. von Andrian, E. I. Deryugina, A. Y. Strongin, E. B. Brocker, and P. Friedl. 2003. Compensation mechanism in tumor cell migration: mesenchymal-amoeboid transition after blocking of pericellular proteolysis. J. Cell Biol. 160:267-277.
10. Wozniak, M. A., R. Desai, P. A. Solski, C. J. Der, and P. J. Keely. 2003. ROCK-generated contractility regulates breast epithelial cell differentiation in response to the physical properties of a three-dimensional collagen matrix. J Cell Biol 163:583-95.

EXAMPLE 7

Novel Signal Processing Strategies for Identification of Tumor-associated Collagen Signatures Multiphoton laser-scanning microscopy methodologies such as multiphoton-excitation (MPE) and second-harmonic generation (SHG) are useful for imaging of live intact tumor samples. As described above, using these techniques we have characterized three Tumor-associated collagen signatures (TACS) that classify consistent changes in the structure of collagen associated with tumor formation and progression. Importantly, these collagen signatures indicate early tumor development and specific structures associated with tumor progression and local invasion, a precursor to metastasis, demonstrating that analysis of TACS can contribute to the staging and prognosis of disease.

Quantitative and statistical tools are used in some methods of the present invention to accurately identify and characterize TACS in image data so as to facilitate implementation of the present methods for a range of experimental and clinical applications. Advanced signal processing techniques are useful in these methods for providing automated classification and quantification of TACS for experimental and clinical use. Curvelet analysis, for example, allows the representation of objects in a sparse manner while retaining orientation information, and is therefore particularly useful in the present methods for quantifying changes in matrix organization associated with TACS. In the present invention, curvelet analysis is performed on TACS image data from relevant live tumor samples and histology sections.

To facilitate quantitative and statistical analysis in the present methods, it is useful to represent relevant quantitative TACS signal data using visualization and analysis software tools. In order to implement relevant signal data into a robust computational interface, some methods of the present invention utilize Visbio, a computational toolkit for visualizing and analyzing microscopy data. This software toolkit is useful to output location, scale, and orientation data with maps and colorized the overlays relative to the tumor boundary to identify and quantify TACS.

A fundamental desire in the diagnosis of human cancers is the ability to accurately determine changes in tissue that accompany carcinoma progression, and to be able to monitor and use these changes to make predictions about the stage and outcome of the disease. It is clearly established that tumor progression is associated with changes in the structure and deposition of connective tissue components, especially collagen. However, these changes have not to date been exploited for the diagnosis of carcinomas. As discussed throughout this description, multiphoton and second harmonic generation microscopy is a useful tool for characterizing consistent changes in the structure of collagen associated with mouse mammary carcinomas, termed Tumor-associated collagen signatures (TACS). Importantly, these collagen signatures are an intrinsic signal associated with carcinoma progression, and can be detected in fresh, unstained tissue using multiphoton microscopy. Moreover, these signatures can be detected early in tumor development, enabling their use in early diagnosis, and characterization of the staging and prognosis of disease.

An advantage of some embodiments of the present methods is that they provide an automated and quantitative way to describe and quantify TACS. This aspect of the present invention provides diagnostic information about the stage and progression of carcinomas. Analysis of TACS image data in these embodiments can be accomplished by: (i) implementing relevant signal processing techniques to automate classification and quantification of TACS for experimental and diagnostic use; and (ii) representing relevant quantitative TACS signal data with visualization and analysis software tools The present TACS analysis and visualization techniques have important research and clinical applications. First, the use of TACS analysis combined with compact multiphoton microscope systems in clinical pathology labs allows rapid detection of tumors in fresh tissue samples even as a patient is still in the operating room during excisional biopsy or surgical resection, and aids the surgeon in determining whether tumor margins have been obtained and whether additional resection is necessary. Second, TACS analysis can be used on classic histology samples to help stage and diagnose disease. Third, TACS analysis aids researchers who require quantitative endpoints for in vivo tumorigenesis studies in animal models. Finally, TACS analysis can be exploited for intravital imaging to augment the assessment of tumor progression and local analysis.

To date it has been commonly proposed that in order for nonlinear optical imaging to have widespread utility in medical imaging, it would be necessary to utilize fiber optics to conduct multiphoton imaging through endoscopy[1-5]. Although this research still carries great promise, and the work shown herein will certainly be of great use to signals obtained with such instruments, a use for multiphoton imaging in clinical pathology in fact currently exists, but has not yet flourished largely because of a lack of informatics tools. Since multiphoton microscopy allows imaging of live freshly harvested tissue, an initial pathological assessment can be made quite rapidly using the appropriate computational tools.

Multidimensional Nonlinear Imaging: Nonlinear optical imaging techniques such as multiphoton laser scanning microscopy (MPLSM) and second harmonic generation (SHG), provide powerful tools to image cellular processes both in vitro and in vivo[6-15]. As such, they provide great potential for obtaining additional information from standard pathology sections as well as rapid pathological evaluation of freshly harvested biopsy tissue before traditional processing.

Multiphoton Excitation is an optical sectioning technique where fluorescence excitation is restricted to the plane of focus, with an effective imaging depth that can greatly exceed conventional confocal microscopy[11,16], while maintaining viability[17]. Second Harmonic Generation, in contrast to the fluorescent emission resulting from multiphoton excitation, second harmonic generation arises from the laser field suffering a nonlinear, secondorder, polarization when passing through non-centrosymmetric ordered structures[8,13,20-24], such as fibrillar collagen. Since multiphoton excitation and second harmonic generation can be executed simultaneously, yet still be differentiated due to their distinct emission signals, it provides a powerful tool for imaging heterogeneous biological tissues.

Tumor-Associated Collagen Signatures (TACS): Intrinsic fluorescence detection with multiphoton excitation in combination with SHG facilitates three-dimensional, high resolution, imaging in non-fixed, non-sectioned, non-stained mammary tissues and tumors. This imaging provides information commonly obtained with classical histology without the need for complex and destructive sample preparation, allowing rapid pathological assessment with additional structural information in multiple dimensions. Furthermore, we have performed three dimensional imaging of tumors in situ and characterized three "Tumor-Associated Collagen Signatures", which provide standard hallmarks to locate and characterize tumors (FIG. 21).

TACS-1: The presence of locally dense collagen within the globally increased collagen concentration surrounding tumors, indicated by increased signal intensity at a region around the tumor and can be used as a standard hallmark for locating small (non-palpable) tumor regions.

TACS-2: The occurrence of taut (transitioned from wavy to straightened) collagen fibers stretched around a palpable tumor, indicating substantial tumor volume resulting from tumor growth.

TACS-3: The presence of radially aligned collagen fibers facilitating local invasion, which are indicative of the invasive and metastatic growth potential of a tumor, and correlate to histology. TACS-3 indicates an invasive phenotype and quantitative analysis of these TACS can help aid in pathological assessment.

The Curvelet Transform

Current work in Computational Harmonic Analysis focuses on developing multiscale data representation techniques to represent objects in a sparse manner while retaining orientation information. The sparser the representation, the fewer the number of coefficients that are needed to be transmitted (allowing for the use of various compression schemes), and the better the denoising that will result from coefficient shrinkage[26]. While Fourier analysis works well on periodic structures (such as textures), and wavelet analysis works well on singularities (such as corners), neither particularly can reconstruct edges in a sparse matter. Curvelets were originally introduced by Candes and Donoho[27] as a non-adaptive transform that achieves near optimal mterm approximation rates in $L^2$ for twice-continuously differentiable curves $C^2$.

Figure 22:
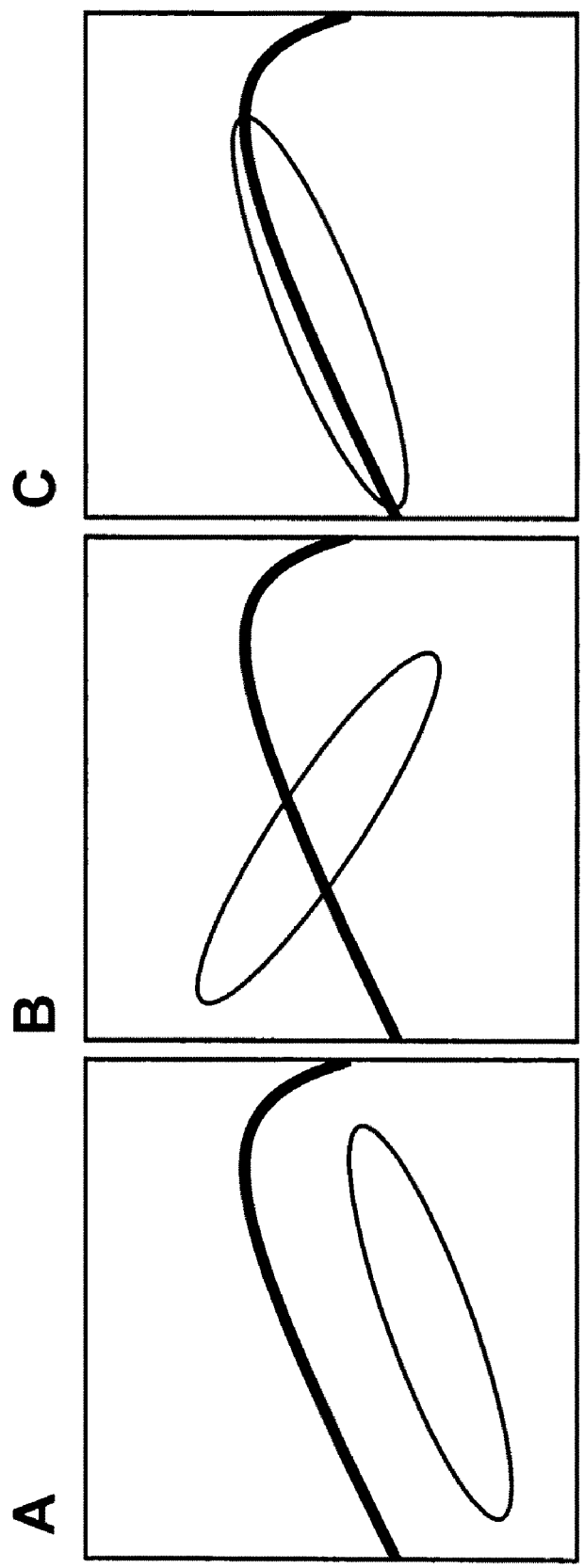
FIG. 22. (A) Category 1: A curvelet whose length-wise support does not intersect a discontinuity. The curvelet coefficient magnitude will be zero. (B) Category 2: A curvelet whose length-wise support intersects with a discontinuity, but not at its critical angle. The curvelet coefficient magnitude will be very close to zero. (C) Category 3: A curvelet whose length-wise support intersects with a discontinuity, and is tangent to that discontinuity. The curvelet coefficient magnitude will be much larger than zero.

Curvelet coefficients represent the inner product of a tight frame with the given image. These tight frames are adjusted for scale (where the frame length grows at twice the frame width), orientation (rotating the frame), and location (moving the frame in a grid structure around the image). The power of this scaling technique is that at fine scales, the curvelet frame acts like a needle that can accurately detect long straight edges. In Candes and Donoho[28], a visual argument is made that all curvelet coefficients fall into one of three categories (FIG. 22).

Sparsity can be seen in FIG. 22A through 22C (the bold line representing the $C^2$ curve, the fine line representing the support of the Curvelet frame). When performing the curvelet transform on a $C^2$ curve, only curvelet coefficients matching the orientation and location of edges will be above negligible magnitude values. In Candes and Donoho[28], it is declared that Curvelets over optimal sparseness for "curve punctuated smooth" images, where the image is smooth with the exception of discontinuities along $C^2$ curves. Sparseness is measured by the rate of decay of the m-term approximation (reconstruction of the image using m number of coefficients) of the algorithm. Having a sparse representation, along with offering improved compression possibilities, also allows for improving denoising performance[26] as additional sparseness increases the amount of smooth areas in the image.

Another advantage of the Curvelet Algorithm, directly applicable to the problem of detecting Tumor-Associated Collagen Signatures, is the ability of the transform to retain orientation information from the image. As seen in FIGS. 22A-C, the Curvelet Transform not only varies on scale and location in the image, but also the orientation of the edges (notice the difference in the curvelet frame between FIGS. 22B and 22C). This results in the ability to examine all prominent edges at a particular orientation and a particular scale (varying only on location of the fixed scale and orientation curvelet in the image). When applied to the identification and characterization of Tumor-Associated Collagen Signatures in imaging data, the curvelet transform becomes a powerful tool for detecting the presence of long straight edges and their location, scale, and orientation (e.g., angular orientation). By obtaining accurate quantitative data regarding collagen amount, morphology, and organization/orientation, biologically relevant data will acquired that will be implemented into an intuitive software interface for rapid and accurate tumor analysis in research and clinical settings.

Visualization and analysis software tools (VisBio)

In order to be readily interpretable by biologists or pathologists, it is useful to represent the curvelet analysis in a visual manner. In some embodiments, the present invention provides a computational infrastructure for visualizing, analyzing, and archiving data[29,30], including an advanced multidimensional image viewer with advanced analysis tools, such as spectral-lifetime analysis that utilizes a database system based on the Open Microscopy Environment database system. VisBio's data engine has been designed so that it is capable of supporting data of n-dimensions (such as time, space, spectra, and lifetime). The present signal analysis based approaches can be incorporated into VisBio by the development of a "plug-in" architecture with a versatile application program interface. The plug-in architecture will facilitate the development of new functionalities as algorithms can be developed and tested on model data in programs that run outside of the VisBio environment. VisBio currently has a preliminary implementation of such an architecture, which meets many of the needs of the signal analysis algorithms applied to TACS and related problems.

In an embodiment, signaling processing code is interfaced with the VisBio toolkit so as to implement relevant signal data into a robust computational interface. The curvelet algorithm is implemented as an external native (C++) program and is interfaced with VisBio through its plug-in architecture. VisBio will be able to make use of the resultant coefficients to assist the investigator in a number of ways. The largest coefficients naturally correspond to the longest, most prominent edges; such coefficients can be transformed back into the time domain and overlaid on the original data to highlight collagen structures. The orientation data can be used to colorize the overlays; further, coupled with a user-drawn tumor boundary, the orientation of the structures relative to the tumor can be illustrated, making it easy to quickly diagnosis the tumor's status at a glance.

REFERENCES

1. Bird, D. & Gu, M. Fibre-optic two-photon scanning fluorescence microscopy. *J Microsc* 208, 35-48 (2002).
2. Bird, D. & Gu, M. Resolution improvement in two-photon fluorescence microscopy with a single-mode fiber. *Appl Opt* 41, 1852-7 (2002).
3. Bird, D. & Gu, M. Two-photon fluorescence endoscopy with a micro-optic scanning head. *Opt Lett* 28, 1552-4 (2003).
4. Flusberg, B. A., Cocker, E. D., Piyawattanametha, W., Jung, J. C., Cheung, E. L. & Schnitzer, M. J. Fiber-optic fluorescence imaging. *Nat Methods* 2, 941-50 (2005).
5. Jung, J. C. & Schnitzer, M. J. Multiphoton endoscopy. *Opt Lett* 28, 902-4 (2003).
6. Provenzano, P. P., Eliceiri, K. W., Yan, L., Ada-Nguema, A., Conklin, M. W., Inman, D. R. & Keely, P. J. Nonlinear optical imaging of cellular processes in breast cancer. *Microscopy and Microanalysis* (accepted).
7. Zipfel, W. R., Williams, R. M., Christie, R., Nikitin, A. Y., Hyman, B. T. & Webb, W. W. Live tissue intrinsic emission microscopy using multiphoton-excited native fluorescence and second harmonic generation. *Proc Natl Acad Sci USA* 100, 7075-80 (2003).
8. Cox, G., Kable, E., Jones, A., Fraser, I., Manconi, F. & Gorrell, M. D. 3-dimensional imaging of collagen using second harmonic generation. *J Struct Biol* 141, 53-62 (2003).
9. Zoumi, A., Yeh, A. & Tromberg, B. J. Imaging cells and extracellular matrix in vivo by using second-harmonic generation and two-photon excited fluorescence. *Proc Natl Acad Sci USA* 99, 11014-9 (2002).
10. Brown, E., McKee, T., diTomaso, E., Pluen, A., Seed, B., Boucher, Y. & Jain, R. K. Dynamic imaging of collagen and its modulation in tumors in vivo using secondharmonic generation. *Nat Med* 9, 796-800 (2003).
11. Denk, W., Strickler, J. H. & Webb, W. W. Two-photon laser scanning fluorescence microscopy. *Science* 248, 73-6 (1990).
12. Wang, W., Goswami, S., Sahai, E., Wyckoff, J. B., Segall, J. E. & Condeelis, J. S. Tumor cells caught in the act of invading: their strategy for enhanced cell motility. *Trends Cell Biol* 15, 138-45 (2005).
13. Campagnola, P. J., Millard, A. C., Terasaki, M., Hoppe, P. E., Malone, C. J. & Mohler, W. A. Three-dimensional high-resolution second-harmonic generation imaging of endogenous structural proteins in biological tissues. *Biophys J* 82, 493-508 (2002).
14. Brown, E. B., Campbell, R. B., Tsuzuki, Y., Xu, L., Carmeliet, P., Fukumura, D. & Jain, R. K. In vivo measurement of gene expression, angiogenesis and physiological function in tumors using multiphoton laser scanning microscopy. *Nat Med* 7, 864-8 (2001).
15. Eliceiri, K. W., Fan, C. H., Lyons, G. E. & White, J. G. Analysis of histology specimens using lifetime multiphoton microscopy. *J Biomed Opt* 8, 376-80 (2003).
16. Centonze, V. E. & White, J. G. Multiphoton excitation provides optical sections from deeper within scattering specimens than confocal imaging. *Biophys J* 75, 2015-24 (1998).
17. Squirrell, J. M., Wokosin, D. L., White, J. G. & Bavister, B. D. Long-term two-photon fluorescence imaging of mammalian embryos without compromising viability. *Nat Biotechnol* 17, 763-7 (1999).
18. Helmchen, F. & Denk, W. New developments in multiphoton microscopy. *Curr Opin Neurobiol* 12, 593-601 (2002).
19. Diaspro, A. & Sheppard, C. J. R. Two-Photon Excitation Fluorescence Microscopy. In *Confocal and Two-Photon Microscopy: Foundations, Applications, and Advances* (ed. Diaspro, A.) 39-73 (Wiley-Liss, Inc., New York, 2002).
20. Williams, R. M., Zipfel, W. R. & Webb, W. W. Interpreting second-harmonic generation images of collagen I fibrils. *Biophys J* 88, 1377-86 (2005).
21. Mohler, W., Millard, A. C. & Campagnola, P. J. Second harmonic generation imaging of endogenous structural proteins. *Methods* 29, 97-109 (2003).

22. Stoller, P., Kim, B. M., Rubenchik, A. M., Reiser, K. M. & Da Silva, L. B. Polarization dependent optical second-harmonic imaging of a rat-tail tendon. *J Biomed Opt* 7, 205-14 (2002).
23. Freund, I. & Deutsch, M. Second-harmonic microscopy of biological tissue. *Optics Letters* 11, 94-96 (1986).
24. Plotnikov, S. V., Millard, A. C., Campagnola, P. J. & Mohler, W. A. Characterization of the myosin-based source for second-harmonic generation from muscle sarcomeres. *Biophys J* 90, 693-703 (2006).
25. Shen, y. r. Surface properties probed by second-harmonic and sum-frequency generation. *Nature* 337, 519-525 (1989).
26. Donoho, D. L. De-noising by soft-thresholding. *IEEE Transactions on Information Theory* (1995).
27. Candes, E. J. & Donoho, D. L. Curvelets—A surprisingly effective non-adaptive representation for objects with edges. in *Curve and Surface Fitting* (Vanderbilt Univ. Press, 1999).
28. Candes, E. J. & Donoho, D. L. New Tight Frames of Curvelets and Optimal Representations of Objects with Smooth Singularities. (Technical Report, Stanford University, 2002).
29. Rueden, C., Eliceiri, K. W. & White, J. G. VisBio: a computational tool for visualization of multidimensional biological image data. *Traffic* 5, 411-7 (2004).
30. Eliceiri, K. W. & Rueden, C. Tools for visualizing multi-dimensional images from living specimens. *Photochem Photobiol* 81, 1116-22 (2005).
31. Provenzano, P. P., Eliceiri, K. W., Campbell, J. M., Inman, D. R., White, J. G. & Keely, P. J. Collagen reorganization at the tumor-stromal interface facilitates local invasion. (in review).

EXAMPLE 8

Tumor-Associated Collagen Signatures in Human Tissue Samples

To evaluate the applicability of the present methods for the diagnosis and treatment of cancer in human subjects, human tissue samples were imaged using a combination of second harmonic generation and multiphoton fluorescence techniques. The acquired images were analyzed to identify and characterize tumor-associated collagen signatures in the image data. The results of this Example demonstrate that the methods of the present invention are useful for identifying and characterizing cancer in human tissue samples.

Figure 23:
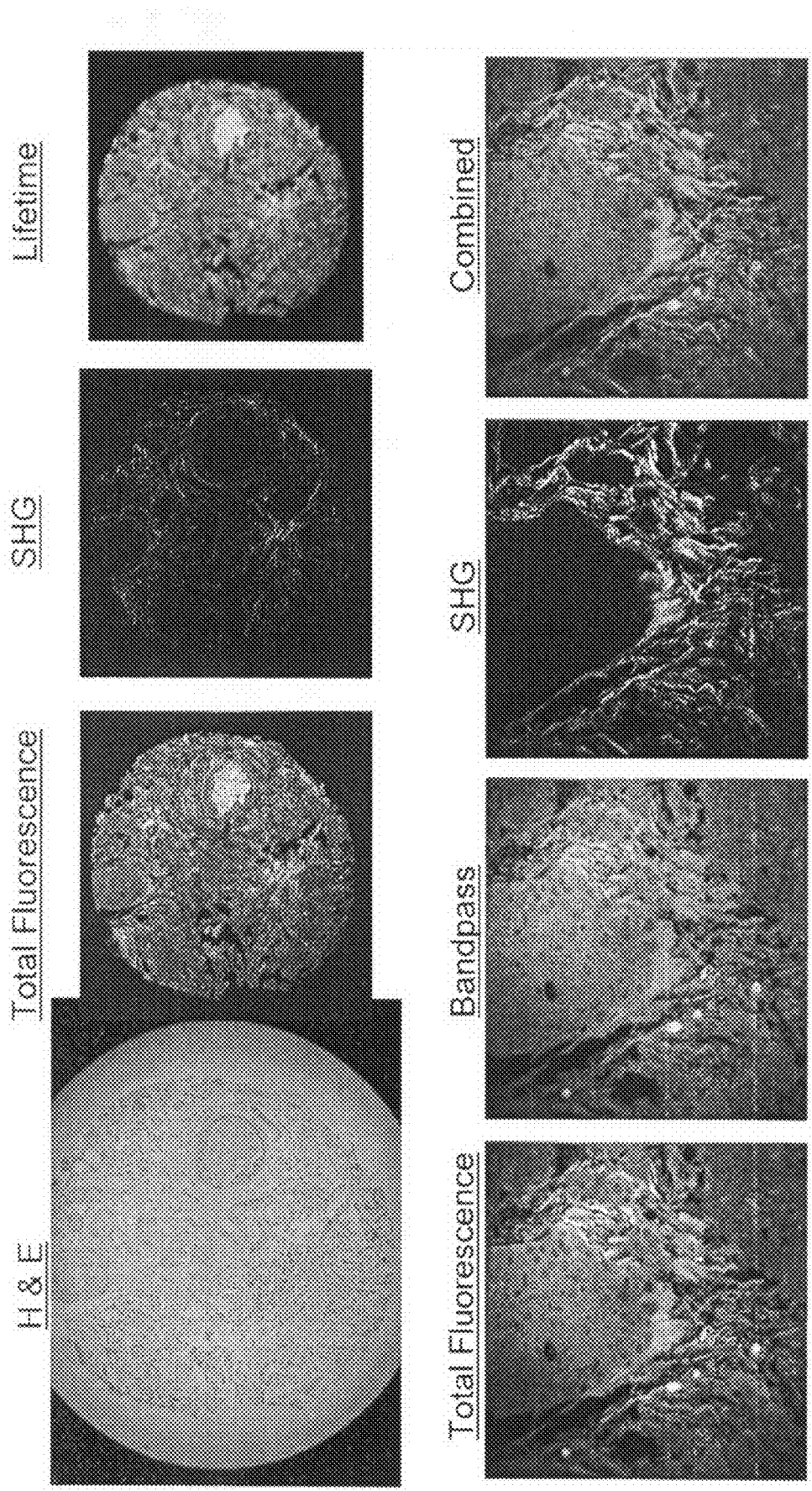
FIG. 23 provides images for human histopathology samples generated using a combination of second harmonic generation imaging techniques and multiphoton fluorescence imaging techniques.

FIG. 23 provides images for human histopathology samples generated using a combination of second harmonic generation imaging techniques and multiphoton fluorescence imaging techniques. Also shown in FIG. 23 is a fluorescence lifetime spectrum for the sample.

All images were acquired from a biopsy of human breast tumor tissue which was formalin fixed, embedded, cut and stained with hematoxylin and eosin (H&E) according to standard histology techniques. A single tissue slice was imaged in different ways to illustrate how various techniques can yield alternative information. The upper row of images were acquired using a 10× objective lens, starting on the left we see a brightfield image taken with a digital camera which shows the classic blue and pink coloration of the tissue (Note: this Brightfield image of H&E, is what a pathologist traditionally reads to make a diagnosis). Next a fluorescence image is shown acquired using multiphoton excitation at 890 nm without any emission filtering where a large extent of the tissue fluoresces due to staining by eosin. The next image is the Second Harmonic (SHG) signal acquired from the sample imaged using 890 nm excitation and a narrow 445 nm bandpass filter to select for the SHG. The underlying filamentous structure of collagen was observed using this technique even at this low magnification. The lifetime of fluorescence was also measured, where the decay of fluorescence for each pixel was fit with two exponential functions. The longer of the functions ($\tau_2$) was pseudocolor mapped to the image where colder color represent shorter lifetimes (<2000 ps) and warmer colors longer lifetimes (>2300 ps) where, in general, collagen has a shorter fluorescence lifetime (blue color map). The lower row of images were all acquired using a 40× 1.3 N.A. objective lens in order to more closely examine the region at the top of the tissue slice where a TACS-3 result was observed. TACS-3 presence was determined by the perpendicular orientation of a dense concentration of collagen in relation to the large group of cells. The total fluorescence image of a group of cells surrounded by stroma showed that the fluorescence intensity is variable. By using a bandpass emission filter (480:550), only a small portion of the emitted fluorescence is attenuated. Conversely, when the tissue was imaged for SHG signal only, a clear separation of the TACS-3 collagen structure from the rest of the stroma and cells was achieved. An overlay of the SHG and fluorescence bandpass images highlights this distinction. In this combined image collagen fibers appear red in proximity to tumor sample, demonstrating our ability to separate and image these signals. Note that there is both TACS 3 (straight, perpendicular fibers) and TACS 2 (parallel fibers) in proximity to this tumor.

STATEMENTS REGARDING INCORPORATION BY REFERENCE AND VARIATIONS

The follow in references relate generally to biomedical imaging via nonlinear optical imaging methods and are incorporated by reference in their entireties herein: (1) Brown, et al., 2003, "Dynamic imaging of collagen and its modulation in tumors in vivo using second-harmonic generation," Nature Medicine, 9:6, 796-800; (2) Campagnola, et al., 2002, "Three-dimensional high-resolution second-harmonic generation imaging of endogenous structural proteins in biological tissues," Biophysical Journal, 81, 493-508; (3) Wang, et al., 2002, "Single cell behavior in metastatic primary mammary tumors correlated with gene expression patterns revealed by molecular profiling," Cancer Research, 62, 6278-6288; (4) Zipfel, et al., 2002, "Nonlinear magic: multiphoton microscopy in the biosciences," Nature Biotechnology, 21:11, 1369-1377; (5) Zipfel, et al., 2003, "Live tissue intrinsic emission microscopy using multiphoton-excited native fluorescence and second harmonic generation," PNAS, 100: 12, 7075-7080; and (6) Zoumi, et al., 2002, "Imaging cells and extracellular matrix in vivo by using second-harmonic generation and two-photon excited fluorescence," PNAS, 99:17, 11014-11019.

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. Barcellos-Hoff, M. H., Aggeler, J., Ram, T. G. & Bissell, M. J. (1989) *Development* 105, 223-35.
2. Keely, P., Fong, A., Zutter, M. & Santoro, S. (1995) *J Cell Science* 108, 595-607.
3. Keely, P. J., Wu, J. E. & Santoro, S. A. (1995) *Differentiation* 59, 1-13.
4. Chen, J., Diacovo, T. G., Grenache, D. G., Santoro, S. A. & Zutter, M. M. (2002) *Am J Pathol* 161, 337-44.
5. Ronnov-Jessen, L., Petersen, O. W., Koteliansky, V. E. & Bissell, M. J. (1995) *J Clin Invest* 95, 859-73.
6. Tlsty, T. D. & Hein, P. W. (2001) *Curr Opin Genet Dev* 11, 54-9.
7. Elenbaas, B., Spirio, L., Koerner, F., Fleming, M. D., Zimonjic, D. B., Donaher, J. L., Popescu, N. C., Hahn, W. C. & Weinberg, R. A. (2001) *Genes Dev* 15, 50-65.
8. Wang, W., Wyckoff, J. B., Frohlich, V. C., Oleynikov, Y., Huttelmaier, S., Zavadil, J., Cermak, L., Bottinger, E. P., Singer, R. H., White, J. G., Segall, J. E. & Condeelis, J. S. (2002) *Cancer Res* 62, 6278-88.
9. Boyd, N. F., Martin, L. J., Stone, J., Greenberg, C., Minkin, S. & Yaffe, M. J. (2001) *Curr Oncol Rep* 3, 314-21.
10. Boyd, N. F., Lockwood, G. A., Byng, J. W., Tritchler, D. L. & Yaffe, M. J. (1998) *Cancer Epidemiol Biomarkers Prev* 7, 1133-44.
11. Zipfel, W. R., Williams, R. M., Christie, R., Nikitin, A. Y., Hyman, B. T. & Webb, W. W. (2003) *Proc Natl Acad Sci USA* 100, 7075-80.
12. Cox, G., Kable, E., Jones, A., Fraser, I., Manconi, F. & Gorrell, M. D. (2003) *J Struct Biol* 141, 53-62.
13. Zoumi, A., Yeh, A. & Tromberg, B. J. (2002) *Proc Nat Acad Sci USA* 99, 11014-9.
14. Centonze, V. E. & White, J. G. (1998) *Biophys J* 75, 2015-24.
15. Denk, W., Strickler, J. H. & Webb, W. W. (1990) *Science* 248, 73-6.

16. Zipfel, W. R., Williams, R. M. & Webb, W. W. (2003) *Nat Biotechnol* 21, 1369-77.
17. Helmchen, F. & Denk, W. (2002) *Curr Opin Neurobiol* 12, 593-601.
18. Mohler, W., Millard, A. C. & Campagnola, P. J. (2003) *Methods* 29, 97-109.
19. Wokosin, D. L., Squirrell, J. M., Eliceiri, K. E. & White, J. G. (2003) *Review of Scientific Instruments* 74.
20. Williams, R. M., Zipfel, W. R. & Webb, W. W. (2005) *Biophys J* 88, 1377-86.
21. Abramoff, M. D., Magelhaes, P. J. & Ram, S. J. (2004) *Biophotonics International* 11, 36-42.
22. Rueden, C., Eliceiri, K. W. & White, J. G. (2004) *Traffic* 5, 411-7.
23. Glauert, A. M. (1980) in *Practical methods in electron microscopy*, ed. Glauert, A. M. (Am. Elsevier Pub. Co, New York), Vol. 3.
24. Parry, D. A., Craig, A. S. (1984) in *Ultrastructure of the connective tissue matrix*, ed. Ruggeri, A., Motta, A. (eds.) (The Hague, Martinus Nijhoff, pp. 34-62.
25. Monaghan, P., Warburton, M. J., Perusinghe, N. & Rudland, P. S. (1983) *Proc Natl Acad Sci USA* 80, 3344-3348.
26. Alowami, S., Troup, S., Al-Haddad, S., Kirkpatrick, I. & Watson, P. H. (2003) *Breast Cancer Res* 5, R129-35.
27. Boyd, N. F., Dite, G. S., Stone, J., Gunasekara, A., English, D. R., McCredie, M. R., Giles, G. G., Tritchler, D., Chiarelli, A., Yaffe, M. J. & Hopper, J. L. (2002) *N Engl J Med* 347, 886-94.
28. Liu, X., Wu, H., Byrne, M., Jeffrey, J., Krane, S. & Jaenisch, R. (1995) *J Cell Biol* 130, 227-37.
29. Brown, E., McKee, T., diTomaso, E., Pluen, A., Seed, B., Boucher, Y. & Jain, R. K. (2003) *Nat Med* 9, 796-800.
30. Li, Y., Hively, W. P. & Varmus, H. E. (2000) *Oncogene* 19, 1002-9.
31. Friedl, P. & Wolf, K. (2003) *Nat Rev Cancer* 3, 362-74.
32. Lin, E. Y., Jones, J. G., Li, P., Zhu, L., Whitney, K. D., Muller, W. J. & Pollard, J. W. (2003) *Am J Pathol* 163, 2113-26.
33. Wolf, K. & Friedl, P. (2005) *Biochimie* 87, 315-20.
34. Hagios, C., Lochter, A. & Bissell, M. J. (1998) *Philos Trans R Soc Lond B Biol Sci* 353, 857-70.
35. Fata, J. E., Werb, Z. & Bissell, M. J. (2004) *Breast Cancer Res* 6, 1-11.
36. Ingman, W., Wyckoff, J., Xue, C., Lin, E. Y., Wang, W., Goswami, S., Pollard, J. W., Condeelis, J. & Segall, J. E. (in press) in *In: Cell Motility in Cancer Invasion and Metastasis*, ed. Wells, A. (Kluwer Academic Publishers.
37. Hurschler, C., Provenzano, P. P. & Vanderby Jr, R. (2003) *ASME Journal of Biomechanical Engineering* 125, 415-422.
38. Diamant, J., Keller, A., Baer, E., Litt, M. & Arridge, R. G. C. (1972) *Proc Royal Soc Lond* 180B, 293-315.
39. Wozniak, M. A., Desai, R., Solski, P. A., Der, C. J. & Keely, P. J. (2003) *J Cell Biol* 163, 583-95.
40. Barsky, S. H., Rao, C. N., Grotendorst, G. R. & Liotta, L. A. (1982) *Am J Pathol* 108, 276-83.
41. Wang, W., Goswami, S., Sahai, E., Wyckoff, J. B., Segall, J. E. & Condeelis, J. S. (2005) *Trends Cell Biol* 15, 138-45.
42. Friedl, P., Hegerfeldt, Y. & Tusch, M. (2004) *Int J Dev Biol* 48, 441-9.
43. Croft, D. R., Sahai, E., Mavria, G., Li, S., Tsai, J., Lee, W. M., Marshall, C. J. & Olson, M. F. (2004) *Cancer Res* 64, 8994-9001.

We claim:

1. A method for evaluating a test tissue sample for the diagnosis of cancer, said method comprising the steps of:
   a) providing the test tissue sample from a test subject, wherein said test tissue sample comprises a stromal collagen component;
   b) generating a test image or test imaging data from the test tissue sample using a nonlinear optical imaging technique; and
   c) analyzing said test image or test imaging data of the test tissue sample by observing the stromal collagen for detection of at least one tumor-associated collagen signature, thereby evaluating said test tissue sample for the diagnosis of cancer;
   wherein said tumor-associated collagen signature is selected from the group consisting of:
      i. a first tumor-associated collagen signature, wherein there is an increased collagen density, localization or deposition level in the test tissue sample relative to a first reference level;
      ii. a second tumor-associated collagen signature, wherein there is an increased level of taut collagen fibers in the test tissue sample relative to a second reference level; and
      iii. a third tumor-associated collagen signature, wherein there is a radial alignment pattern of collagen fibers in the test tissue sample relative to a third reference level.

2. The method of claim 1 wherein said nonlinear optical imaging technique is multiphoton laser-scanning microscopy, second harmonic generation, third harmonic generation or any combination of these.

3. The method of claim 1 wherein said nonlinear optical imaging technique is a combination of multiphoton laser-scanning microscopy and second harmonic generation.

4. The method of claim 1 wherein said test tissue sample is a breast tissue sample.

5. The method of claim 1 wherein said test tissue sample is intact and in situ.

6. The method of claim 1 wherein said analyzing step comprises comparing said test image or test imaging data with a reference image or reference imaging data corresponding to a reference tissue sample.

7. The method of claim 1 wherein said analyzing step comprises observing the stromal collagen for detection of a tumor-associated collagen signature profile comprising a plurality of tumor-associated collagen signatures.

8. The method of claim 1 wherein said first, second, and third reference levels correspond to one or more reference tissues having a normal condition.

9. The method of claim 8 wherein said test tissue sample provides one or more first stromal regions suspected of a cancerous condition; and wherein said first, second, or third reference levels are established from a reference collagen profile said test tissue sample, whereby the test tissue sample also serves as said one or more reference tissues, wherein the reference collagen profile is determined from one or more second stromal regions having a normal condition.

10. The method of claim 8 wherein said test tissue sample is from a first species and said one or more reference tissues are from said first species or from a second species that is different from said first species.

11. The method of claim 10 wherein said first species is human.

12. The method of claim 1 wherein said first, second, and third reference levels correspond to one or more reference tissues having a disease condition.

13. The method of claim 1 wherein said third tumor-associated collagen signature is detected by measuring angles of one or more collagen fibers relative to a tumor boundary or by measuring a distribution of angles of one or more collagen fibers relative to a tumor boundary.

14. The method of claim 13 wherein said angles of one or more collagen fibers relative to a tumor boundary are determined using a curvelet or wavelet analysis.

15. A method for evaluating a test tissue sample for the diagnosis of cancer, said method comprising the steps of:
   a) providing the test tissue sample from a test subject, wherein said test tissue sample comprises a stromal collagen component;
   b) generating a test image or test imaging data from the test tissue sample using a nonlinear optical imaging technique; and
   c) analyzing said test image or test imaging data of the test tissue sample by observing the stromal collagen for detection of a tumor-associated collagen signature profile comprising a plurality of tumor-associated collagen signatures, thereby evaluating said test tissue sample for the diagnosis of cancer;
wherein said tumor-associated collagen signatures are selected from the group consisting of:
   i. a first tumor-associated collagen signature, wherein there is an increased collagen density, localization or deposition level in the test tissue sample relative to a first reference level;
   ii. a second tumor-associated collagen signature, wherein there is an increased level of taut collagen fibers in the test tissue sample relative to a second reference level; and
   iii. a third tumor-associated collagen signature, wherein there is a radial alignment pattern of collagen fibers in the test tissue sample relative to a third reference level.

16. The method of claim 15 wherein said third tumor-associated collagen signature is detected by measuring angles of one or more collagen fibers relative to a tumor boundary or by measuring a distribution of angles of one or more collagen fibers relative to a tumor boundary.

17. The method of claim 16 wherein said angles of one or more collagen fibers relative to a tumor boundary are determined using a curvelet or wavelet analysis.

18. A method of locating a tissue region associated with a cancer risk, said method comprising the steps of: providing a tissue sample, examining the tissue sample by employing a nonlinear optical imaging technique, identifying a tumor-associated collagen signature profile comprising a plurality of tumor-associated collagen signatures in the tissue sample from an image generated by the nonlinear optical imaging technique, and spatially resolving the tumor-associated collagen signature profile with respect to the tissue sample or a three-dimensional representation of the tissue sample; thereby locating said tissue region associated with said cancer risk; wherein said tumor-associated collagen signatures are selected from the group consisting of:
   i. a first tumor-associated collagen signature, wherein there is an increased collagen density, localization or deposition level in the test tissue sample relative to a first reference level;
   ii. a second tumor-associated collagen signature, wherein there is an increased level of taut collagen fibers in the test tissue sample relative to a second reference level; and
   iii. a third tumor-associated collagen signature, wherein there is a radial alignment pattern of collagen fibers in the test tissue sample relative to a third reference level.

19. The method of claim 18 further comprising the step of defining a tissue region margin, wherein said margin is proximal to a first region of suspect tissue and a second region of normal tissue.

20. The method of claim 18 further comprising the step of identifying a candidate tissue removal region.

21. A system for evaluating a test tissue sample for the diagnosis of cancer comprising:
   a) a nonlinear optical imaging device for generating a test image or test imaging data from the test tissue sample using a nonlinear optical imaging technique; and
   b) a processor for analyzing said test image or test imaging data of the test tissue sample, said processor using a pattern recognition algorithm for analyzing said test image or test imaging data for detection of at least one tumor-associated collagen signature, thereby evaluating said test tissue sample for the diagnosis of cancer; wherein said tumor-associated collagen signature is selected from the group consisting of:
      i. a first tumor-associated collagen signature, wherein there is an increased collagen density, localization or deposition level in the test tissue sample relative to a first reference level;
      ii. a second tumor-associated collagen signature, wherein there is an increased level of taut collagen fibers in the test tissue sample relative to a second reference level; and
      iii. a third tumor-associated collagen signature, wherein there is a radial alignment pattern of collagen fibers in the test tissue sample relative to a third reference level.

22. The system of claim 21 comprising a partially automated system or a fully automated system.

23. The system of claim 21 wherein said processor uses said pattern recognition algorithm to analyze said test image or test imaging data using a curvelet or wavelet analysis.

24. The system of claim 21 wherein said nonlinear optical imaging technique is multiphoton laser-scanning microscopy, second harmonic generation, third harmonic generation or any combination of these.

25. The system of claim 21 wherein said nonlinear optical imaging technique is a combination of multiphoton laser-scanning microscopy and second harmonic generation.

26. The system of claim 21 wherein said processor uses said pattern recognition algorithm to compare said test image or test imaging data with a reference image or reference imaging data.

27. The system of claim 26 wherein said first, second, and third reference levels are established from one or more reference tissues having a normal condition.

28. The system of claim 26 wherein said first, second, and third reference levels are established from one or more reference tissues having a disease condition.

29. The system of claim 21 wherein said processor analyzes said test image by observing the stromal collagen for detection of a collagen signature profile comprising at least one of the first tumor-associated collagen signature; the second tumor-associated collagen signature; and the third tumor-associated collagen signature.

30. The system of claim 21 wherein said third tumor-associated collagen signature is detected by measuring angles of one or more collagen fibers relative to a tumor boundary or by measuring a distribution of angles of one or more collagen fibers relative to a tumor boundary.

* * * * *